US007670840B2

(12) United States Patent
Croce et al.

(10) Patent No.: US 7,670,840 B2
(45) Date of Patent: Mar. 2, 2010

(54) MICRO-RNA EXPRESSION ABNORMALITIES OF PANCREATIC, ENDOCRINE AND ACINAR TUMORS

(75) Inventors: Carlo M. Croce, Columbus, OH (US); George A. Calin, Pearland, TX (US)

(73) Assignee: The Ohio State University Research Foundation, Columbus, OH (US)

( * ) Notice: Subject to any disclaimer, the term of this patent is extended or adjusted under 35 U.S.C. 154(b) by 0 days.

(21) Appl. No.: 12/160,064

(22) PCT Filed: Jan. 3, 2007

(86) PCT No.: PCT/US2007/000024

§ 371 (c)(1),
(2), (4) Date: Jul. 3, 2008

(87) PCT Pub. No.: WO2007/081680

PCT Pub. Date: Jul. 19, 2007

(65) Prior Publication Data

US 2008/0306018 A1 Dec. 11, 2008

Related U.S. Application Data

(60) Provisional application No. 60/756,502, filed on Jan. 5, 2006.

(51) Int. Cl.
C12Q 1/68 (2006.01)
C12P 19/34 (2006.01)
C07H 21/02 (2006.01)
C07H 21/04 (2006.01)

(52) U.S. Cl. .................. 436/6; 435/91.1; 435/91.31; 536/23.1; 536/24.31; 536/24.5

(58) Field of Classification Search .................. 436/6, 436/91.1, 91.31; 536/23.1, 24.31, 24.5
See application file for complete search history.

(56) References Cited

U.S. PATENT DOCUMENTS

2004/0152112 A1 8/2004 Croce et al.

2005/0256072 A1 11/2005 Aronin et al.

FOREIGN PATENT DOCUMENTS

| WO | WO2004079013 A1 | 9/2004 |
| WO | WO2005020795 A2 | 3/2005 |
| WO | WO2005078139 A2 | 8/2005 |
| WO | WO2007/081680 A2 | 7/2007 |

OTHER PUBLICATIONS

Croce et al., "miRNAs, Cancer, and Stem Cell Division," Department of Molecular Virology, immunology, and Medical Genetics and Comprehensive Cancer Center, The Ohio State University, Columbus, OH, pp. 6-7, 2005.
Thomson et al., "A custom microarray platform for analysis of microRNA gene expression," Nature Methods, vol. 1 No. 1, Oct. 2004, pp. 1-7.
Jansen, et al., "Epidermal Expression of the Translation Inhibitor Programmed Cell Death 4 Suppresses Tumorigenesis," Cancer Res 2005; 65; (14) Jul. 15, 2005, pp. 6034-6041.
Iorio et al., "MicroRNA Gene Expression Deregulation in Human Breast Cancer," Cancer Res 2005; 65; (16) Aug. 15, 2005, pp. 7065-7070.
PCT International Search Report, Application No. PCT/US07/00024, Filing Date Jan. 3, 2007.
European Search Report Communication, Application No./Patent No. 07716208.9-122/1968622 PCT/US2007000024 dated Oct. 10, 2009.
Guweidhi et al., Enhanced expression of 14-3-3sigma in pancreatic cancer and its role in cell cycle regulation and apoptosis, Carcinogenesis vol. 25, No. 9, 2004, pp. 1575-1585, XP-002552302.
Jiang et al., Real-time expression profiling of microRNA precursors in human cancer cell lines, Nucleic Acids Research, 2005, vol. 33, No. 17, pp. 5394-5403, XP-002489966.
Lu et al., MicroRNA expression profiles classify human cancers, Nature Publishing Group, 2005, vol. 435/9, pp. 834-838, XP-002485555.
Ma et al., Expression of programmed cell death 4 and its clinicopathological significance in human pancreatic cancer, Medline, 2005, Abstract, XP-002552125.
Roldo et al., MicroRNA Expression Abnormalities in Pancreatic Endocrine and Acinar Tumors Are Associated With Distinctive Pathologic Features and Clinical Behavior, Journal of Clinical Oncology, 2006, vol. 24, No. 29, pp. 4677-4684, XP008078235.

*Primary Examiner*—Jane Zara
(74) *Attorney, Agent, or Firm*—MacMillan, Sobanski & Todd, LCC

(57) ABSTRACT

The present invention provides novel methods and compositions for the diagnosis, prognosis and treatment of pancreatic cancer. The invention also provides methods of identifying anti-pancreatic cancer agent.

12 Claims, 7 Drawing Sheets

MICRO-RNA EXPRESSION ABNORMALITIES OF PANCREATIC, ENDOCRINE AND ACINAR TUMORS

GOVERNMENT SUPPORT

The invention was supported, in whole or in part, by Program Project Grants P01CA76259 and P01CA81534 from the National Cancer Institute. The Government has certain rights in the invention.

BACKGROUND OF THE INVENTION

Pancreatic cancers can be classified according to where in the pancreas the cancer is found or according to the type of cell the cancer has originated from. Pancreatic cancer can occur in the head, body or tail of the pancreas and symptoms can vary depending on where in the pancreas the tumor is located. 70-80% of pancreatic cancers occur in the head of the pancreas. The majority of cancers of the pancreas are exocrine in type, and greater than 90% of these exocrine pancreatic cancers are adenocarcinomas. Nearly all of these are ductal adenocarcinomas, wherein the cancer occurs in the cells lining the ducts of the pancreas. In addition, there are rarer types of exocrine pancreatic cancer, such as cystic tumors, cancer of the acinar cells and sarcomas. Cystic tumors are tumors that cause a cyst or fluid-filled sac in the pancreas. Sarcomas, a cancer of the connective tissue holding together the cells of the pancreas, are rare and most often occur in children.

In addition to exocrine cancers, endocrine cancers of the pancreas can occur. The endocrine cancers can be named by reference to the hormone that they produce, e.g., gastrinomas (which produce gastrin), insulinomas (which produce insulin), somatostatinomas (which produce somatostatin), VIPomas (which produce VIP) and glucagonomas (which produce glucagon). In addition, lymphomas of the pancreas can occur, although they are rare.

Pancreatic endocrine tumors (PET) may occur either sporadically or as part of multiple endocrine neoplasia type 1 (MEN1) syndrome (Kloppel, G., et al., *Ann. N.Y. Acad. Sci.* 1014:13-27 (2004)). These neoplasms are clinically classified as functioning (F-PET) or nonfunctioning (NF-PET), according to the presence of symptoms due to hormone hypersecretion. F-PETs are mainly represented by insulinomas. At diagnosis, metastatic disease is observed in only 10% of insulinomas but in up to 60% of NF-PETs, and most PET-related deaths are caused by liver metastasis (Kloppel, G., et al., *Ann. N.Y. Acad. Sci.* 1014:13-27 (2004)). The malignant potential among PETs varies greatly and cannot be predicted on the basis of histological appearance. In fact, the vast majority of PETs are well-differentiated endocrine tumors (WDET) and are defined as well-differentiated endocrine carcinomas (WDEC) only when invasion or metastases are identified (Kloppel, G., et al., *Ann. N.Y. Acad. Sci.* 1014:13-27 (2004)).

Pancreatic acinar cell carcinoma (PACC) is an extremely rare tumor type distinct from ductal adenocarcinoma and PET, although some overlap with PET is observed by both the expression of neuroendocrine markers in one third of the cases and the existence of mixed acinar-endocrine carcinomas (Ohike, N., et al., *Virchows Arch.* 445:231-35 (2004)). PACC is always malignant with a median survival of 18 months, which lies between that of pancreatic ductal adenocarcinoma and endocrine neoplasms (6 months and 40 months, respectively) (Holen, K. D., et al., *J. Clin. Oncol.* 20:4673-78 (2002)).

Little is known about the molecular pathogenesis of PETs (Kloppel, G., et al., *Ann. N.Y. Acad. Sci.* 1014:13-27 (2004)). Inactivation of MEN1 gene is the most frequent genetic event identified in sporadic PET, while mutations in genes typically involved in pancreatic adenocarcinoma are uncommon (Perren, A., et al., *Ann. N.Y. Acad. Sci.* 1014:199-208 (2004)). Even less is known regarding the molecular anomalies of PACC (Abraham, S. C., et al., *Am. J. Pathol.* 160:953-62 (2002)). No gene expression profile data is available for PACC and our understanding of gene expression changes that occur in PET is still at an initial phase (Hansel, D. E., et al., *Clin. Cancer Res.* 10:6152-58 (2004)).

MicroRNAs are small (20-24 nucleotides) noncoding RNA gene products that serve critical roles in many biological processes, such as cell proliferation, apoptosis and developmental timing. To perform these functions, microRNAs negatively regulate the stability and/or translational efficiency of their target mRNAs (Ambros, V., *Nature* 431:350-55 (2004)). Currently, 313 unique mature human microRNAs are known, 223 of which have been experimentally verified in humans (www.microrna.sanger.ac.uk). Recent studies suggest that aberrant expression of particular miRNAs may be involved in human diseases, such as neurological disorders (Ishizuka, A., et al., *Genes Dev.* 16:2497-2508 (2002)) and cancer. In particular, misexpression of miR-16-1 and/or miR-15a has been found in human chronic lymphocytic leukemias (CLL) (Calin, G. A., et al., *Proc. Natl. Acad. Sci. U.S.A.* 99:15524-15529 (2002)). Aberrant expression of microRNAs has been linked to cancers and diagnostic/prognostic characteristics of specific cancer types can be distinguished based on their microRNA profiles (Caldas, C., and J. D. Brenton, *Nature Med.* 11:712-14 (2005); Croce, C. M., and G. A. Calin, *Cell* 122:6-7 (2005)). Functional studies also have linked aberrant microRNA expression to carcinogenesis (Chan, J. A., et al., *Cancer Res.* 65:6029-33 (2005); Cheng, A. M., et al., *Nucleic Acids Res.* 33:1290-97 (2005); He, L., et al, *Nature* 435:828-33 (2005); and Johnson, S. M., et al., *Cell* 120:635-47 (2005)).

The development and use of microarrays containing all known human microRNAs has permitted a simultaneous analysis of the expression of every miRNA in a sample (Liu, C. G., et al., *Proc Natl. Acad. Sci. U.S.A.* 101:9740-9744 (2004)). These microRNA microarrays have not only been used to confirm that miR-16-1 is deregulated in human CLL cells, but also to generate miRNA expression signatures that are associated with well-defined clinicopathological features of human CLL (Calin, G. A., et al., *Proc. Natl. Acad. Sci. U.S.A.* 101:1175-11760 (2004)).

Identification of microRNAs that are differentially-expressed in pancreatic cancer cells may help pinpoint specific miRNAs that are involved in pancreatic cancer (e.g., pancreatic endocrine tumors, acinar carcinomas). Furthermore, the identification of putative targets of these miRNAs may help to unravel their pathogenic role. The present invention provides novel methods and compositions for the diagnosis, prognosis and treatment of pancreatic cancer.

SUMMARY OF THE INVENTION

The present invention is based, in part, on the identification of specific miRNAs associated with altered expression levels in pancreatic cancer cells.

Accordingly, the invention encompasses methods of diagnosing whether a subject has, or is at risk for developing, pancreatic cancer. According to the methods of the invention, the level of at least one miR gene product in a test sample from the subject is compared to the level of a corresponding miR gene product in a control sample. An alteration (e.g., an increase, a decrease) in the level of the miR gene product in the test sample, relative to the level of a corresponding miR gene product in the control sample, is indicative of the subject either having, or being at risk for developing, pancreatic cancer.

In one embodiment, the level of the at least one miR gene product in the test sample is greater than the level of the corresponding miR gene product in the control sample. In another embodiment, the at least one miR gene product is selected from the group consisting of miR-103-2, miR-107, miR-103-1, miR-342, miR-100, miR-24-2, miR-23a, miR-125a, miR-26a-1, miR-24-1, miR-191, miR-15a, miR-368, miR-26b, miR-125b-2, miR-125b-1, miR-26a-2, miR-335, miR-126, miR-1-2, miR-21, miR-25, miR-92-2, miR-130a, miR-93, miR-16-1, miR-145, miR-17, miR-99b, miR-181b-1, miR-146, miR-181b-2, miR-16-2, miR-99a, miR-197, miR-10a, miR-224, miR-92-1, miR-27a, miR-221, miR-320, miR-7-1, miR-29b-2, miR-150, miR-30d, miR-29a, miR-23b, miR-135a-2, miR-223, miR-3p21-v, miR-128b, miR-30b, miR-29b-1, miR-106b, miR-132, miR-214, miR-7-3, miR-29c, miR-367, miR-30c-2, miR-27b, miR-140, miR-10b, miR-20, miR-129-1, miR-340, miR-30a, miR-30c-1, miR-106a, miR-32, miR-95, miR-222, miR-30e, miR-129-2, miR-345, miR-143, miR-182, miR-1-1, miR-133a-1, miR-200c, miR-194-1, miR-210, miR-181c, miR-192, miR-220, miR-213, miR-323, miR-375 and a combination thereof. In yet another embodiment, the at least one miR gene product is selected from the group consisting of miR-103, miR-107 and a combination thereof. In still another embodiment, the at least one miR gene product is selected from the group consisting of miR-23a, miR-26b, miR-192, miR-342 and a combination thereof.

In one embodiment, the level of the at least one miR gene product in the test sample is less than the level of the corresponding miR gene product in the control sample. In another embodiment, the at least one miR gene product is selected from the group consisting of miR-326, miR-155, miR-339, miR-34c, miR-345, miR-152, miR-372, miR-128a and a combination thereof. In yet another embodiment, the at least one miR gene product is miR-155.

In one embodiment, the at least one miR gene product is selected from the group consisting of miR-103, is miR-107, miR-155 and a combination thereof. In another embodiment, the at least one miR gene product is miR-103, which is upregulated in the test sample, as compared to the control sample. In yet another embodiment, the at least one miR gene product is miR-107, which is upregulated in the test sample, as compared to the control sample. In still another embodiment, the at least one miR gene product is miR-155, which is downregulated in the test sample, as compared to the control sample. In a particular embodiment, all three of these miRs (miR-103, miR-107 and miR-155) are compared to the corresponding miRs in the control sample.

In one embodiment, the pancreatic cancer that is diagnosed is a pancreatic endocrine tumor (PET). In another embodiment, the pancreatic cancer that is diagnosed is a pancreatic exocrine tumor (e.g., an adenocarcinoma). In yet another embodiment, the pancreatic cancer that is diagnosed is selected from the group consisting of a pancreatic endocrine tumor (PET) and a pancreatic exocrine tumor (e.g., an adenocarcinoma). In a particular embodiment, the pancreatic cancer that is diagnosed is selected from the group consisting of an acinar cell carcinoma (PACC) and an insulinoma. In yet another embodiment, the pancreatic cancer that is diagnosed is selected from the group consisting of a pancreatic endocrine tumor (PET), a pancreatic acinar cell carcinoma (PACC) and an insulinoma. In still another embodiment, the diagnostic method can be used to diagnose any type of pancreatic cancer.

In one embodiment, the invention is a method of diagnosing whether a subject has, or is at risk for developing, pancreatic acinar cell carcinoma (PACC). In this method, the level of at least one miR gene product in a test sample from the subject is compared to the level of a corresponding miR gene product in a control sample. An alteration (e.g., an increase; a decrease) in the level of the miR gene product in the test sample, relative to the level of a corresponding miR gene product in a control sample, is indicative of the subject either having, or being at risk for developing, PACC. In one embodiment, the level of the at least one miR gene product in the test sample is greater than the level of the corresponding miR gene product in the control sample. In another embodiment, the at least one miR gene product is selected from the group consisting of miR-103-2, miR-25, miR-200c, miR-335, miR-21, miR-103-1, miR-92-1, miR-181b-2, miR-191, miR-93, miR-26a-1, miR-17, miR-20, miR-107, miR-26b, miR-215, miR-92-2, miR-192, miR-342, miR-100, miR-3p21-v, miR-106a, miR-15a, miR-23a, miR-181b-1, miR-128b, miR-106b, miR-194-1, miR-219-1, miR-242 and a combination thereof. In yet another embodiment, the level of the at least one miR gene product in the test sample is less than the level of the corresponding miR gene product in the control sample. In still another embodiment, the at least one miR gene product is selected from the group consisting of miR-218-2, miR-339, miR-326, miR-34c, miR-152, miR-138-2, miR-128a and a combination thereof.

In one embodiment, the invention is a method of diagnosing the type of pancreatic cancer that a subject has. In this method, the level of at least one miR gene product in a test sample from the subject is compared to the level of a corresponding miR gene product in a control sample. An alteration (e.g., an increase, a decrease) in the level of the miR gene product in the test sample, relative to the level of a corresponding miR gene product in a control sample, is indicative of the type of pancreatic cancer.

In one embodiment, the type of pancreatic cancer that is diagnosed is selected from the group consisting of a pancreatic endocrine tumor (PET) and a pancreatic acinar cell carcinoma (PACC). In another embodiment, the level of the at least one miR gene product in the test sample is greater than the level of the corresponding miR gene product in the control sample. In another embodiment, the type of pancreatic cancer is a pancreatic endocrine tumor (PET) and the at least one miR gene product is selected from the group consisting of miR-125a, miR-99a, miR-99b, miR-125b-1, miR-342, miR-130a, miR-100, miR-132, miR-129-2, miR-125b-2 and a combination thereof. In yet another embodiment, the level of the at least one miR gene product in the test sample is less than the level of the corresponding miR gene product in the control sample. In still another embodiment, the type of pancreatic cancer is a pancreatic acinar cell carcinoma (PACC) and the at least one miR gene product is selected from the group consisting of miR-125a, miR-99a, miR-99b, miR-125b-1, miR-342, miR-130a, miR-100, miR-132, miR-129-2, miR-125b-2 and a combination thereof.

In one embodiment, the type of pancreatic cancer that is diagnosed is selected from the group consisting of a well-differentiated endocrine carcinoma (WDEC) and a pancreatic acinar cell carcinoma (PACC). In another embodiment, the level of the at least one miR gene product in the test sample is greater than the level of the corresponding miR gene product in the control sample. In yet another embodiment, the type of pancreatic cancer is a well-differentiated endocrine carcinoma (WDEC) and the at least one miR gene product is selected from the group consisting of miR-125a, miR-99a, miR-132 and a combination thereof. In another embodiment, the level of the at least one miR gene product in the test sample is less than the level of the corresponding miR gene product in the control sample. In still another embodiment, the type of pancreatic cancer is a well-differentiated endocrine carcinoma (WDEC) and the at least one miR gene product is miR-148a.

In one embodiment, the type of pancreatic cancer that is diagnosed is selected from the group consisting of an insulinoma and a non-functioning pancreatic endocrine tumor (NF-PET). In one embodiment, the level of the at least one miR gene product in the test sample is greater than the level of the corresponding miR gene product in the control sample. In another embodiment, the type of pancreatic cancer is an insulinoma and the at least one miR gene product is selected from the group consisting of miR-204, miR-203, miR-211 and a combination thereof.

In one embodiment, the invention is a method of determining the prognosis of a subject with pancreatic cancer. In this method, the level of at least one miR gene product, which is associated with an adverse prognosis in pancreatic cancer, is measured in a test sample (e.g., a pancreatic cancer sample) from the subject. An alteration (e.g., an increase, a decrease) in the level of the miR gene product in the test sample, relative to the level of a corresponding miR gene product in a control sample, is indicative of an adverse prognosis. In one embodiment, the level of the at least one miR gene product in the test sample is greater than the level of the corresponding miR gene product in a control sample. In another embodiment, the at least one miR gene product that is measured is miR-21. In yet another embodiment, the pancreatic cancer is associated with metastasis and/or a high proliferation index.

In one embodiment, the invention is a method of determining whether a pancreatic cancer in a subject is metastatic. In this method, the level of at least one miR gene product is measured in a test sample (e.g., a pancreatic cancer sample) from the subject. An alteration (e.g., an increase, a decrease) in the level of the miR gene product in the test sample, relative to the level of a corresponding miR gene product in a control sample, is indicative of metastasis. In one embodiment, the level of the at least one miR gene product in the test sample is greater than the level of the corresponding miR gene product in the control sample. In another embodiment, the at least one miR gene product is miR-21.

In one embodiment, the invention is a method of determining whether a pancreatic cancer in a subject has a high proliferation index. In this method, the level of at least one miR gene product is measured in a test sample (e.g., a pancreatic cancer sample) from the subject. An alteration (e.g., an increase, a decrease) in the level of the miR gene product in the test sample, relative to the level of a corresponding miR gene product in a control sample, is indicative of a high proliferation index. In one embodiment, the level of the at least one miR gene product in the test sample is greater than the level of the corresponding miR gene product in the control sample. In another embodiment, the at least one miR gene product is miR-21.

In one embodiment, the invention is a method of determining the prognosis of a subject with pancreatic cancer. In this method, the level of PDCD4 is measured in a test sample (e.g., a pancreatic cancer sample) from the subject. An alteration (e.g., an increase, a decrease) in the level of PDCD4 in the test sample, relative to the level of PDCD4 in a control sample, is indicative of an adverse prognosis. In one embodiment, the level of PDCD4 in the test sample is less than the level of PDCD4 in the control sample. In another embodiment, the pancreatic cancer is associated with metastasis and/or a high proliferation index.

The level of the at least one miR gene product can be measured using a variety of techniques that are well known to those of skill in the art (e.g., quantitative or semi-quantitative RT-PCR, Northern blot analysis, solution hybridization detection). In a particular embodiment, the level of at least one miR gene product is measured by reverse transcribing RNA from a test sample obtained from the subject to provide a set of target oligodeoxynucleotides, hybridizing the target oligodeoxynucleotides to one or more miRNA-specific probe oligonucleotides (e.g., a microarray that comprises miRNA-specific probe oligonucleotides) to provide a hybridization profile for the test sample, and comparing the test sample hybridization profile to a hybridization profile generated from a control sample. An alteration in the signal of at least one miRNA in the test sample relative to the control sample is indicative of the subject either having, or being at risk for developing, pancreatic cancer. In one embodiment, the signal of at least one miRNA is upregulated, relative to the signal generated from the control sample. In another embodiment, the signal of at least one miRNA is down-regulated, relative to the signal generated from the control sample. In a particular embodiment, the microarray comprises miRNA-specific probe oligonucleotides for a substantial portion of all known human miRNAs. In a further embodiment, the microarray comprises miRNA-specific probe oligonucleotides for one or more miRNAs selected from the group consisting of miR-103-2, miR-107, miR-103-1, miR-342, miR-100, miR-24-2, miR-23a, miR-125a, miR-26a-1, miR-24-1, miR-191, miR-15a, miR-368, miR-26b, miR-125b-2, miR-125b-1, miR-26a-2, miR-335, miR-126, miR-1-2, miR-21, miR-25, miR-92-2, miR-130a, miR-93, miR-16-1, miR-145, miR-17, miR-99b, miR-181b-1, miR-146, miR-181b-2, miR-16-2, miR-99a, miR-197, miR-10a, miR-224, miR-92-1, miR-27a, miR-221, miR-320, miR-7-1, miR-29b-2, miR-150, miR-30d, miR-29a, miR-23b, miR-135a-2, miR-223, miR-3p21-v, miR-128b, miR-30b, miR-29b-1, miR-106b, miR-132, miR-214, miR-7-3, miR-29c, miR-367, miR-30c-2, miR-27b, miR-140, miR-10b, miR-20, miR-129-1, miR-340, miR-30a, miR-30c-1, miR-106a, miR-32, miR-95, miR-222, miR-30e, miR-129-2, miR-345, miR-143, miR-182, miR-1-1, miR-133a-1, miR-200c, miR-194-1, miR-210, miR-181c, miR-192, miR-220, miR-213, miR-323, miR-375, miR-326, miR-155, miR-339, miR-34c, miR-345, miR-152, miR-372, miR-128a and a combination thereof.

The invention also provides methods of diagnosing whether a subject has, or is at risk for developing, a pancreatic cancer with an adverse prognosis. In this method, the level of at least one miR gene product, which is associated with an adverse prognosis in pancreatic cancer, is measured by reverse transcribing RNA from a test sample obtained from the subject to provide a set of target oligodeoxynucleotides. The target oligodeoxynucleotides are then hybridized to one or more miRNA-specific probe oligonucleotides (e.g., a microarray that comprises miRNA-specific probe oligonucleotides) to provide a hybridization profile for the test sample, and the test sample hybridization profile is compared to a hybridization profile generated from a control sample. An alteration in the signal of at least one miRNA in the test sample relative to the control sample is indicative of the subject either having, or being at risk for developing, a pancreatic cancer with an adverse prognosis. In one embodiment, an alteration in the signal of miR-21 is indicative of the subject either having, or being at risk for developing, a pancreatic cancer with an adverse prognosis.

The invention also encompasses methods of treating pancreatic cancer in a subject, wherein at least one miR gene product is deregulated (e.g., down-regulated, upregulated) in the cancer cells of the subject. When at least one isolated miR gene product is downregulated in the pancreatic cancer cells, the method comprises administering an effective amount of an isolated miR gene product, or an isolated variant or biologically-active fragment thereof, such that proliferation of cancer cells in the subject is inhibited. In one embodiment, the at least one isolated miR gene product that is administered to the subject is selected from the group consisting of miR-326, miR-155, miR-339, miR-34c, miR-345, miR-152, miR-372, miR-128a and a combination thereof (or an isolated variant or biologically-active fragment of one or more of these miRs). When at least one isolated miR gene product is upregulated in the cancer cells, the method comprises administering to the subject an effective amount of at least one compound for inhibiting expression of the at least one miR gene product, such that proliferation of pancreatic cancer cells is inhibited. In one embodiment, the compound for inhibiting expression of the at least one miR gene product inhibits a miR gene product selected from the group consisting of miR-103-2, miR-107, miR-103-1, miR-342, miR-100, miR-24-2, miR-23a, miR-125a, miR-26a-1, miR-24-1, miR-191, miR-15a, miR-368, miR-26b, miR-125b-2, miR-125b-1, miR-26a-2, miR-335, miR-126, miR-1-2, miR-21, miR-25, miR-92-2, miR-130a, miR-93, miR-16-1, miR-145, miR-17, miR-99b, miR-181b-1, miR-146, miR-181b-2, miR-16-2, miR-99a, miR-197, miR-10a, miR-224, miR-92-1, miR-27a, miR-221, miR-320, miR-7-1, miR-29b-2, miR-150, miR-30d, miR-29a, miR-23b, miR-135a-2, miR-223, miR-3p21-v, miR-128b, miR-30b, miR-29b-1, miR-106b, miR-132, miR-214, miR-7-3, miR-29c, miR-367, miR-30c-2, miR-27b, miR-140, miR-10b, miR-20, miR-129-1, miR-340, miR-30a, miR-30c-1, miR-106a, miR-32, miR-95, miR-222, miR-30e, miR-129-2, miR-345, miR-143, miR-182, miR-1-1, miR-133a-1, miR-200c, miR-194-1, miR-210, miR-181c, miR-192, miR-220, miR-213, miR-323, miR-375 and a combination thereof.

In a related embodiment, the methods of treating pancreatic cancer in a subject additionally comprise the step of first determining the amount of at least one miR gene product in pancreatic cancer cells from the subject, and comparing that level of the miR gene product to the level of a corresponding miR gene product in control cells. If expression of the miR gene product is deregulated (e.g., downregulated, upregulated) in pancreatic cancer cells, the methods further comprise altering the amount of the at least one miR gene product expressed in the pancreatic cancer cells. In one embodiment, the amount of the miR gene product expressed in the cancer cells is less than the amount of the miR gene product expressed in control cells, and an effective amount of the miR gene product, or an isolated variant or biologically-active fragment thereof, is administered to the subject. In another embodiment, the amount of the miR gene product expressed in the cancer cells is greater than the amount of the miR gene product expressed in control cells, and an effective amount of at least one compound for inhibiting expression of the at least one miR gene is administered to the subject. Suitable miRs and compounds that inhibit expression of miR genes include, for example, those described herein.

The invention further provides pharmaceutical compositions for treating pancreatic cancer. In one embodiment, the pharmaceutical compositions comprise at least one isolated miR gene product, or an isolated variant or biologically-active fragment thereof, and a pharmaceutically-acceptable carrier. In a particular embodiment, the at least one miR gene product corresponds to a miR gene product that has a decreased level of expression in pancreatic cancer cells relative to suitable control cells (i.e., it is downregulated). In a certain embodiment, the isolated miR gene product is selected from the group consisting of miR-326, miR-155, miR-339, miR-34c, miR-345, miR-152, miR-372, miR-128a and a combination thereof.

In another embodiment, the pharmaceutical compositions of the invention comprise at least one miR expression-inhibition compound and a pharmaceutically-acceptable carrier. In a particular embodiment, the at least one miR expression-inhibition compound is specific for a miR gene product whose expression is greater in pancreatic cancer cells than control cells (i.e., it is upregulated). In certain embodiments, the miR expression-inhibition compound is specific for one or more miR gene products selected from the group consisting of miR-103-2, miR-107, miR-103-1, miR-342, miR-100, miR-24-2, miR-23a, miR-125a, miR-26a-1, miR-24-1, miR-191, miR-15a, miR-368, miR-26b, miR-125b-2, miR-125b-1, miR-26a-2, miR-335, miR-126, miR-1-2, miR-21, miR-25, miR-92-2, miR-130a, miR-93, miR-16-1, miR-145, miR-17, miR-99b, miR-181b-1, miR-146, miR-181b-2, miR-16-2, miR-99a, miR-197, miR-10a, miR-224, miR-92-1, miR-27a, miR-221, miR-320, miR-7-1, miR-29b-2, miR-150, miR-30d, miR-29a, miR-23b, miR-135a-2, miR-223, miR-3p21-v, miR-128b, miR-30b, miR-29b-1, miR-106b, miR-132, miR-214, miR-7-3, miR-29c, miR-367, miR-30c-2, miR-27b, miR-140, miR-10b, miR-20, miR-129-1, miR-340, miR-30a, miR-30c-1, miR-106a, miR-32, miR-95, miR-222, miR-30e, miR-129-2, miR-345, miR-143, miR-182, miR-1-1, miR-133a-1, miR-200c, miR-194-1, miR-210, miR-181c, miR-192, miR-220, miR-213, miR-323, miR-375 and a combination thereof.

The invention also encompasses methods of identifying an anti-pancreatic cancer agent, comprising providing a test agent to a cell and measuring the level of at least one miR gene product in the cell. In one embodiment, the method comprises providing a test agent to a cell and measuring the level of at least one miR gene product associated with decreased expression levels in pancreatic cancer cells. An increase in the level of the miR gene product in the cell, relative to a suitable control cell, is indicative of the test agent being an anti-pancreatic cancer agent. In a particular embodiment, the at least one miR gene product associated with decreased expression levels in pancreatic cancer cells is selected from the group consisting of miR-326, miR-155, miR-339, miR-34c, miR-345, miR-152, miR-372, miR-128a and a combination thereof.

In other embodiments, the method comprises providing a test agent to a cell and measuring the level of at least one miR gene product associated with increased expression levels in pancreatic cancer cells. A decrease in the level of the miR gene product associated with increased expression levels in pancreatic cancer in the cell, relative to a suitable control cell, is indicative of the test agent being an anti-pancreatic cancer agent. In a particular embodiment, the at least one miR gene product associated with increased expression levels in pancreatic cancer cells is selected from the group consisting of miR-103-2, miR-107, miR-103-1, miR-342, miR-100, miR-24-2, miR-23a, miR-125a, miR-26a-1, miR-24-1, miR-191, miR-15a, miR-368, miR-26b, miR-125b-2, miR-125b-1, miR-26a-2, miR-335, miR-126, miR-1-2, miR-21, miR-25, miR-92-2, miR-130a, miR-93, miR-16-1, miR-145, miR-17, miR-99b, miR-181b-1, miR-146, miR-181b-2, miR-16-2, miR-99a, miR-197, miR-10a, miR-224, miR-92-1, miR-27a, miR-221, miR-320, miR-7-1, miR-29b-2, miR-150, miR-30d, miR-29a, miR-23b, miR-135a-2, miR-223, miR-3p21- v, miR-128b, miR-30b, miR-29b-1, miR-106b, miR-132, miR-214, miR-7-3, miR-29c, miR-367, miR-30c-2, miR-27b, miR-140, miR-10b, miR-20, miR-129-1, miR-340, miR-30a, miR-30c-1, miR-106a, miR-32, miR-95, miR-222, miR-30e, miR-129-2, miR-345, miR-143, miR-182, miR-1-1, miR-133a-1, miR-200c, miR-194-1, miR-210, miR-181c, miR-192, miR-220, miR-213, miR-323, miR-375 and a combination thereof.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

Figures 1A, 1B, 1C, 1D, 1E:
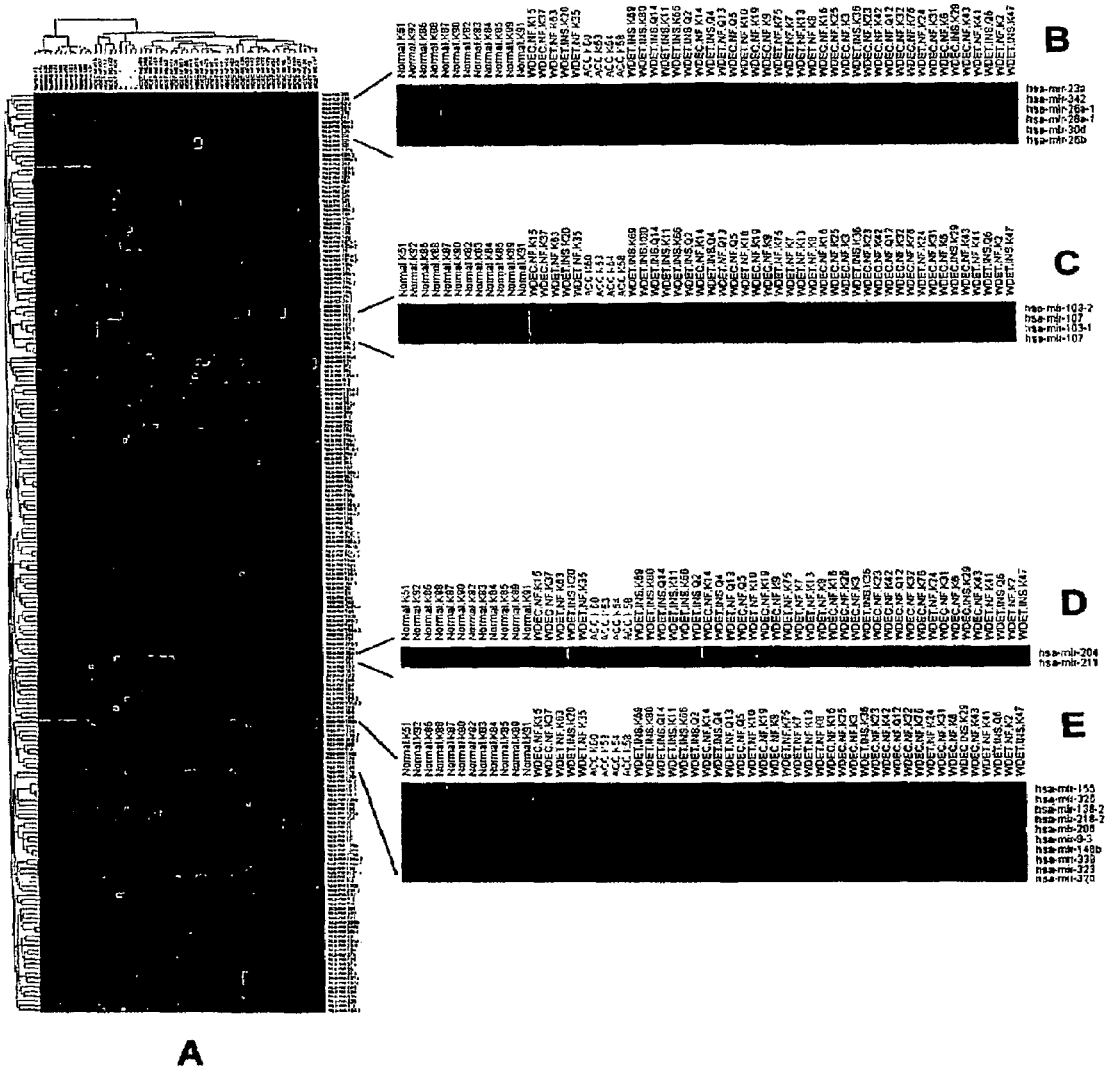
FIG. 1A depicts an miRNA expression unsupervised hierarchical cluster view of 12 normal pancreas (Normal) and 44 pancreatic tumors, including 22 well-differentiated pancreatic endocrine tumors (WDET), 18 well-differentiated pancreatic endocrine carcinomas (WDEC) and 4 pancreatic acinar cell carcinomas (ACC) (listed at top). WDET samples included 11 insulinomas (INS) and 1 Non-functioning PET (NF); WDEC samples included 1 INS and 17 NF-PET. The analysis was performed using the aggregate values of replicate spots obtained applying median polish algorithm and selecting the first 200 probes with the higher interquartile range, which contained the mature microRNA sequences. Notably, PACC samples fell in a unique cluster that was part of the wider cluster including all PETs, while there was no distinctive pattern between insulinomas and NF-PET. As is depicted, a common microRNA expression pattern distinguishes pancreatic endocrine and acinar tumors from normal pancreas.
FIG. 1B depicts particular microRNAs that are found to be upregulated in PET versus Normal tissue (upregulated microRNAs are listed in red).
FIG. 1C depicts particular microRNAs that are found to be upregulated in PET versus Normal tissue (upregulated microRNAs are listed in red).
FIG. 1D depicts two microRNAs that are upregulated in insulinoma versus Non-functioning PET ((upregulated microRNAs are listed in blue).
FIG. 1E depicts particular microRNAs that are found to be downregulated in PET versus Normal tissue (downregulated microRNAs are listed in green).

The present invention is based, in part, on the identification of particular microRNAs having altered expression in pancreatic cancer cells relative to normal control cells, and on association of these microRNAs with particular diagnostic, prognostic and therapeutic features. As described herein:

i) a common pattern of microRNA expression distinguishes pancreatic tumor types from normal pancreas, and thereby implicates the involvement of particular microRNAs in pancreatic tumorigenesis;

ii) the expression of miR-103 and miR-107, associated with lack of expression of miR-155, discriminates pancreatic tumors from normal pancreas;

iii) at least 10 microRNAs distinguishes endocrine tumors from acinar tumors, and implicates particular microRNAs in endocrine differentiation and/or endocrine tumorigenesis;

iv) miR-204 is primarily expressed in insulinomas and correlates with immunohistochemical expression of insulin; and v) over-expression of miR-21 is strongly associated with both a high Ki67 proliferation index and the presence of liver metastasis.

These results imply that alteration in microRNA expression is related to endocrine and acinar neoplastic transformation and progression of malignancy. Accordingly, expression of particular microRNAs, as well as alterations of such microRNA expression, can be used in the diagnostic, prognostic and therapeutic methods described herein.

As used herein interchangeably, a "miR gene product," "microRNA," "miR," or "miRNA" refers to the unprocessed or processed RNA transcript from a miR gene. As the miR gene products are not translated into protein, the term "miR gene products" does not include proteins. The unprocessed miR gene transcript is also called a "miR precursor," and typically comprises an RNA transcript of about 70-100 nucleotides in length. The miR precursor can be processed by digestion with an RNAse (for example, Dicer, Argonaut, RNAse III (e.g., *E. coli* RNAse III)) into an active 19-25 nucleotide RNA molecule. This active 19-25 nucleotide RNA molecule is also called the "processed" miR gene transcript or "mature" miRNA.

The active 19-25 nucleotide RNA molecule can be obtained from the miR precursor through natural processing routes (e.g., using intact cells or cell lysates) or by synthetic processing routes (e.g., using isolated processing enzymes, such as isolated Dicer, Argonaut, or RNAse III). It is understood that the active 19-25 nucleotide RNA molecule can also be produced directly by biological or chemical synthesis, without having to be processed from the miR precursor. When a microRNA is referred to herein by name, the name corresponds to both the precursor and mature forms, unless otherwise indicated.

The present invention encompasses methods of diagnosing whether a subject has, or is at risk for developing, pancreatic cancer, comprising measuring the level of at least one miR gene product in a test sample from the subject and comparing the level of the miR gene product in the test sample to the level of a corresponding miR gene product in a control sample. As used herein, a "subject" can be any mammal that has, or is suspected of having, pancreatic cancer. In a preferred embodiment, the subject is a human who has, or is suspected of having, pancreatic cancer.

The pancreatic cancer can be any form of pancreatic cancer, for example, pancreatic cancers of differing histology (e.g., exocrine tumors, endocrine tumors, carcinomas, lymphomas). In one embodiment, the pancreatic cancer that is diagnosed is a pancreatic endocrine tumor (PET). In another embodiment, the pancreatic cancer that is diagnosed is a pancreatic exocrine tumor (e.g., an adenocarcinoma). In yet another embodiment, the pancreatic cancer that is diagnosed is selected from the group consisting of a pancreatic endocrine tumor (PET) and a pancreatic exocrine tumor (e.g., an adenocarcinoma). In a particular embodiment, the pancreatic cancer that is diagnosed is selected from the group consisting of an acinar cell carcinoma (PACC) and an insulinoma. In yet another embodiment, the pancreatic cancer that is diagnosed is selected from the group consisting of a pancreatic endocrine tumor (PET), a pancreatic acinar cell carcinoma (PACC) and an insulinoma. Furthermore, as described herein, the pancreatic cancer may be associated with a particular prognosis (e.g., low survival rate, fast progression).

Tables 1a and 1b depict the nucleotide sequences of particular precursor and mature human microRNAs.

TABLE 1a

Human microRNA Precursor Sequences.

| Precursor Name | Sequence (5' To 3')* | SEQ ID NO. |
|---|---|---|
| let-7a-1 | CACUGUGGGAUGAGGUAGUAGGUUGUAUAGUUUUAGGGUCACACCCACCACUGGGAGAUAACUAUACAAUCUACUGUCUUUCCUAACGUG | 1 |
| let-7a-2 | AGGUUGAGGUAGUAGGUUGUAUAGUUUAGAAUUACAUCAAGGGAGAUAACUGUACAGCCUCCUAGCUUUCCU | 2 |
| let-7a-3 | GGGUGAGGUAGUAGGUUGUAUAGUUUGGGGCUCUGCCCUGCUAUGGGAUAACUAUACAAUCUACUGUCUUUCCU | 3 |
| let-7a-4 | GUGACUGCAUGCUCCCAGGUUGAGGUAGUAGGUUGUAUAGUUUAGAAUUACACAAGGGAGAUAACUGUACAGCCUCCUAGCUUUCCUUGGGUCUUGCACUAAACAAC | 4 |
| let-7b | GGCGGGGUGAGGUAGUAGGUUGUGUGGUUUCAGGGCAGUGAUGUUGCCCCUCGGAAGAUAACUAUACAACCUACUGCCUUCCCUG | 5 |
| let-7c | GCAUCCGGGUUGAGGUAGUAGGUUGUAUGGUUUAGAGUUACACCCUGGGAGUUAACUGUACAACCUUCUAGCUUUCCUUGGAGC | 6 |
| let-7d | CCUAGGAAGAGGUAGUAGGUUGCAUAGUUUUAGGGCAGGGAUUUUGCCCACAAGGAGGUAACUAUACGACCUGCUGCCUUUCUUAGG | 7 |
| let-7d-v1 | CUAGGAAGAGGUAGUAGUUUGCAUAGUUUUAGGGCAAAGAUUUUGCCCACAAGUAGUUAGCUAUACGACCUGCAGCCUUUUGUAG | 8 |
| let-7d-v2 | CUGGCUGAGGUAGUAGUUUGUGCUGUUGGUCGGGUUGUGACAUUGCCCGCUGUGGAGAUAACUGCGCAAGCUACUGCCUUGCUAG | 9 |
| let-7e | CCCGGGCUGAGGUAGGAGGUUGUAUAGUUGAGGAGGACACCCAAGGAGAUCACUAUACGGCCUCCUAGCUUUCCCCAGG | 10 |
| let-7f-1 | UCAGAGUGAGGUAGUAGAUUGUAUAGUUGUGGGGUAGUGAUUUUACCCUGUUCAGGAGAUAACUAUACAAUCUAUUGCCUUCCCUGA | 11 |

TABLE 1a-continued

Human microRNA Precursor Sequences.

| Precursor Name | Sequence (5' To 3')* | SEQ ID NO. |
|---|---|---|
| let-7f-2-1 | CUGUGGGAUGAGGUAGUAGAUUGUAUAGUUGUGGGGUAGUGAUUUUACCCUGUUCAGGAGAUAACUAUACAAUCUAUUGCCUUCCCUGA | 12 |
| let-7f-2-2 | CUGUGGGAUGAGGUAGUAGAUUGUAUAGUUUUAGGGUCAUACCCCAUCUUGGAGAUAACUAUACAGUCUACUGUCUUUCCCACGG | 13 |
| let-7g | UUGCCUGAUUCCAGGCUGAGGUAGUAGUUUGUACAGUUUGAGGGUCUAUGAUACCACCCGGUACAGGAGAUAACUGUACAGGCCACUGCCUUGCCAGGAACAGCGCGC | 14 |
| let-7i | CUGGCUGAGGUAGUAGUUUGUGCUGUUGGUCGGGUUGUGACAUUGCCCGCUGUGGAGAUAACUGCGCAAGCUACUGCCUUGCUAG | 15 |
| miR-1b-1-1 | ACCUACUCAGAGUACAUACUUCUUUAUGUACCCAUAUGAACAUACAAUGCUAUGGAAUGUAAAGAAGUAUGUAUUUUGGUAGGC | 16 |
| miR-1b-1-2 | CAGCUAACAACUUAGUAAUACCUACUCAGAGUACAUACUUCUUUAUGUACCCAUAUGAACAUACAAUGCUAUGGAAUGUAAAGAAGUAUGUAUUUUUGGUAGGCAAUA | 17 |
| miR-1b-2 | GCCUGCUUGGGAAACAUACUUCUUUAUAUGCCCAUAUGGACCUGCUAAGCUAUGGAAUGUAAAGAAGUAUGUAUCUCAGGCCGGG | 18 |
| miR-1b | UGGGAAACAUACUUCUUUAUAUGCCCAUAUGGACCUGCUAAGCUAUGGAAUGUAAAGAAGUAUGUAUCUCA | 19 |
| miR-1d | ACCUACUCAGAGUACAUACUUCUUUAUGUACCCAUAUGAACAUACAAUGCUAUGGAAUGUAAAGAAGUAUGUAUUUUGGUAGGC | 20 |
| miR-7-1a | UGGAUGUUGGCCUAGUUCUGUGUGGAAGACUAGUGAUUUUGUUGUUUUAGAUAACUAAAUCGACAACAAAUCACAGUCUGCCAUAUGGCACAGGCCAUGCCUCUACA | 21 |
| miR-7-1b | UUGGAUGUUGGCCUAGUUCUGUGUGGAAGACUAGUGAUUUUGUUGUUUUAGAUAACUAAAUCGACAACAAAUCACAGUCUGCCAUAUGGCACAGGCCAUGCCUCUACAG | 22 |
| miR-7-2 | CUGGAUACAGAGUGGACCGGCUGGCCCCAUCUGGAAGACUAGUGAUUUUGUUGUUGUCUUACUGCGCUCAACAACAAAUCCCAGCUCUACCUAAUGGUGCCAGCCAUCGCA | 23 |
| miR-7-3 | AGAUUAGAGUGGCUGUGGUCUAGUGCUGUGUGGAAGACUAGUGAUUUUGUUGUUCUGAUGUACUACGACAACAAGUCACAGCCGGCCUCAUAGCGCAGACUCCCUUCGAC | 24 |
| miR-9-1 | CGGGGUUGGUUGUUAUCUUUGGUUAUCUAGCUGUAUGAGUGGUGUGGAGUCUUCAUAAAGCUAGAUAACCGAAAGUAAAAAUAACCCCA | 25 |
| miR-9-2 | GGAAGCGAGUUGUUAUCUUUGGUUAUCUAGCUGUAUGAGUGUAUUGGUCUUCAUAAAGCUAGAUAACCGAAAGUAAAAACUCCUUCA | 26 |
| miR-9-3 | GGAGGCCCGUUUCUCUCUUUGGUUAUCUAGCUGUAUGAGUGCCACAGAGCCGUCAUAAAGCUAGAUAACCGAAAGUAAAAUGAUUCUCA | 27 |
| miR-10a | GAUCUGUCUGUCUUCUGUAUAUACCCUGUAGAUCCGAAUUUGUGUAAGGAAUUUUGUGGUCACAAAUUCGUAUCUAGGGGAAUAUGUAGUUGACAUAAACACUCCGCUCU | 28 |
| miR-10b | CCAGAGGUUGUAACGUUGUCUAUAUAUACCCUGUAGAACCGAAUUUGUGUGGUAUCCGUAUAGUCACAGAUUCGAUUCUAGGGGAAUAUAUGGUCGAUGCAAAAACUUCA | 29 |
| miR-15a-2 | GCGCGAAUGUGUGUUUAAAAAAAAUAAAACCUUGGAGUAAAGUAGCAGCACAUAAUGGUUUGUGGAUUUUGAAAAGGUGCAGGCCAUAUUGUGCUGCCUCAAAAAUAC | 30 |
| miR-15a | CCUUGGAGUAAAGUAGCAGCACAUAAUGGUUUGUGGAUUUUGAAAAGGUGCAGGCCAUAUUGUGCUGCCUCAAAAAUACAAGG | 31 |
| miR-15b-1 | CUGUAGCAGCACAUCAUGGUUUACAUGCUACAGUCAAGAUGCGAAUCAUUAUUUGCUGCUCUAG | 32 |
| miR-15b-2 | UUGAGGCCUUAAAGUACUGUAGCAGCACAUCAUGGUUUACAUGCUACAGUCAAGAUGCGAAUCAUUAUUUGCUGCUCUAGAAAUUUAAGGAAAUUCAU | 33 |
| miR-16-1 | GUCAGCAGUGCCUUAGCAGCACGUAAAUAUUGGCGUUAAGAUUCUAAAAUUAUCUCCAGUAUUAACUGUGCUGCUGAAGUAAGGUUGAC | 34 |
| miR-16-2 | GUUCCACUCUAGCAGCACGUAAAUAUUGGCGUAGUGAAAUAUAUAUUAAACACCAAUAUUACUGUGCUGCUUUAGUGUGAC | 35 |
| miR-16-13 | GCAGUGCCUUAGCAGCACGUAAAUAUUGGCGUUAAGAUUCUAAAAUUAUCUCCAGUAUUAACUGUGCUGCUGAAGUAAGGU | 36 |
| miR-17 | GUCAGAAUAAUGUCAAAGUGCUUACAGUGCAGGUAGUGAUAUGUGCAUCUACUGCAGUGAAGGCACUUGUAGCAUUAUGGUGAC | 37 |
| miR-18 | UGUUCUAAGGUGCAUCUAGUGCAGAUAGUGAAGUAGAUUAGCAUCUACUGCCCUAAGUGCUCCUUCUGGCA | 38 |
| miR-18-13 | UUUUUGUUCUAAGGUGCAUCUAGUGCAGAUAGUGAAGUAGAUUAGCAUCUACUGCCCUAAGUGCUCCUUCUGGCAUAAGAA | 39 |
| miR-19a | GCAGUCCUCUGUUAGUUUUGCAUAGUUGCACUACAAGAAGAAUGUAGUUGUGCAAAUCUAUGCAAAACUGAUGGUGGCCUGC | 40 |
| miR-19a-13 | CAGUCCUCUGUUAGUUUUGCAUAGUUGCACUACAAGAAGAAUGUAGUUGUGCAAAUCUAUGCAAAACUGAUGGUGGCCUG | 41 |
| miR-19b-1 | CACUGUUCUAUGGUUAGUUUUGCAGGUUUGCAUCCAGCUGUGUGAUAUUCUGCUGUGCAAAUCCAUGCAAAACUGACUGUGGUAGUG | 42 |
| miR-19b-2 | ACAUUGCUACUUACAAUUAGUUUUGCAGGUUUGCAUUUCAGCGUAUAUAUGUAUAUGUGGCUGUGCAAAUCCAUGCAAAACUGAUUGUGAUAAUGU | 43 |
| miR-19b-13 | UUCUAUGGUUAGUUUUGCAGGUUUGCAUCCAGCUGUGUGAUAUUCUGCUGUGCAAAUCCAUGCAAAACUGACUGUGGUAG | 44 |
| miR-19b-X | UUACAAUUAGUUUUGCAGGUUUGCAUUUCAGCGUAUAUAUGUAUAUGUGGCUGUGCAAAUCCAUGCAAAACUGAUUGUGAU | 45 |

TABLE 1a-continued

Human microRNA Precursor Sequences.

| Precursor Name | Sequence (5' To 3')* | SEQ ID NO. |
|---|---|---|
| miR-20 (miR-20a) | GUAGCACUAAAGUGCUUAUAGUGCAGGUAGUGUUUAGUUAUCUACUGCAUUAUGAGCACUUAAAGUACUGC | 46 |
| miR-21 | UGUCGGGUAGCUUAUCAGACUGAUGUUGACUGUUGAAUCUCAUGGCAACACCAGUCGAUGGGCUGUCUGACA | 47 |
| miR-21-17 | ACCUUGUCGGGUAGCUUAUCAGACUGAUGUUGACUGUUGAAUCUCAUGGCAACACCAGUCGAUGGGCUGUCUGACAUUUUG | 48 |
| miR-22 | GGCUGAGCCGCAGUAGUUCUUCAGUGGCAAGCUUUAUGUCCUGACCCAGCUAAAGCUGCCAGUUGAAGAACUGUUGCCCUCUGCC | 49 |
| miR-23a | GGCCGGCUGGGGUUCCUGGGGAUGGGAUUUGCUUCCUGUCACAAAUCACAUUGCCAGGGAUUUCCAACCGACC | 50 |
| miR-23b | CUCAGGUGCUCUGGCUGCUUGGGUUCCUGGCAUGCUGAUUUGUGACUUAAGAUUAAAUCACAUUGCCAGGGAUUACCACGCAACCACGACCUUGGC | 51 |
| miR-23-19 | CCACGGCCGGCUGGGGUUCCUGGGGAUGGGAUUGCUUCCUGUCACAAAUCACAUUGCCAGGGAUUUCCAACCGACCCUGA | 52 |
| miR-24-1 | CUCCGGUGCCUACUGAGCUGAUAUCAGUUCUCAUUUUACACACUGGCUCAGUUCAGCAGGAACAGGAG | 53 |
| miR-24-2 | CUCUGCCUCCCGUGCCUACUGAGCUGAAACACAGUUGGUUUGUGUACACUGGCUCAGUUCAGCAGGAACAGGG | 54 |
| miR-24-19 | CCCUGGGCUCUGCCUCCCGUGCCUACUGAGCUGAAACAGUUGGUUUGUGUACACUGGCUCAGUUCAGCAGGAACAGGGG | 55 |
| miR-24-9 | CCCUCCGGUGCCUACUGAGCUGAUAUCAGUUCUCAUUUUACACACUGGCUCAGUUCAGCAGGAACAGCAUC | 56 |
| miR-25 | GGCCAGUGUUGAGAGGCGGAGACUUGGGCAAUUGCUGGACGCUGCCCUGGGCAUUGCACUUGUCUCGGUCUGACAGUGCCGGCC | 57 |
| miR-26a | AGGCCGUGGCCUCGUUCAAGUAAUCCAGGAUAGGCUGUGCAGGUCCCAAUGGGCCUAUCUUGGUUACUUGCACGGGACGCGGGCCU | 58 |
| miR-26a-1 | GUGGCCUCGUUCAAGUAAUCCAGGAUAGGCUGUGCAGGUCCCAAUGGGCCUAUUCUUGGUUACUUGCACGGGACGC | 59 |
| miR-26a-2 | GGCUGUGGCUGGAUUCAAGUAAUCCAGGAUAGGCUGUUUCCAUCUGUGAGGCCUAUUCUUGAUUACUUGUUUCUGGAGGCAGCU | 60 |
| miR-26b | CCGGGACCCAGUUCAAGUAAUUCAGGAUAGGUUGUGUGCUGUCCAGCCUGUUCUCCAUUACUUGGCUCGGGACCGG | 61 |
| miR-27a | CUGAGGAGCAGGGCUUAGCUGCUUGUGAGCAGGGUCCACACCAAGUCGUGUUCACAGUGGCUAAGUUCCGCCCCCAG | 62 |
| miR-27b-1 | AGGUGCAGAGCUUAGCUGAUUGGUGAACAGUGAUUGGUUUCCGCUUUGUUCACAGUGGCUAAGUUCUGCACCU | 63 |
| miR-27b-2 | ACCUGUCUAACAAGGUGCAGAGCUUAGCUGAUUGGUGAACAGUGAUUGGUUUCCGCUUUGUUCACAGUGGCUAAGUUCUGCACCUGAAGAGAAGGUG | 64 |
| miR-27-19 | CCUGAGGAGCAGGGCUUAGCUGCUUGUGAGCAGGGUCCACACCAAGUCGUGUUCACAGUGGCUAAGUUCCGCCCCCAGG | 65 |
| miR-28 | GGUCCUUGCCCUCAAGGAGCUCACAGUCUAUUGAGUUACCUUUCUGACUUUCCCACUAGAUUGUGAGCUCCUGGAGGGCAGGCACU | 66 |
| miR-29a-2 | CCUUCUGUGACCCCUUAGAGGAUGACUGAUUUCUUUUGGUGUUCAGAGUCAAUAUAAUUUUCUAGCACCAUCUGAAAUCGGUUAUAAUGAUUGGGAAGAGCACCAUG | 67 |
| miR-29a | AUGACUGAUUUCUUUUGGUGUUCAGAGUCAAUAUAAUUUUCUAGCACCAUCUGAAAUCGGUUAU | 68 |
| miR-29b-1 | CUUCAGGAAGCUGGUUUCAUAUGGUGGUUUAGAUUUAAAUAGUGAUUGUCUAGCACCAUUUGAAAUCAGUGUUCUUGGGGG | 69 |
| miR-29b-2 | CUUCGGAAGCUGGUUUCACAUGGUGGCUUAGAUUUUUCAUCUUUGUACAUUUCUAGCACCAUUUGAAAUCAGUGUUUUAGGAG | 70 |
| miR-29c | ACCACUGGCCCAUCUCUUACACAGGCUGACCGAUUUCUCCUGGUUUCAGAUGCUGUUUUUGUCUAGCACCAUUUGAAAUCGGUUAUGAUGUAGGGGGAAAAGCAGCAGC | 71 |
| miR-30a | GCGACUGUAAACAUCCUCGACUGGAAGCUGUGAAGCCACAGAUGGGCUUUCAGUCGGAUGUUUGCAGCUGC | 72 |
| miR-30b-1 | AUGUAAACAUCCUACACUCAGCUGUAAUACAUGGAUUGGCUGGGAGGUGGAUGUUUACGU | 73 |
| miR-30b-2 | ACCAAGUUUCAGUUCAUGUAAACAUCCUACACUCAGCUGUAAUACAUGGAUUGGCUGGGAGGUGGAUGUUUACUUCAGCUGACUGGA | 74 |
| miR-30c | AGAUACUGUAAACAUCCUACACUCUCAGCUGUGGAAAGUAAGAAAGCUGGGAGAAGGCUGUUUACUCUUUCU | 75 |
| miR-30d | GUUGUUGUAAACAUCCCCGACUGGAAGCUGUAAGACACAGCUAAGCUUUCAGUCAGAUGUUUGCUGCUAC | 76 |
| miR-30e | CUGUAAACAUCCUUGACUGGAAGCUGUAAGGUGUUCAGAGGAGCUUUCAGUCGGAUGUUUACAG | 77 |
| miR-31 | GGAGAGGAGGCAAGAUGCUGGCAUAGCUGUUGAACUGGGAACCUGCUAUGCCAACAUAUUGCCAUCUUUCC | 78 |
| miR-32 | GGAGAUAUUGCACAUUACUAAGUUGCAUGUUGUCACGGCCUCAAUGCAAUUUAGUGUGUGUGAUAUUUUC | 79 |
| miR-33b | GGGGGCCGAGAGAGGCGGGCGGCCCCGCGGUGCAUUGCUGUUGCAUUGCACGUGUGUGAGGCGGGUGCAGUGCCUCGGCAGUGCAGCCCGGAGCCGGCCCCUGGCACCAC | 80 |
| miR-33b-2 | ACCAAGUUUCAGUUCAUGUAAACAUCCUACACUCAGCUGUAAUACAUGGAUUGGCUGGGAGGUGGAUGUUUACUUCAGCUGACUGGA | 81 |

TABLE 1a-continued

Human microRNA Precursor Sequences.

| Precursor Name | Sequence (5' To 3')* | SEQ ID NO. |
|---|---|---|
| miR-33 | CUGUGGUGCAUUGUAGUUGCAUUGCAUGUUCUGGUGGUACCCAUGCAAUGUUUCCACAGUGCAUCACAG | 82 |
| miR-34-a | GGCCAGCUGUGAGUGUUUCUUUGGCAGUGUCUUAGCUGGUUGUUGUGAGCAAUAGUAAGGAAGCAAUCAGCAAGUAUACUGCCCUAGAAGUGCUGCACGUUGUGGGGCCC | 83 |
| miR-34-b | GUGCUCGGUUUGUAGGCAGUGUCAUUAGCUGAUUGUACUGUGGUGGUUACAAUCACUAACUCCACUGCCAUCAAAACAAGGCAC | 84 |
| miR-34-c | AGUCUAGUUACUAGGCAGUGUAGUUAGCUGAUUGCUAAUAGUACCAAUCACUAACCACACGGCCAGGUAAAAAGAUU | 85 |
| miR-91-13 | UCAGAAUAAUGUCAAAGUGCUUACAGUGCAGGUAGUGAUAUGUGCAUCUACUGCAGUGAAGGCACUUGUAGCAUUAUGGUGA | 86 |
| miR-92-1 | CUUUCUACACAGGUUGGGAUCGGUUGCAAUGCUGUGUUUCUGUAUGGUAUUGCACUUGUCCCGGCCUGUUGAGUUUGG | 87 |
| miR-92-2 | UCAUCCCUGGGUGGGGAUUUGUUGCAUUACUUGUGUUCUAUAUAAAGUAUUGCACUUGUCCCGGCCUGUGGAAGA | 88 |
| miR-93-1 (miR-93-2) | CUGGGGGCUCCAAAGUGCUGUUCGUGCAGGUAGUGUGAUUACCCAACCUACUGCUGAGCUAGCACUUCCCGAGCCCCGG | 89 |
| miR-95-4 | AACACAGUGGGCACUCAAUAAAUGUCUGUUGAAUUGAAAUGCGUUACAUUCAACGGGUAUUUAUUGAGCACCCACUCUGUG | 90 |
| miR-96-7 | UGGCCGAUUUUGGCACUAGCACAUUUUUGCUUGUGUCUCUCCGCUCUGAGCAAUCAUGUGCAGUGCCAAUAUGGGAAA | 91 |
| miR-97-6 (miR-30*) | GUGAGCGACUGUAAACAUCCUCGACUGGAAGCUGUGAAGCCACAGAUGGGCUUUCAGUCGGAUGUUUGCAGCUGCCUACU | 92 |
| miR-98 | GUGAGGUAGUAAGUUGUAUUGUUGUGGGGUAGGGAUAUUAGGCCCCAAUUAGAAGAUAACUAUACAACUUACUACUUUCC | 93 |
| miR-99b | GGCACCCACCCGUAGAACCGACCUUGCGGGGCCUUCGCCGCACACAAGCUCGUGUCUGUGGGUCCGUGUC | 94 |
| miR-99a | CCCAUUGGCAUAAACCCGUAGAUCCGAUCUUGUGGUGAAGUGGACCGCACAAGCUCGCUUCUAUGGGUCUGUGUCAGUGUG | 95 |
| miR-100-1/2 | AAGAGAGAAGAUAUUGAGGCCUGUUGCCACAAACCCGUAGAUCCGAACUUGUGGUAUUAGUCCGCACAAGCUUGUAUCUAUAGGUAUGUGUCUGUUAGGCAAUCUCAC | 96 |
| miR-100-11 | CCUGUUGCCACAAACCCGUAGAUCCGAACUUGUGGUAUUAGUCCGCACAAGCUUGUAUCUAUAGGUAUGUGUCUGUUAGG | 97 |
| miR-101-1/2 | AGGCUGCCCUGGCUCAGUUAUCACAGUGCUGAUGCUGUAUUCUAAAGGUACAGUACUGUGAUAACUGAAGGAUGGCCAUCUUACCUUCCAUCAGAGGAGCCUCAC | 98 |
| miR-101 | UCAGUUAUCACAGUGCUGAUGCUGUGCAUUCUAAAGGUACAGUACUGUGAUAACUGA | 99 |
| miR-101-1 | UGCCCUGGCUCAGUUAUCACAGUGCUGAUGCUGUCUAUUCUAAAGGUACAGUACUGUGAUAACUGAAGGAUGGCA | 100 |
| miR-101-2 | ACUGUCCUUUUUCGGUUAUCAUGGUACCGAUGCUGUAUAUCUGAAAGGUACAGUACUGUGAUAACUGAAGAAUGGUGGU | 101 |
| miR-101-9 | UGUCCUUUUUCGGUUAUCAUGGUACCGAUGCUGUAUAUCUGAAAGGUACAGUACUGUGAUAACUGAAGAAUGGUG | 102 |
| miR-102-1 | CUUCUGGAAGCUGGUUUCACAUGGUGGCUUAGAUUUUUCCAUCUUUGUAUCUAGCACCAUUUGAAAUCAGUGUUUUAGGAG | 103 |
| miR-102-7.1 (miR-102-7.2) | CUUCAGGAAGCUGGUUUCAUAUGGUGGUUUAGAUUUAAAUAUGAUUUGUCUAGCACCAUUUGAAAUCAGUGUUCUUGGGGG | 104 |
| miR-103-2 | UUGUGCUUUCAGCUUCUUUACAGUGCUGCCUUGUAGCAUUCAGGUCAAGCAACAUUGUACAGGGCUAUGAAAGAACCA | 105 |
| miR-103-1 | UACUGCCCUCGGCUUCUUUACAGUGCUGCCUUGUUGCAUAUGGAUCAAGCAGCAUUGUACAGGGCUAUGAAGGCAUUG | 106 |
| miR-104-17 | AAAUGUCAGACAGCCCAUCGACUGGUGUUGCCAUGAGAUUCAACAGUCAACAUCAGUCUGAUAAGCUACCCGACAAGG | 107 |
| miR-105-1 | UGUGCAUCGUGGUCAAAUGCUCAGACUCCUGUGGGGUCUGCUCAUGCACCACGGAUGUUUGAGCAUGUGCUACGUGUCUA | 108 |
| miR-105-2 | UGUGCAUCGUGGUCAAAUGCUCAGACUCCUGUGGGGUCUGCUUAUGCACCACGGAUGUUUGAGCAUGUGCUAUGGUGUCUA | 109 |
| miR-106-a | CCUUGGCCAUGUAAAAGUGCUUACAGUGCAGGUAGCUUUUUGAGAUCUACUGCAAUGUAAGCACUUCUUACAUUACCAUGG | 110 |
| miR-106-b | CCUGCCGGGGCUAAAGUGCUGACAGUGCAGAUAGUGGUCCUCUCCGUGCUACCGCACUGUGGGUACUUGCUGCCAGCAGG | 111 |
| miR-107 | CUCUCUGCUUUCAGCUUCUUUACAGUGUUGCCUUGUGGCAUGGAGUUCAAGCAGCAUUGUACAGGGCUAUCAAAGCACAGA | 112 |
| miR-108-1-small | ACACUGCAAGAACAAUAAGGAUUUUUAGGGGCAUUAUGACUGAGUCAAGAAAACAGCUGCCCCUGAAAGUCCCUCAUUUUUCUUGCUGU | 113 |
| miR-108-2-small | ACUGCAAGAGCAAUAAGGAUUUUUAGGGGCAUUAUGAUAGUGGAAUGGAAACACAUCUGCCCCCAAAAGUCCCUCAUUUU | 114 |
| miR-122a-1 | CCUUAGCAGAGCUGUGGAGUGUGACAAUGGUGUUUGUGUCUAAACUAUCAAACGCCAUUAUCACACUAAAUAGCUACUGCUAGGC | 115 |
| miR-122a-2 | AGCUGUGGAGUGUGACAAUGGUGUUUGUGUCCAAACUAUCAAACGCCAUUAUCACACUAAAUAGCU | 116 |
| miR-123 | ACAUUAUUACUUUUGGUACGCGCUGUGACACUUCAAACUCGUACCGUGAGUAAUAAUGCGC | 117 |

TABLE 1a-continued

Human microRNA Precursor Sequences.

| Precursor Name | Sequence (5' To 3')* | SEQ ID NO. |
|---|---|---|
| miR-124a-1 | AGGCCUCUCUCUCCGUGUUCACAGCGGACCUU GAUUUAAAUGUCCAUACAAUUAAGGCACGCGG UGAAUGCCAAGAAUGGGGCUG | 118 |
| miR-124a-2 | AUCAAGAUUAGAGGCUCUGCUCUCCGUGUUCA CAGCGGACCUUGAUUUAAUGUCAUACAAUUAA GGCACGCGGUGAAUGCCAAGAGCGGAGCCUAC GGCUGCACUUGAAG | 119 |
| miR-124a-3 | UGAGGGCCCCUCUGCGUGUUCACAGCGGACCU UGAUUUAAUGUCUAUACAAUUAAGGCACGCGG UGAAUGCCAAGAGAGGCGCCUCC | 120 |
| miR-124a | CUCUGCGUGUUCACAGCGGACCUUGAUUUAAU GUCUAUACAAUUAAGGCACGCGGUGAAUGCCA AGAG | 121 |
| miR-124b | CUCUCCGUGUUCACAGCGGACCUUGAUUUAAU GUCAUACAAUUAAGGCACGCGGUGAAUGCCAA GAG | 122 |
| miR-125a-1 | UGCCAGUCUCUAGGUCCCUGAGACCCUUUAAC CUGUGAGGACAUCCAGGGUCACAGGUGAGGUU CUUGGGAGCCUGGCGUCUGGCC | 123 |
| miR-125a-2 | GGUCCCUGAGACCCUUUAACCUGUGAGGACAU CCAGGGUCACAGGUGAGGUUCUUGGGAGCCUG G | 124 |
| miR-125b-1 | UGCGCUCCUCUCAGUCCCUGAGACCCUAACUU GUGAUGUUACCGUUUAAAUCCACGGGUUAGG CUCUUGGGAGCUGCGAGUCGUGCU | 125 |
| miR-125b-2 | ACCAGACUUUUCCUAGUCCCUGAGACCCUAAC UUGUGAGGUAUUUAGUAACAUCACAAGUCAG GCUCUUGGGACCUAGGCGGAGGGGA | 126 |
| miR-126-1 | CGCUGGCGACGGGACAUUAUUACUUUUGGUAC GCGCUGUGACAGUUCAAACUCGUACCGUGAGU AAUAAUGCGCCGUCCACGGCA | 127 |
| miR-126-2 | ACAUUAUUACUUUUGGUACGCGCUGUGACACU UCAAACUCGUACCGUGAGUAAUAAUGCGC | 128 |
| miR-127-1 | UGUGAUCACUGUCUCCAGCCUGCUGAAGCUCA GAGGGCUCUGAUUCAGAAAGAUCAUCGGAUCC GUCUGAGCUUGGCUGGUCGGAAGUCUCAUCAU C | 129 |
| miR-127-2 | CCAGCCUGCUGAAGCUCAGAGGGCUCUGAUUC AGAAAGAUCAUCGGAUCCGUCUGAGCUUGGCU GGUCGG | 130 |
| miR-128a | UGAGCUGUUGGAUUCGGGGCCGUAGCACUGUC UGAGAGGUUUACAUUUCUCACAGUGAACCGGU CUCUUUUUCAGCUGCUUC | 131 |
| miR-128b | GCCCGGCAGCCACUGUGCAGUGGGAAGGGGGG CCGAUACACUGUACGAGAGUGAGUAGCAGGUC UCACAGUGAACCGGUCUCUUUCCCUACUGUGU CACACUCCUAAUGG | 132 |
| miR-128 | GUUGGAUCGGGGCCGUAGCACUGUCUGAGAG GUUUACAUUUCUCACAGUGAACCGGUCUCUUU UUCAGC | 133 |
| miR-129-1 | UGGGCUUUUUGCGGUCUGGGCUUGCUGUUCC UCUCAACAGUAGUCAGGAAGCCCUUACCCCAA AAAGUAUCUA | 134 |
| miR-129-2 | UGCCCUUCGCGAAUCUUUUUGCGGUCUGGGCU UGCUGUACAUAACUCAAUAGCCGGAAGCCCUU ACCCCAAAAAGCAUUUGCGGAGGGCG | 135 |
| miR-130a | UGCUGCUGGCCAGAGCUCUUUUCACAUUGUGC UACUGUCUGCACCUGUCACUAGCAGUGCAAUG UUUAAAGGGCAUUGGCCGUGUAGUG | 136 |
| miR-131-1 | GCCAGGAGGCGGGGUUGGUUGUUAUCUUUGGU UAUCUAGCUGUAUGAGUGGUGUGGAGUCUUCA UAAAGCUAGAUAACCGAAAGUAAAAAUAACCC CAUACACUGCGCAG | 137 |
| miR-131-3 | CACGGCGCGGCAGCGGCACUGGCUAAGGGAGG CCCGUUUCUCUCUUUGGUUAUCUAGCUGUAUG AGUGCCACAGAGCCGUCAUAAAGCUAGAUAAC CGAAAGUAGAAAUG | 138 |
| miR-131 | GUUGUUAUCUUUGGUUAUCUAGCUGUAUGAGU GUAUUGGUCUUCAUAAAGCUAGAUAACCGAAA GUAAAAAC | 139 |
| miR-132-1 | CCGCCCCCGCGUCUCCAGGGCAACCGUGGCUU UCGAUUGUUACUGUGGGAACUGGAGGUAACAG UCUACAGCCAUGGUCGCCCCGCAGCACGCCCA CGCGC | 140 |
| miR-132-2 | GGGCAACCGUGGCUUUCGAUUGUUACUGUGGG AACUGGAGGUAACAGUCUACAGCCAUGGUCGC CC | 141 |
| miR-133a-1 | ACAAUGCUUUGCUAGAGCUGGUAAAAUGGAAC CAAAUCGCCUCUUCAAUGGAUUUGGUCCCCUU CAACCAGCUGUAGCUAUGCAUUGA | 142 |
| miR-133a-2 | GGGAGCCAAAUGCUUUGCUAGAGCUGGUAAAA UGGAACCAAAUCGACUGUCCAAUGGAUUUGGU CCCCUUCAACCAGCUGUAGCUGUGCAUUGAUG GCGCCG | 143 |
| miR-133 | GCUAGAGCUGGUAAAAUGGAACCAAAUCGCCU CUUCAAUGGAUUUGGUCCCCUUCAACCAGCUG UAGC | 144 |
| miR-133b | CCUCAGAAGAAAGAUGCCCCCUGCUCUGGCUG GUCAAACGGAACCAAGUCCGUCUUCCUGAGAG GUUUGGUCCCCUUCAACCAGCUACAGCAGGGC UGGCAAUGCCCAGUCCUUGGAGA | 145 |
| miR-133b-small | GCCCCCUGCUCUGGCUGGUCAAACGGAACCAA GUCCGUCUUCCUGAGAGGUUUGGUCCCCUUCA ACCAGCUACAGCAGGG | 146 |
| miR-134-1 | CAGGGUGUGUGACUGGUUGACCAGAGGGGCAU GCACUGUGUUCACCCUGUGGGCCACCUAGUCA CCAACCCUC | 147 |
| miR-134-2 | AGGGUGUGUGACUGGUUGACCAGAGGGGCAUG CACUGUGUUCACCCUGUGGGCCACCUAGUCAC CAACCCU | 148 |
| miR-135a-1 | AGGCCUCGCUGUUCUCUAUGGCUUUUUAUUCC UAUGUGAUUCUACUGCUCACUCAUAUAGGGAU UGGAGCCGUGGCGCACGGCGGGGACA | 149 |
| miR-135a-2 (miR-135-2) | AGAUAAAUUGACUCUAGUGCUUUAUGGCUUUU UAUUCCUAUGUGAUAGUAAUAAAGUCUCAUGU AGGGAUGGAAGCCAUGAAAUACAUUGUGAAAA AUCA | 150 |
| miR-135 | CUAUGGCUUUUUAUUCCUAUGUGAUUCUACUG CUCACUCAUAUAGGGAUUGGAGCCGUGG | 151 |

TABLE 1a-continued

Human microRNA Precursor Sequences.

| Precursor Name | Sequence (5' To 3')* | SEQ ID NO. |
|---|---|---|
| miR-135b | CACUCUGCUGUGGCCUAUGGCUUUUCAUUCCUAUGUGAUUGCUGUCCCAAACUCAUGUAGGGCUAAAAGCCAUGGGCUACAGUGAGGGGCGAGCUCC | 152 |
| miR-136-1 | UGAGCCCUCGGAGGACUCCAUUUGUUUUGAUGAUGGAUUCUUAUGCUCCAUCAUCGUCUCAAAUGAGUCUUCAGAGGGUUCU | 153 |
| miR-136-2 | GAGGACUCCAUUUGUUUUGAUGAUGGAUUCUUAUGCUCCAUCAUCGUCUCAAAUGAGUCUUC | 154 |
| miR-137 | CUUCGGUGACGGGUAUUCUUGGGUGGAUAAUACGGAUUACGUUGUUAUUGCUUAAGAAUACGCGUAGUCGAGG | 155 |
| miR-138-1 | CCCUGGCAUGGUGUGGUGGGGCAGCUGGUGUUGUGAAUCAGGCCGUUGCCAAUCAGAGAACGGCUACUUCACAACACCAGGGCCACACCACACUACAGG | 156 |
| miR-138-2 | CGUUGCUGCAGCUGGUGUUGUGAAUCAGGCCGACGAGCAGCGCAUCCUCUUACCCGGCUAUUUCACGACACCAGGGUUGCAUCA | 157 |
| miR-138 | CAGCUGGUGUUGUGAAUCAGGCCGACGAGCAGCGCAUCCUCUUACCCGGCUAUUUCACGACACCAGGGUUG | 158 |
| miR-139 | GUGUAUUCUACAGUGCACGUGUCUCCAGUGUGGCUCGGAGGCUGGAGAGGCGGCCCUGUUGGAGUAAC | 159 |
| miR-140 | UGUGUCUCUCUCUGUGUCCUGCCAGUGGUUUUACCCUAUGGUAGGUUACGUCAUGCUGUUCUACCACAGGGUAGAACCACGGACAGGAUACCGGGCACC | 160 |
| miR-140as | UCCUGCCAGUGGUUUUUACCCUAUGGUAGGUUACGUCAUGCUGUUCUACCACAGGGUAGAACCACGGACAGGA | 161 |
| miR-140s | CCUGCCAGUGGUUUUUACCCUAUGGUAGGUUACGUCAUGCUGUUCUACCACAGGGUAGAACCACGGACAGG | 162 |
| miR-141-1 | CGGCCGGCCCUGGGUCCAUCUUCCAGUACAGUGUUGGAUGGUCUAAUUGUGAAGCUCCUAACACUGUCUGGUAAAGAUGGCUCCCGGGUGGGUUC | 163 |
| miR-141-2 | GGGUCCAUCUUCCAGUACAGUGUUGGAUGGUCUAAUUGUGAAGCUCCUAACACUGUCUGGUAAAGAUGGCCC | 164 |
| miR-142 | ACCCAUAAAGUAGAAAGCACUACUAACAGCACUGGAGGGUGUAGUGUUUCCUACUUUAUGGAUG | 165 |
| miR-143-1 | GCGCAGCGCCCUGUCUCCCAGCCUGAGGUGCAGUGCUGCAUCUCUGGUCAGUUGGGAGUCUGAGAUGAAGCACUGUAGCUCAGGAAGAGAGAAGUUGUUCUGCAGC | 166 |
| miR-143-2 | CCUGAGGUGCAGUGCUGCAUCUCUGGUCAGUUGGGAGUCUGAGAUGAAGCACUGUAGCUCAGG | 167 |
| miR-144-1 | UGGGGCCCUGGCUGGGAUAUCAUCAUAUACUGUAAUUUGCGAUGAGACAUACAGUAUAGAUGAUGUACUAGUCCGGGCACCCC | 168 |
| miR-144-2 | GGCUGGAUAUCAUCAUAUACUGUAAGUUUGCGAUGAGACACUACAGUAUAGAUGAUGUACUAGUC | 169 |
| miR-145-1 | CACCUUGUCCUCACGGUCCAGUUUUCCCAGGAAUCCCUUAGAUGCUAAGAUGGGGAUUCCUGGAAAUACUGUUCUUGAGGUCAUGGUU | 170 |
| miR-145-2 | CUCACGGUCCAGUUUUCCCAGGAAUCCCUUAGAUGCUAAGAUGGGGAUUCCUGGAAAUACUGUUCUUGAG | 171 |
| miR-146-1 | CCGAUGUGUAUCCUCAGCUUUGAGAACUGAAUUCCAUGGGUUGUGUCAGUGUCAGACCUCUGAAAUUCAGUUCUUCAGCUGGGAUAUCUCUGUCAUCGU | 172 |
| miR-146-2 | AGCUUUGAGAACUGAAUUCCAUGGGUUGUGUCAGUGUCAGACCUGUGAAAUUCAGUUCUUCAGCU | 173 |
| miR-147 | AAUCUAAAGACAACAUUUCUGCACACACACCAGACUAUGGAAGCCAGUGUGUGGAAAUGCUUCUGCUAGAUU | 174 |
| miR-148a (miR-148) | GAGGCAAAGUUCUGAGACACUCCGACUCUGAGUAUGAUAGAAGUCAGUGCACUACAGAACUUUGUCUC | 175 |
| miR-148b | CAAGCACGAUUAGCAUUUGAGGUGAAGUUCUGUUUAUACACUCAGGCUGUGGCUCUCUGAAAGUCAGUGCAUCACAGAACUUUGUCUCGAAAGCUUUCUA | 176 |
| miR-148b-small | AAGCACGAUUAGCAUUUGAGGUGAAGUUCUGUUAUACACUCAGGCUGUGGCUCUCUGAAAGUCAGUGCAU | 177 |
| miR-149-1 | GCCGGCGCCCGAGCUCUGGCUCCGUGUCUUCACUCCCGUGCUUGUCCGAGGAGGGAGGGAGGGACGGGGGCUGUGCUGGGGCAGCUGGA | 178 |
| miR-149-2 | GCUCUGGCUCCGUGUCUUCACUCCCGUGCUUGUCCGAGGAGGGAGGGAGGGAC | 179 |
| miR-150-1 | CUCCCCAUGGCCCUGUCUCCCAACCCUUGUACCAGUGCUGGGCUCAGACCCUGGUACAGGCCUGGGGGACAGGGACCUGGGGAC | 180 |
| miR-150-2 | CCCUGUCUCCCAACCCUUGUACCAGUGCUGGGCUCAGACCCUGGUACAGGCCUGGGGGACAGGG | 181 |
| miR-151 | UUUCCUGCCCUCGAGGAGCUCACAGUCUAGUAUGUCUCAUCCCCUACUAGACUGAAGCUCCUUGAGGACAGG | 182 |
| miR-151-2 | CCUGUCCUCAAGGAGCUUCAGUCUAGUAGGGGAUGAGACAUACUAGACUGUGAGCUCCUCGAGGGCAGG | 183 |
| miR-152-1 | UGUCCCCCCGGCCCAGGUUCUGUGAUACUCCGACUCGGGCUCUGGAGCAGUCAGUGCAUGACAGAACUUGGGCCCGGAAGGACC | 184 |
| miR-152-2 | GGCCCAGGUUCUGUGAUACACUCCGACUCGGGCUCUGGAGCAGUCAGUGCAUGACAGAACUUGGGCCCCGG | 185 |
| miR-153-1-1 | CUCACAGCUGCCAGUGUCAUUUUUGUGAUCUGCAGCUAGUAUUCUCACUCCAGUUGCAUAGUCACAAAAGUGAUCAUUGGCAGGUGUGGC | 186 |
| miR-153-1-2 | UCUCUCUCUCCCUCACAGCUGCCAGUGUCAUUGUCACAAAAGUGAUCAUUGGCAGGUGUGGCAUUCUGCAUG | 187 |

TABLE 1a-continued

Human microRNA Precursor Sequences.

| Precursor Name | Sequence (5' To 3')* | SEQ ID NO. |
|---|---|---|
| miR-153-2-1 | AGCGGUGGCCAGUGUCAUUUUUGUGAUGUUGC AGCUAGUAAUAUGAGCCCAGUUGCAUAGUCAC AAAAGUGAUCAUUGGAAACUGUG | 188 |
| miR-153-2-2 | CAGUGUCAUUUUUGUGAUGUUGCAGCUAGUAA UAUGAGCCCAGUUGCAUAGUCACAAAAGUGAU CAUUG | 189 |
| miR-154-1 | GUGGUACUUGAAGAUAGGUUUAUCCGUGUUGCC UUCGCUUUAUUUGUGACGAAUCAUACACGGUU GACCUAUUUUUCAGUACCAA | 190 |
| miR-154-2 | GAAGAUAGGUUUAUCCGUGUUGCCUUCGCUUUA UUUGUGACGAAUCAUACACGGUUGACCUAUUUU UU | 191 |
| miR-155 | CUGUUAAUGCUAAUCGUGAUAGGGGUUUUUGC CUCCAACUGACUCCUACAUAUUAGCAUUAACA G | 192 |
| miR-156 = miR-157 = overlap miR-141 | CCUAACACUGUCUGGUAAAGAUGGCUCCCGGG UGGGUUCUCUCGGCAGUAACCUUCAGGGAGCC CUGAAGACCAUGGAGGAC | 193 |
| miR-158-small = miR-192 | GCCGAGACCGAGUGCACAGGGCUCUGACCUAU GAAUUGACAGCCAGUGCUCUCGUCUCCCUCU GGCUGCCAAUUCCAUAGGUCACAGGUAUGUUC GCCUCAAUGCCAGC | 194 |
| miR-159-1-small | UCCCGCCCCCUGUAACAGCAACUCCAUGUGGA AGUGCCCACUGGUUCCAGUGGGGCUGCUGUUA UCUGGGGCGAGGGCGA | 195 |
| miR-161-small | AAAGCUGGGUUGAGAGGGCGAAAAAGGAUGAG GUGACUGGUCUGGGCUACGCUAUGCUGCGGCG CUCGGG | 196 |
| miR-163-1b-small | CAUUGGCCUCCUAAGCCAGGGAUUGUGGGUUC GAGUCCCACCCGGGGUAAAGAAAGGCCGAAUU | 197 |
| miR-163-3-small | CCUAAGCCAGGGAUUGUGGGUUCGAGUCCCAC CUGGGGUAGAGGUGAAAGUUCCUUUUACGGAA UUUUUU | 198 |
| miR-162 | CAAUGUCAGCAGUGCCUUAGCAGCACGUAAAU AUUGGCGUUAAGAUUCUAAAAUUAUCUCCAGU AUUAACUGUGCUGCUGAAGUAAGGUUGACCAU ACUCUACAGUUG | 199 |
| miR-175-small = miR-224 | GGGCUUUCAAGUCACUAGUGGUUCCGUUUAGU AGAUGAUUGUGCAUUGUUUCAAAAUGGUGCCC UAGUGACUACAAAGCCC | 200 |
| miR-177-small | ACGCAAGUGUCCUAAGGUGAGCUCAGGGAGCA CAGAAACCUCCAGUGGAACAGAAGGGCAAAAG CUCAUU | 201 |
| miR-180-small | CAUGUGUCACUUUCAGGUGGAGUUUCAAGAGU CCCUUCCUGGUUCACCGUCUCCUUUGCUCUU CACAAC | 202 |
| miR-181a | AGAAGGGCUAUCAGGCCAGCCUUCAGAGGACU CCAAGGAACAUUCAACGCUGUCGGUGAGUUUG GGAUUUGAAAAAACCACUGACCGUUGACUGUA CCUUGGGGUCCUUA | 203 |
| miR-181b-1 | CCUGUGCAGAGAUUAUUUUUUAAAAGGUCACA AUCAACAUUCAUUGCUGUCGGUGGGUUGAACU GUGUGGACAAGCUCACUGAACAAUGAAUGCAA CUGUGGCCCCGCUU | 204 |
| miR-181b-2 | CUGAUGGCUGCACUCAACAUUCAUUGCUGUCG GUGGGUUUGAGUCUGAAUCAACUCACUGAUCA AUGAAUGCAAACUGCGGACCAAACA | 205 |
| miR-181c | CGGAAAAUUUGCCAAGGGUUUGGGGGAACAUU CAACCUGUCGGUGAGUUUGGGCAGCUCAGGCA AACCAUCGACCGUUGAGUGGACCCUGAGGCCU GGAAUUGCCAUCCU | 206 |
| miR-182-as | GAGCUGCUUGCCUCCCCCGUUUUUGGCAAUG GUAGAACUCACACUGGUGAGGUAACAGGAUCC GGUGGUUCUAGACUUGCCAACUAUGGGGCGAG GACUCAGGCGGCAC | 207 |
| miR-182 | UUUUUGGCAAUGGUAGAACUCACACUGGUGAG GUAGAACAGGAUCCGGUGGUUCUAGACUUGCCAA CUAUGG | 208 |
| miR-183 | CCGCAGAGUGUGACUCCUGUUCUGUGUAUGGC ACUGGUAGAAUUCACUGUGAACAGUCUCAGUC AGUGAAUUACCGAAGGGCCAUAAACAGAGCAG AGACAGAUCCACGA | 209 |
| miR-184-1 | CCAGUCACGUCCCCUUAUCACUUUUCCAGCCC AGCUUUGUGACUGUAAGUGUUGGACGGAGAAC UGAUAAGGGUAGGUGAUUGA | 210 |
| miR-184-2 | CCUUAUCACUUUUCCAGCCCAGCUUUGUGACU GUAAGUGUUGGACGGAGAACUGAUAAGGGUAG G | 211 |
| miR-185-1 | AGGGGGCGAGGGAUUGGAGAGAAAGGCAGUUC CUGAUGGUCCCCUCCCCAGGGGCUGGCUUUCC UCUGGUCCUUCCCUCCCA | 212 |
| miR-185-2 | AGGGAUUGGAGAGAAAGGCAGUUCCUGAUGGU CCCCUCCCCAGGGGCUGGCUUUCCUCUGGUCC UU | 213 |
| miR-186-1 | UGCUUGUAACUUUCCAAAGAAUUCUCCUUUUG GCUUUCUGGUUUUAUUUUAAGCCCAAAGGUG AAUUUUUUGGGAAGUUUGAGCU | 214 |
| miR-186-2 | ACUUUCCAAAGAAUUCUCCUUUGGGCUUUCU GGUUUUAUUUUAAGCCCAAAGGUGAAUUUUUU GGGAAGU | 215 |
| miR-187 | GGUCGGGCUCACCAUGACACAGUGUGAGACUC GGGCUACAACACAGGACCCGGGGCGCUGCUCU GACCCCUCGUGUCUUGUGUUGCAGCCGGAGGG ACGCAGGUCCGCA | 216 |
| miR-188-1 | UGCUCCCUCUCUCACAUCCCUUGCAUGGUGGA GGGUGAGCUUUCUGAAAACCCCUCCCCACAUGC AGGGUUUGCAGGAUGGCGAGCC | 217 |
| miR-188-2 | UCUCACAUCCCUUGCAUGGUGGAGGGUGAGCU UUCUGAAAACCCCUCCCACAUGCAGGGUUUGC AGGA | 218 |
| miR-189-1 | CUGUCGAUUGGACCCGCCCUCCGGUGCCUACU GAGCUGAUAUCAGUUCUCAUUUUACACACUGG CUCAGUUCAGCAGGAACAGGAGUCGAGCCCUU GAGCAA | 219 |
| miR-189-2 | CUCCGGUGCCUACUGAGCUGAUAUCAGUUCUC AUUUUACACACUGGCUCAGUUCAGCAGGAACA GGAG | 220 |
| miR-190-1 | UGCAGGCCUCUGUGUGAUAUGUUUGAUAUAUU AGGUUGUUAUUUAAUCCAACUAUAUAUCAAAC AUAUUCCUACAGUGUCUUGCC | 221 |

TABLE 1a-continued

Human microRNA Precursor Sequences.

| Precursor Name | Sequence (5' To 3')* | SEQ ID NO. |
|---|---|---|
| miR-190-2 | CUGUGUGAUAUGUUUGAUAUAUUAGGUUGUUA UUUAAUCCAACUAUAUAUCAAACAUAUUCCUA CAG | 222 |
| miR-191-1 | CGGCUGGACAGCGGGCAACGGAAUCCCAAAAG CAGCUGUUGUCUCCAGAGCAUUCCAGCUGCGC UUGGAUUUCGUCCCCUGCUCUCCUGCCU | 223 |
| miR-191-2 | AGCGGGCAACGGAAUCCCAAAAGCAGCUGUUG UCUCCAGAGCAUUCCAGCUGCGCUUGGAUUUC GUCCCCUGCU | 224 |
| miR-192-2/3 | CCGAGACCGAGUGCACAGGGCUCUGACCUAUG AAUUGACAGCCAGUGCUCUCGUCUCCCCUCUG GCUGCCAAUUCCAUAGGUCACAGGUAUGUUCG CCUCAAUGCCAG | 225 |
| miR-192 | GCCGAGACCGAGUGCACAGGGCUCUGACCUAU GAAUUGACAGCCAGUGCUCUCGUCUCCCCUCU GGCUGCCAAUUCCAUAGGUCACAGGUAUGUUC GCCUCAAUGCCAGC | 226 |
| miR-193-1 | CGAGGAUGGGAGCUGAGGGCUGGGUCUUUGCG GGCGAGAUGAGGGUGUCGGAUCAACUGGCCUA CAAAGUCCCAGUUCUCGGCCCCCG | 227 |
| miR-193-2 | GCUGGGUCUUUGCGGGCGAGAUGAGGGUGUCG GAUCAACUGGCCUACAAAGUCCCAGU | 228 |
| miR-194-1 | AUGGUGUUAUCAAGUGUAACAGCAACUCCAUG UGGACUGUGUACCAAUUUCCAGUGGAGAUGCU GUUACUUUUGAUGGUUACCAA | 229 |
| miR-194-2 | GUGUAACAGCAACUCCAUGUGGACUGUGUACC AAUUUCCAGUGGAGAUGCUGUUACUUUUGAU | 230 |
| miR-195-1 | AGCUUCCCUGGCUCUAGCAGCACAGAAAUAUU GGCACAGGGAAGCGAGUCUGCCAAUAUUGGCU GUGCUGCUCCAGGCAGGGUGGUG | 231 |
| miR-195-2 | UAGCAGCACAGAAAUAUUGGCACAGGGAAGCG AGUCUGCCAAUAUUGGCUGUGCUGCU | 232 |
| miR-196-1 | CUAGAGCUUGAAUGGAACUGCUGAGUGAAUU AGGUAGUUUCAUGUUGUUGGGCCUGGGUUUCU GAACACAACAACAUUAAACCACCCGAUUCACG GCAGUUACUGCUCC | 233 |
| miR-196a-1 | GUGAAUUAGGUAGUUUCAUGUUGUUGGGCCUG GGUUUCUGAACACAACAACAUUAAACCACCCG AUUCAC | 234 |
| miR-196a-2 (miR-196-2) | UGCUCGCUCAGCUGAUCUGUGGCUUAGGUAGU UUCAUGUUGUUGGGAUUGAGUUUUGAACUCGG CAACAAGAAACUGCCUGAGUUACAUCAGUCGG UUUUCGUCGAGGGC | 235 |
| miR-196 | GUGAAUUAGGUAGUUUCAUGUUGUUGGGCCUG GGUUUCUGAACACAACAACAUUAAACCACCCG AUUCAC | 236 |
| miR-196b | ACUGGUCGGUGAUUUAGGUAGUUUCCUGUUGU UGGGAUCCACCUUUCUCUCGACAGCACGACAC UGCCUUCAUUACUUCAGUUG | 237 |
| miR-197 | GGCUGUGCCGGGUAGAGAGGGCAGUGGGAGGU AAGAGCUCUUCACCCUUCACCACCUUCUCCAC CCAGCAUGGCC | 238 |
| miR-197-2 | GUGCAUGUGUAUGUAUGUGUGCAUGUGCAUGU GUAUGUGUAUGAGUGCAUGCGUGUGUGC | 239 |
| miR-198 | UCAUUGGUCCAGAGGGGAGAUAGGUUCCUGUG AUUUUUCCUUCUUCUCUAUAGAAUAAAUGA | 240 |
| miR-199a-1 | GCCAACCCAGUGUUCAGACUACCUGUUCAGGA GGCUCUCAAUGUGUACAGUAGUCUGCACAUUG GUUAGGC | 241 |
| miR-199a-2 | AGGAAGCUUCUGGAGAUCCUGCUCCGUCGCCC CAGUGUUCAGACUACCUGUUCAGGACAAUGCC GUUGUACAGUAGUCUGCACAUUGGUUAGACUG GGCAAGGGAGAGCA | 242 |
| miR-199b | CCAGAGGACACCUCCACUCCGUCUACCCAGUG UUUAGACUAUCUGUUCAGGACUCCCAAAUUGU ACAGUAGUCUGCACAUUGGUUAGGCUGGGCUG GGUUAGACCCUCGG | 243 |
| miR-199s | GCCAACCCAGUGUUCAGACUACCUGUUCAGGA GGCUCUCAAUGUGUACAGUAGUCUGCACAUUG GUUAGGC | 244 |
| miR-200a | GCCGUGGCCAUCUUACUGGGCAGCAUUGGAUG GAGUCAGGUCUCUAAUACUGCCUGGUAAUGAU GACGGC | 245 |
| miR-200b | CCAGCUCGGGCAGCCGUGGCCAUCUUACUGGG CAGCAUUGGAUGGAGUCAGGUCUCUAAUACUG CCUGGUAAUGAUGACGGCGGAGCCCUGCACG | 246 |
| miR-200c | CCCUCGUCUUACCCAGCAGUGUUUGGGUGCGG UUGGGAGUCUCUAAUACUGCCGGGUAAUGAUG GAGG | 247 |
| miR-202 | GUUCCUUUUUCCUAUGCAUAUACUUCUUUGAG GAUCUGGCCUAAAGAGGUAUAGGGCAUGGGAA GAUGGAGC | 248 |
| miR-203 | GUGUUGGGGACUCGCGCGCUGGGUCCAGUGGU UCUUAACAGUUCAACAGUUCUGUAGCGCAAUU GUGAAAUGUUUAGGACCACUAGACCCGGCGGG CGCGGCGACAGCGA | 249 |
| miR-204 | GGCUACAGUCUUUCUUCAUGUGACUCGUGGAC UUCCCUUUGUCAUCCUAUGCCUGAGAAUAUAU GAAGGAGGCUGGGAAGGCAAAGGGACGUUCAA UUGUCAUCACUGGC | 250 |
| miR-205 | AAAGAUCCUCAGACAAUCCAUGUGCUUCUCUU GUCCUUCAUUCCACCGGAGUCUGUCUCAUACC CAACCAGAUUUCAGUGGAGUGAAGUUCAGGAG GCAUGGAGCUGACA | 251 |
| miR-206-1 | UGCUUCCCGAGGCCACAUGCUUCUUUAUAUCC CCAUAUGGAUUACUUUGCUAUGGAAUGUAAGG AAGUGUGUGGUUUCGGCAAGUG | 252 |
| miR-206-2 | AGGCCACAUGCUUCUUUAUAUCCCCAUAUGGA UUACUUUGCUAUGGAAUGUAAGGAAGUGUGUG GUUUU | 253 |
| miR-208 | UGACGGGCGAGCUUUUGGCCCGGGUUAUACCU GAUGCUCACGUAUAAGACGAGCAAAAAGCUUG UUGGUCA | 254 |
| miR-210 | ACCCGGCAGUGCCUCCAGGCGCAGGGCAGCCC CUGCCCACCGCACACUGCGCUGCCCCAGACCC ACUGUGCGUGUGACAGCGGCUGAUCUGUGCCU GGGCAGCGCGACCC | 255 |
| miR-211 | UCACCUGGCCAUGUGACUUGUGGGCUUCCCUU UGUCAUCCUUCGCCUAGGGCUCUGAGCAGGGC AGGGACAGCAAAGGGGUGCUCAGUUGUCACUU CCCACAGCACGGAG | 256 |

TABLE 1a-continued

Human microRNA Precursor Sequences.

| Precursor Name | Sequence (5' To 3')* | SEQ ID NO. |
|---|---|---|
| miR-212 | CGGGGCACCCCGCCCGGACAGCGCGCCGGCACCUUGGCUCUAGACUGCUUACUGCCCGGGCCGCCCUCAGUAACAGUCUCCAGUCACGGCCACCGACGCCUGGCCCCGCC | 257 |
| miR-213-2 | CCUGUGCAGAGAUUAUUUUUUAAAAGGUCACAAUCAACAUUCAUUGCUGUCGGUGGGUUGAACUGUGUGGACAAGCUCACUGAACAAUGAAUGCAACUGUGGCCCCGCUU | 258 |
| miR-213 | GAGUUUUGAGGUUGCUUCAGUGAACAUUCAACGCUGUCGGUGAGUUUGGAAUUAAAAUCAAAACCAUCGACCGUUGAUUGUACCCUAUGGCUAACCAUCAUCUACUCC | 259 |
| miR-214 | GGCCUGGCUGGACAGAGUUGUCAUGUGUCUGCCUGUCUACACUUGCUGUGCAGAACAUCCGCUCACCUGUACAGCAGGCACAGACAGGCAGUCACAUGACAACCCAGCCU | 260 |
| miR-215 | AUCAUUCAGAAAUGGUAUACAGGAAAAUGACCUAUGAAUUGACAGACAAUAUAGCUGAGUUUGUCUGUCAUUUCUUUAGGCCAAUAUUCUGUAUGACUGUGCUACUUCAA | 261 |
| miR-216 | GAUGGCUGUGAGUUGGCUUAAUCUCAGCUGGCAACUGUGAGAUGUUCAUACAAUCCCUCACAGUGGUCUCUGGGAUUAUGCUAAACAGAGCAAUUUCCUAGCCCUCACGA | 262 |
| miR-217 | AGUAUAAUUAUUACUAGUUUUUGAUGUCGCAGAUACUGCAUCAGGAACUGAUUGGAUAAGAAUCAGUCACCAUCAGUUCCUAAUGCAUUGCCUUCAGCAUCUAAACAAG | 263 |
| miR-218-1 | GUGAUAAUGUAGCGAGAUUUUCUGUUGUGCUUGAUCUAACCAUGUGGUUGCGAGGUAUGAGUAAAACAUGGUUCCGUCAAGCACCAUGGAACGUCACGCAGCUUUCUACA | 264 |
| miR-218-2 | GACCAGUCGCUGCGGGGCUUUCCUUUGUGCUUGAUCUAACCAUGUGGUGGAACGAUGGAAACGGAACAUGGUUCUGUCAAGCACCGCGGAAAGCACCGUGCUCUCCUGCA | 265 |
| miR-219 | CCGCCCCGGGCCGCGGCUCCUGAUUGUCCAAACGCAAUUCUCGAGUCUAUGGCUCCGGCCGAGAGUUGAGUCUGGACGUCCCGAGCCGCCGCCCCCAAACCUCGAGCGGG | 266 |
| miR-219-1 | CCGCCCCGGGCCGCGGCUCCUGAUUGUCCAAACGCAAUUCUCGAGUCUAUGGCUCCGGCCGAGAGUUGAGUCUGGACGUCCCGAGCCGCCGCCCCCAAACCUCGAGCGGG | 267 |
| miR-219-2 | ACUCAGGGCUUCGCCACUGAUUGUCCAAACGCAAUUCUUGUACGAGUCUGCGGCCAACCGAGAAUUGUGGCUGGACAUCUGUGGCUGAGCUCCGGG | 268 |
| miR-220 | GACAGUGUGGCAUUGUAGGGCUCCACACCGUAUCUGACACUUUGGGCGAGGGCACCAUGCUGAAGGGUUCAUGAUGCGGUCUGGGAACUCCUCACGGAUCUUACUGAUG | 269 |
| miR-221 | UGAACAUCCAGGUCUGGGGCAUGAACCUGGCAUACAAUGUAGAUUUCUGUGUUCGUUAGGCAACAGCUACAUUGUCUGCUGGGUUUCAGGCUACCUGGAAACAUGUUCUC | 270 |
| miR-222 | GCUGCUGGAAGGUGUAGGUACCCUCAAUGGCUCAGUAGCCAGUGUAGAUCCUGUCUUUCGUAAU | 271 |
| miR-223 | CAGCAGCUACAUCUGGCUACUGGGUCUCUGAUGGCAUCUUCUAGCUCCUGGCCUCCUGCAGUGCCACGCUCCGUGUAUUUGACAAGCUGAGUUGGACACUCCAUGUGGUAGAGUGUCAGUUUGUCAAAUACCCCAAGUGCGGCACAUGCUUACCAG | 272 |
| miR-224 | GGGCUUUCAAGUCACUAGUGGUUCCGUUUAGUAGAUGAUUGUGCAUUGUUUCAAAAUGGUGCCCUAGUGACUACAAAGCCC | 273 |
| miR-294-1 (chr16) | CAAUCUUCCUUUAUCAUGGUAUUGAUUUUUCAGUGCUUCCCUUUUGUGUGAGAGAAGAUA | 274 |
| miR-296 | AGGACCCUUCCAGAGGGCCCCCCCUCAAUCCUGUUGUGCCUAAUUCAGAGGGUUGGGUGGAGGCUCUCCUGAAGGGCUCU | 275 |
| miR-299 | AAGAAAUGGUUUACCGUCCCACAUACAUUUGAAUAUGUAUGUGGGAUGGUAAACCGCUUCUU | 276 |
| miR-301 | ACUGCUAACGAAUGCUCUGACUUUAUUGCACUACUGUACUUUACAGCUAGCAGUGCAAUAGUAUGUCAAAGCAUCUGAAAGCAGG | 277 |
| miR-302a | CCACCACUUAAACGUGGAUGUACUUGCUUUGAAACUAAAGAAGUAAGUGCUUCCAUGUUUUGGUGAUGG | 278 |
| miR-302b | GCUCCCUUCAACUUUAACAUGGAAGUGCUUUCUGUGACUUUAAAAGUAAGUGCUUCCAUGUUUUAGUAGGAGU | 279 |
| miR-302c | CCUUUGCUUUAACAUGGGGGUACCUGCUGUGUGAAACAAAAGUAAGUGCUUCCAUGUUUCAGUGGAGG | 280 |
| miR-302d | CCUCUACUUUAACAUGGAGGCACUUGCUGUGACAUGACAAAAAUAAGUGCUUCCAUGUUUGAGUGUGG | 281 |
| miR-320 | GCUUCGCUCCCCUCCGCCUUCUCUUCCCGGUUCUUCCCGGAGUCGGGAAAAGCUGGGUUGAGAGGGCGAAAAAGGAUGAGGU | 282 |
| miR-321 | UUGGCUCCUAAGCCAGGGAUUGUGGGUUCGAGUCCCACCCGGGGUAAAGAAAGGCCGA | 283 |
| miR-323 | UUGGUACUUGGAGAGAGGUGGUCCGUGGCGCGUUCGCUUUAUUUAUGGCGCACAUUACACGGUCGACCUCUUUGCAGUAUCUAAUC | 284 |
| miR-324 | CUGACUAUGCCUCCCCGCAUCCCCUAGGGCAUUGGUGUAAAGCUGGAGACCCACUGCCCCAGGUGCUGCUGGGGUUGUAGUC | 285 |
| miR-325 | AUACAGUGCUUGGUUCCUAGUAGGUGUCCAGUAAGUGUUUGUGACAUAAUUUGUUUAUUGAGGACCUCCUAUCAAUCAAGCACGUGCUAGGCUCUGG | 286 |
| miR-326 | CUCAUCUGUCUGUUGGGCUGGAGGCAGGGCCUUUGUGAAGGCGGGUGGUGCUCAGAUCGCCUCUGGGCCCUUCCUCCAGCCCCGAGGCGGAUUCA | 287 |
| miR-328 | UGGAGUGGGGGGGCAGGAGGGGCUCAGGGAGAAGUGCAUACAGCCCCUGGCCCUCUCUGCCCUUCCGUCCCCUG | 288 |
| miR-330 | CUUUGGCGAUCACUGCCUCUCUGGGCCUGUGCUUAGGCUCUGCAAGAUCAACCGAGCAAAGCACACGGCCUGCAGAGAGGCAGCGCUCUGCCC | 289 |

TABLE 1a-continued

Human microRNA Precursor Sequences.

| Precursor Name | Sequence (5' To 3')* | SEQ ID NO. |
|---|---|---|
| miR-331 | GAGUUUGGUUUUGUUUGGGUUUGUUCUAGGUA UGGUCCCAGGGAUCCCAGAUCAAACCAGG<u>CCC CUGGGCCUAUCCUAGAA</u>CCAACCUAAGCUC | 290 |
| miR-335 | UGUUUUGAGCGGGGG<u>UCAAGAGCAAUAACGAA AAAUGUUUGUCAUAAACCGUUUUUCAUUAUUG</u> CUCCUGACCUCCUCUCAUUUGCUAUAUUCA | 291 |
| miR-337 | GUAGUCAGUAGUUGGGGGUGGGAACGGCUUC AUAGAGGAGUUGAUGCACAGUUA<u>UCCAGCUCC UAUAUGAUGCCUUU</u>CUUCAUCCCCUUCAA | 292 |
| miR-338 | UCUCCAACAAUAUCCUGGUGCUGAGUGAUGAC UCAGGCGAC<u>UCCAGCAUCAGUGAUUUUGUUGA</u> AGA | 293 |
| miR-339 | CGGGGCGGCCGCUCU<u>CCCUGUCCUCCAGGAGC UCA</u>CGUGUGCCUGCCUGUGAGCGCCUCGACGA CAGAGCCGGCGCCUGCCCCAGUGUCUGCGC | 294 |
| miR-340 | UUGUACCUGGUGUGAUUAUAAAGCAAUGAGAC UGAUUGUCAUAUGUCGUUUGUGGGA<u>UCCGUCU CAGUUACUUUAUAGCC</u>AUACCUGGUAUCUUA | 295 |
| miR-342 | GAAACUGGGCUCAAGGUGAGGGGUGCUAUCUG UGAUUGAGGGACAUGGUUAAUGGAAUUG<u>UCUC ACACAGAAAUCGCACCCGU</u>CACCUUGGCCUAC UUA | 296 |
| miR-345 | ACCCAAACCCUAGGUC<u>UGCUGACUCCUAGUCC AGGGC</u>UCGUGAUGGCUGGUGGGCCCUGAACGA GGGGUCUGGAGGCCUGGGUUUGAAUAUCGACA GC | 297 |
| miR-346 | GUC<u>UGUCUGCCCGCAUGCCUGCCUCUCU</u>GUUG CUCUGAAGGAGGCAGGGGCUGGGCCUGCAGCU GCCUGGGCAGAGCGGCUCCUGC | 298 |
| miR-367 | CCAUUACUGUUGCUAAUAUGCAACUCUGUUGA AUAUAAAUUGGAAUUGCACUUUAGCAAUGGUG AUGG | 299 |
| miR-368 | AAAAGGUGGAUAUUCCUUCUAUGUUUAUGUUA UUUAUGGUUAA<u>ACAUAGAGGAAAUUCCACGUU UU</u> | 300 |
| miR-369 | UUGAAGGGAGAUCGACCGUGUUAUAUUCGCUU UAUUGACUUC<u>GAAUAAUACAUGGUUGAUCUUU</u> UCUCAG | 301 |
| miR-370 | AGACAGAGAAGCCAGGUCACGUCUCUGCAGUU ACACAGCUCACGAGU<u>GCCUGCUGGGGUGGAAC CUGG</u>UCUGUCU | 302 |
| miR-371 | GUGGCACUCAAACUGUGGGGGCACUUUCUGCU CUCUGGUGAAA<u>GUGCCGCCAUCUUUUGAGUGU</u> UAC | 303 |
| miR-372 | GUGGGCCUCAAAUGUGGAGCACUAUUCUGAUG UCCAAGUGG<u>AAAGUGCUGCGACAUUUGAGCGU</u> CAC | 304 |
| miR-373 | GGGAUACUCAAAAUGGGGGCGCUUUCCUUUUU GUCUGUACUGGGAAGUGCUUCGAUUUUGGGGU GUCCC | 305 |
| miR-374 | UACAUCGGCC<u>AUUAUAAUACAACCUGAUAAGU GUUAUAGCA</u>CUUAUCAGAUUGUAUUGUAAUUG UCUGUGUA | 306 |
| miR-hes1 | AUGGAGCUGCUCACCCUGUGGGCCUCAAAUGU GGAGGAACUAUUCUGAUGUCCAAGUGGAAAGU GCUGCGACAUUUGAGCGUGACCGUGACGCCC AUAUCA | 307 |
| miR-hes2 | GCAUCCCCUCAGCCUGUGGCACUCAAACUGUG GGGGCACUUUCUGCUCUCUGGUGAAAGUGCCG CCAUCUUUUGAGUGUUACCGCUUGAGAAGACU CAACC | 308 |
| miR-hes3 | CGAGGAGCUCAUACUGGGAUACUCAAAAUGGG GGCGCUUUCCUUUUUGUCUGUUACUGGGAAGU GCUUCGAUUUUGGGGUGUCCCUGUUUGAGUAG GGCAUC | 309 |

*An underlined sequence within a precursor sequence corresponds to a mature processed miR transcript (see Table 1b). Some precursor sequences have two underlined sequences denoting two different mature miRs that are derived from the same precursor. All sequences are human.

TABLE 1b

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| let-7a | ugagguaguagguuguauaguu | 310 | let-7a-1; let-7a-2; let-7a-3; let-7a-4 |
| let-7b | ugagguaguagguugugugguu | 311 | let-7b |
| let-7c | ugagguaguagguuguaugguu | 312 | let-7c |
| let-7d | agagguaguagguugcauagu | 313 | let-7d; let-7d-v1 |
| let-7e | ugagguaggagguuguauagu | 314 | let-7e |
| let-7f | ugagguaguagauuguauaguu | 315 | let-7f-1; let-7f-2-1; let-7f-2-2 |
| let-7g | ugagguaguaguuuguacagu | 316 | let-7g |

TABLE 1b-continued

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| let-7i | ugagguaguaguuugugcu | 317 | let-7i |
| miR-1 | uggaauguaaagaaguaugua | 318 | miR-1b; miR-1b-1; miR-1b-2 |
| miR-7 | uggaagacuagugauuuuguu | 319 | miR-7-1; miR-7-1a; miR-7-2; miR-7-3 |
| miR-9 | ucuuugguuaucuagcuguauga | 320 | miR-9-1; miR-9-2; miR-9-3 |
| miR-9* | uaaagcuagauaaccgaaagu | 321 | miR-9-1; miR-9-2; miR-9-3 |
| miR-10a | uacccuguagauccgaauuugug | 322 | miR-10a |
| miR-10b | uacccuguagaaccgaauuugu | 323 | miR-10b |
| miR-15a | uagcagcacauaaugguuugug | 324 | miR-15a; miR-15a-2 |
| miR-15b | uagcagcacaucaugguuuaca | 325 | miR-15b |
| miR-16 | uagcagcacguaaauauuggcg | 326 | miR-16-1; miR-16-2; miR-16-13 |
| miR-17-5p | caaagugcuuacagugcagguagu | 327 | miR-17 |
| miR-17-3p | acugcagugaaggcacuugu | 328 | miR-17 |
| miR-18 | uaaggugcaucuagugcagaua | 329 | miR-18; miR-18-13 |
| miR-19a | ugugcaaaucuaugcaaaacuga | 330 | miR-19a; miR-19a-13 |
| miR-19b | ugugcaaauccaugcaaaacuga | 331 | miR-19b-1; miR-19b-2 |
| miR-20 | uaaagugcuuauagugcaggua | 332 | miR-20 (miR-20a) |
| miR-21 | uagcuuaucagacugauguuga | 333 | miR-21; miR-21-17 |
| miR-22 | aagcugccaguugaagaacugu | 334 | miR-22 |
| miR-23a | aucacauugccagggauuucc | 335 | miR-23a |
| miR-23b | aucacauugccagggauuaccac | 336 | miR-23b |
| miR-24 | uggcucaguucagcaggaacag | 337 | miR-24-1; miR-24-2; miR-24-19; miR-24-9 |
| miR-25 | cauugcacuugucucggucuga | 338 | miR-25 |
| miR-26a | uucaaguaauccaggauaggcu | 339 | miR-26a; miR-26a-1; miR-26a-2 |
| miR-26b | uucaaguaauucaggauaggu | 340 | miR-26b |
| miR-27a | uucacaguggcuaaguuccgcc | 341 | miR-27a |
| miR-27b | uucacaguggcuaaguucug | 342 | miR-27b-1; miR-27b-2 |
| miR-28 | aaggagcucacagucuauugag | 343 | miR-28 |
| miR-29a | cuagcaccaucugaaaucgguu | 344 | miR-29a-2; miR-29a |
| miR-29b | uagcaccauuugaaaucagu | 345 | miR-29b-1; miR-29b-2 |
| miR-29c | uagcaccauuugaaaucgguua | 346 | miR-29c |
| miR-30a-5p | uguaaacauccucgacuggaagc | 347 | miR-30a |
| miR-30a-3p | cuuucagucggauguuugcagc | 348 | miR-30a |
| miR-30b | uguaaacauccuacacucagc | 349 | miR-30b-1; miR-30b-2 |

TABLE 1b-continued

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| miR-30c | uguaaacauccuacacucucagc | 350 | miR-30c |
| miR-30d | uguaaacauccccgacuggaag | 351 | miR-30d |
| miR-30e | uguaaacauccuugacugga | 352 | miR-30e |
| miR-31 | ggcaagaugcuggcauagcug | 353 | miR-31 |
| miR-32 | uauugcacauuacuaaguugc | 354 | miR-32 |
| miR-33 | gugcauuguaguugcauug | 355 | miR-33; miR-33b |
| miR-34a | uggcagugucuuagcugguugu | 356 | miR-34a |
| miR-34b | aggcagugucauuagcugauug | 357 | miR-34b |
| miR-34c | aggcaguguaguuagcugauug | 358 | miR-34c |
| miR-92 | uauugcacuugucccggccugu | 359 | miR-92-2; miR-92-1 |
| miR-93 | aaagugcuguucgugcagguag | 360 | miR-93-1; miR-93-2 |
| miR-95 | uucaacggguauuuauugagca | 361 | miR-95 |
| miR-96 | uuuggcacuagcacauuuuugc | 362 | miR-96 |
| miR-98 | ugagguaguaaguuguauuguu | 363 | miR-98 |
| miR-99a | aacccguagauccgaucuugug | 364 | miR-99a |
| miR-99b | cacccguagaaccgaccuugcg | 365 | miR-99b |
| miR-100 | uacaguacugugauaacugaag | 366 | miR-100 |
| miR-101 | uacaguacugugauaacugaag | 367 | miR-101-1; miR-101-2 |
| miR-103 | agcagcauuguacagggcuauga | 368 | miR-103-1 |
| miR-105 | ucaaaugcucagacuccugu | 369 | miR-105 |
| miR-106-a | aaaagugcuuacagugcagguagc | 370 | miR-106-a |
| miR-106-b | uaaagugcugacagugcagau | 371 | miR-106-b |
| miR-107 | agcagcauuguacagggcuauca | 372 | mir-107 |
| miR-122a | uggagugugacaaugguguuugu | 373 | miR-122a-1; miR-122a-2 |
| miR-124a | uuaaggcacgcggugaaugcca | 374 | miR-124a-1; miR-124a-2; miR-124a-3 |
| miR-125a | ucccugagacccuuuaaccugug | 375 | miR-125a-1; miR-125a-2 |
| miR-125b | ucccugagacccuaacuuguga | 376 | miR-125b-1; miR-125b-2 |
| miR-126* | cauuauuacuuuugguacgcg | 377 | miR-126-1; miR-126-2 |
| miR-126 | ucguaccgugaguaauaaugc | 378 | miR-126-1; miR-126-2 |
| miR-127 | ucggauccgucugagcuggcu | 379 | miR-127-1; miR-127-2 |
| miR-128a | ucacagugaaccggucucuuuu | 380 | miR-128; miR-128a |
| miR-128b | ucacagugaaccggucucuuuc | 381 | miR-128b |
| miR-129 | cuuuugcggucugggcuugc | 382 | miR-129-1; miR-129-2 |
| miR-130a | cagugcaauguuaaaagggc | 383 | miR-130a |
| miR-130b | cagugcaaugaugaaagggcau | 384 | miR-130b |
| miR-132 | uaacagucuacagccauggucg | 385 | miR-132-1 |

TABLE 1b-continued

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| miR-133a | uugguccccuucaaccagcugu | 386 | miR-133a-1; miR-133a-2 |
| miR-133b | uugguccccuucaaccagcua | 387 | miR-133b |
| miR-134 | ugugacugguugaccagaggg | 388 | miR-134-1; miR-134-2 |
| miR-135a | uauggcuuuuuauuccuauguga | 389 | miR-135a; miR-135a-2 (miR-135-2) |
| miR-135b | uauggcuuuucauuccuaugug | 390 | miR-135b |
| miR-136 | acuccauuuguuugaugaugga | 391 | miR-136-1; miR-136-2 |
| miR-137 | uauugcuuaagaauacgcguag | 392 | miR-137 |
| miR-138 | agcugguguugugaauc | 393 | miR-138-1; miR-138-2 |
| miR-139 | ucuacagugcacgugucu | 394 | miR-139 |
| miR-140 | aguguuuuacccuaugguag | 395 | miR-140; miR-140as; miR-140s |
| miR-141 | aacacugucugguaaagaugg | 396 | miR-141-1; miR-141-2 |
| miR-142-3p | uguaguguuuccuacuuuaugga | 397 | miR-142 |
| miR-142-5p | cauaaaguagaaagcacuac | 398 | miR-142 |
| miR-143 | ugagaugaagcacuguagcuca | 399 | miR-143-1 |
| miR-144 | uacaguauagaugauguacuag | 400 | miR-144-1; miR-144-2 |
| miR-145 | guccaguuuucccaggaaucccuu | 401 | miR-145-1; miR-145-2 |
| miR-146 | ugagaacugaauuccauggguu | 402 | miR-146-1; miR-146-2 |
| miR-147 | guguguggaaaugcuucugc | 403 | miR-147 |
| miR-148a | ucagugcacuacagaacuuugu | 404 | miR-148a (miR-148) |
| miR-148b | ucagugcaucacagaacuuugu | 405 | miR-148b |
| miR-149 | ucuggcuccgugucuucacucc | 406 | miR-149 |
| miR-150 | ucucccaaccccuuguaccagug | 407 | miR-150-1; miR-150-2 |
| miR-151 | acuagacugaagcuccuugagg | 408 | miR-151 |
| miR-152 | ucagugcaugacagaacuugg | 409 | miR-152-1; miR-152-2 |
| miR-153 | uugcauagucacaaaaguga | 410 | miR-153-1-1; miR-153-1-2; miR-153-2-1; miR-153-2-2 |
| miR-154 | uagguuauccguguugccuucg | 411 | miR-154-1; miR-154-2 |
| miR-154* | aaucauacacgguugaccuauu | 412 | miR-154-1; miR-154-2 |
| miR-155 | uuaaugcuaaucugugauagggg | 413 | miR-155 |
| miR-181a | aacauucaacgcugucggugagu | 414 | miR-181a |
| miR-181b | aacauucauugcugucgguggguu | 415 | miR-181b-1; miR-181b-2 |
| miR-181c | aacauucaaccugucggugagu | 416 | miR-181c |
| miR-182 | uuuggcaaugguagaacucaca | 417 | miR-182; miR-182as |
| miR-182* | ugguucuagacuugccaacua | 418 | miR-182; miR-182as |
| miR-183 | uauggcacugguagaauucacug | 419 | miR-183 |
| miR-184 | uggacggagaacugauaagggu | 420 | miR-184-1; miR-184-2 |

TABLE 1b-continued

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| miR-185 | uggagagaaaggcaguuc | 421 | miR-185-1; miR-185-2 |
| miR-186 | caaagaauucuccuuuugggcuu | 422 | miR-186-1; miR-186-2 |
| miR-187 | ucgugucuuguguugcagccg | 423 | miR-187 |
| miR-188 | caucccuugcauggugagggu | 424 | miR-188 |
| miR-189 | gugccuacugagcugauaucagu | 425 | miR-189-1; miR-189-2 |
| miR-190 | ugauauguuugauauauuaggu | 426 | miR-190-1; miR-190-2 |
| miR-191 | caacggaaucccaaaagcagcu | 427 | miR-191-1; miR-191-2 |
| miR-192 | cugaccuaugaauugacagcc | 428 | miR-192 |
| miR-193 | aacuggccuacaaagucccag | 429 | miR-193-1; miR-193-2 |
| miR-194 | uguaacagcaacuccaugugga | 430 | miR-194-1; miR-194-2 |
| miR-195 | uagcagcacagaaauauuggc | 431 | miR-195-1; miR-195-2 |
| miR-196a | uagguaguuucauguuguugg | 432 | miR-196a; miR-196a-2 (miR196-2) |
| miR-196b | uagguaguuuccuguuguugg | 433 | miR-196b |
| miR-197 | uucaccaccuucuccacccagc | 434 | miR-197 |
| miR-198 | gguccagaggggagauagg | 435 | miR-198 |
| miR-199a | cccaguguucagacuaccuguuc | 436 | miR-199a-1; miR-199a-2 |
| miR-199a* | uacaguagucugcacauugguu | 437 | miR-199a-1; miR-199a-2; miR-199s; miR-199b |
| miR-199b | cccaguguuuagacuaucuguuc | 438 | miR-199b |
| miR-200a | uaacacugucugguaacgaugu | 439 | miR-200a |
| miR-200b | cucuaauacugccugguaaugaug | 440 | miR-200b |
| miR-200c | aauacugccggguaaugaugga | 441 | miR-200c |
| miR-202 | agagguauagggcauggaaga | 442 | miR-202 |
| miR-203 | gugaaauguuuaggaccacag | 443 | miR-203 |
| miR-204 | uucccuuugucauccuaugccu | 444 | miR-204 |
| miR-205 | uccuucauuccaccggagucug | 445 | miR-205 |
| miR-206 | uggaauguaaggaagugugugg | 446 | miR-206-1; miR-206-2 |
| miR-208 | auaagacgagcaaaaagcuugu | 447 | miR-208 |
| miR-210 | cugugcgugugacagcggcug | 448 | miR-210 |
| miR-211 | uucccuuugucauccuucgccu | 449 | miR-211 |
| miR-212 | uaacagucuccagucacggcc | 450 | miR-212 |
| miR-213 | accaucgaccguugauuguacc | 451 | miR-213 |
| miR-214 | acagcaggcacagacaggcag | 452 | miR-214 |
| miR-215 | augaccuaugaauugacagac | 453 | miR-215 |
| miR-216 | uaaucucagcuggcaacugug | 454 | miR-216 |
| miR-217 | uacugcaucaggaacugauuggau | 455 | miR-217 |

TABLE 1b-continued

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| miR-218 | uugugcuugaucuaaccaugu | 456 | miR-218-1; miR-218-2 |
| miR-219 | ugauuguccaaacgcaauucu | 457 | miR-219; miR-219-1; miR-219-2 |
| miR-220 | ccacaccguaucugacacuuu | 458 | miR-220 |
| miR-221 | agcuacauugucugcuggguuuc | 459 | miR-221 |
| miR-222 | agcuacaucuggcuacugggucuc | 460 | miR-222 |
| miR-223 | ugucaguuugucaaauacccc | 461 | miR-223 |
| miR-224 | caagucacuaguguuccguuua | 462 | miR-224 |
| miR-296 | agggccccccucaauccugu | 463 | miR-296 |
| miR-299 | ugguuuaccguccacauacau | 464 | miR-299 |
| miR-301 | cagugcaauaguauugucaaagc | 465 | miR-301 |
| miR-302a | uaagugcuuccauguuuugguga | 466 | miR-302a |
| miR-302b* | acuuuaacauggaagugcuuucu | 467 | miR-302b |
| miR-302b | uaagugcuuccauguuuuaguag | 468 | miR-302b |
| miR-302c* | uuuaacauggggguaccugcug | 469 | miR-302c |
| miR-302c | uaagugcuuccauguuucaguqg | 470 | miR-302c |
| miR-302d | uaagugcuuccauguuugagugu | 471 | miR-302d |
| miR-320 | aaaagcuggguugagagggcgaa | 472 | miR-320 |
| miR-321 | uaagccagggauugugggguuc | 473 | miR-321 |
| miR-323 | gcacauuacacggucgaccucu | 474 | miR-323 |
| miR-324-5p | cgcaucccuagggcauuggugu | 475 | miR-324 |
| miR-324-3p | ccacugccccaggugcugcugg | 476 | miR-324 |
| miR-325 | ccuaguagguguccaguaagu | 477 | miR-325 |
| miR-326 | ccucugggcccuuccuccag | 478 | miR-326 |
| miR-328 | cuggcccucucugcccuuccgu | 479 | miR-328 |
| miR-330 | gcaaagcacacggccugcagaga | 480 | miR-330 |
| miR-331 | gccccugggccuauccuagaa | 481 | miR-331 |
| miR-335 | ucaagagcaauaacgaaaaaugu | 482 | miR-335 |
| miR-337 | uccagcuccuauaugaugccuuu | 483 | miR-337 |
| miR-338 | uccagcaucagugauuuuguuga | 484 | miR-338 |
| miR-339 | ucccuguccuccaggagcuca | 485 | miR-339 |
| miR-340 | uccgucucaguuacuuuauagcc | 486 | miR-340 |
| miR-342 | ucucacacagaaaucgcacccguc | 487 | miR-342 |
| miR-345 | ugcugacuccuaguccagggc | 488 | miR-345 |
| miR-346 | ugucugcccgcaugccugccucu | 489 | miR-346 |
| miR-367 | aauugcacuuuagcaaugguga | 490 | miR-367 |
| miR-368 | acauagaggaaauuccacguuu | 491 | miR-368 |

TABLE 1b-continued

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| miR-369 | aauaauacaugguugaucuuu | 492 | miR-369 |
| miR-370 | gccugcuggggguggaaccugg | 493 | miR-370 |
| miR-371 | gugccgccaucuuuugagugu | 494 | miR-371 |
| miR-372 | aaagugcugcgacauuugagcgu | 495 | miR-372 |
| miR-373* | acucaaaauggggggcgcuuucc | 496 | miR-373 |
| miR-373 | gaagugcuucgauuuuggggugu | 497 | miR-373 |
| miR-374 | uuauaauacaaccugauaagug | 498 | miR-374 |

The level of at least one miR gene product can be measured in cells of a biological sample obtained from the subject. For example, a tissue sample can be removed from a subject suspected of having pancreatic cancer by conventional biopsy techniques. In another embodiment, a blood sample can be removed from the subject, and white blood cells can be isolated for DNA extraction by standard techniques. The blood or tissue sample is preferably obtained from the subject prior to initiation of radiotherapy, chemotherapy or other therapeutic treatment. A corresponding control tissue or blood sample, or a control reference sample, can be obtained from unaffected tissues of the subject, from a normal human individual or population of normal individuals, or from cultured cells corresponding to the majority of cells in the subject's sample. The control tissue or blood sample is then processed along with the sample from the subject, so that the levels of miR gene product produced from a given miR gene in cells from the subject's sample can be compared to the corresponding miR gene product levels from cells of the control sample. Alternatively, a reference sample can be obtained and processed separately (e.g., at a different time) from the test sample and the level of a miR gene product produced from a given miR gene in cells from the test sample can be compared to the corresponding miR gene product level from the reference sample.

In one embodiment, the level of the at least one miR gene product in the test sample is greater than the level of the corresponding miR gene product in the control sample (i.e., expression of the miR gene product is "upregulated"). As used herein, expression of a miR gene product is "upregulated" when the amount of miR gene product in a cell or tissue sample from a subject is greater than the amount of the same gene product in a control cell or tissue sample. In another embodiment, the level of the at least one miR gene product in the test sample is less than the level of the corresponding miR gene product in the control sample (i.e., expression of the miR gene product is "downregulated"). As used herein, expression of a miR gene is "downregulated" when the amount of miR gene product produced from that gene in a cell or tissue sample from a subject is less than the amount produced from the same gene in a control cell or tissue sample. The relative miR gene expression in the control and normal samples can be determined with respect to one or more RNA expression standards. The standards can comprise, for example, a zero miR gene expression level, the miR gene expression level in a standard cell line, the miR gene expression level in unaffected tissues of the subject, or the average level of miR gene expression previously obtained for a population of normal human controls.

An alteration (i.e., an increase or decrease) in the level of a miR gene product in the sample obtained from the subject, relative to the level of a corresponding miR gene product in a control sample, is indicative of the presence of pancreatic cancer in the subject. In one embodiment, the level of the at least one miR gene product in the test sample is greater than the level of the corresponding miR gene product in the control sample. miR gene products having higher expression levels in pancreatic cancer than normal pancreatic tissue are described herein (see, e.g., Exemplification). In one embodiment, the at least one miR gene product is selected from the group consisting of miR-103-2, miR-107, miR-103-1, miR-342, miR-100, miR-24-2, miR-23a, miR-125a, miR-26a-1, miR-24-1, miR-191, miR-15a, miR-368, miR-26b, miR-125b-2, miR-125b-1, miR-26a-2, miR-335, miR-126, miR-1-2, miR-21, miR-25, miR-92-2, miR-130a, miR-93, miR-16-1, miR-145, miR-17, miR-99b, miR-181b-1, miR-146, miR-181b-2, miR-16-2, miR-99a, miR-197, miR-10a, miR-224, miR-92-1, miR-27a, miR-221, miR-320, miR-7-1, miR-29b-2, miR-150, miR-30d, miR-29a, miR-23b, miR-135a-2, miR-223, miR-3p21-v, miR-128b, miR-30b, miR-29b-1, miR-106b, miR-132, miR-214, miR-7-3, miR-29c, miR-367, miR-30c-2, miR-27b, miR-140, miR-10b, miR-20, miR-129-1, miR-340, miR-30a, miR-30c-1, miR-106a, miR-32, miR-95, miR-222, miR-30e, miR-129-2, miR-345, miR-143, miR-182, miR-1-1, miR-133a-1, miR-200c, miR-194-1, miR-210, miR-181c, miR-192, miR-220, miR-213, miR-323, miR-375 and a combination thereof. In another embodiment, the at least one miR gene product is selected from the group consisting of miR-103, miR-107 and a combination thereof. In yet another embodiment, the at least one miR gene product is selected from the group consisting of miR-23a, miR-26b, miR-192, miR-342 and a combination thereof.

In one embodiment, the level of the at least one miR gene product in the test sample is less than the level of the corresponding miR gene product in the control sample. miR gene products having lower expression levels in pancreatic cancer than normal pancreatic tissue are described herein (see, e.g., Exemplification). In one embodiment, the at least one miR gene product is selected from the group consisting of miR-326, miR-155, miR-339, miR-34c, miR-345, miR-152, miR-372, miR-128a and a combination thereof. In another embodiment, the at least one miR gene product is miR-155.

In one embodiment, the at least one miR gene product is selected from the group consisting of miR-103, is miR-107, miR-155 and a combination thereof. In another embodiment, the at least one miR gene product is miR-103, which is upregulated in the test sample, as compared to the control sample. In yet another embodiment, the at least one miR gene product is miR-107, which is upregulated in the test sample, as compared to the control sample. In still another embodiment, the at least one miR gene product is miR-155, which is downregulated in the test sample, as compared to the control sample. In a particular embodiment, all three of these miRs (miR-103, miR-107 and miR-155) are compared to the corresponding miRs in the control sample. As described and exemplified herein, the expression of miR-103 and miR-107, associated with lack of expression of miR-155, discriminates pancreatic tumors from normal pancreas.

In one embodiment, the pancreatic cancer that is diagnosed is a pancreatic endocrine tumor (PET). In another embodiment, the pancreatic cancer that is diagnosed is a pancreatic exocrine tumor (e.g., an adenocarcinoma). In yet another embodiment, the pancreatic cancer that is diagnosed is selected from the group consisting of a pancreatic endocrine tumor (PET) and a pancreatic exocrine tumor (e.g., an adenocarcinoma). In a particular embodiment, the pancreatic cancer that is diagnosed is selected from the group consisting of an acinar cell carcinoma (PACC) and an insulinoma. In yet another embodiment, the pancreatic cancer that is diagnosed is selected from the group consisting of a pancreatic endocrine tumor (PET), a pancreatic acinar cell carcinoma (PACC) and an insulinoma. In still another embodiment, the diagnostic method can be used to diagnose any type of pancreatic cancer.

In one embodiment, the invention is a method of diagnosing whether a subject has, or is at risk for developing, pancreatic acinar cell carcinoma (PACC). In this method, the level of at least one miR gene product in a test sample from the subject is compared to the level of a corresponding miR gene product in a control sample. An alteration (e.g., an increase, a decrease) in the level of the miR gene product in the test sample, relative to the level of a corresponding miR gene product in a control sample, is indicative of the subject either having, or being at risk for developing, PACC. In one embodiment, the level of the at least one miR gene product in the test sample is greater than the level of the corresponding miR gene product in the control sample. In another embodiment, the at least one miR gene product that is upregulated is selected from the group consisting of miR-103-2, miR-25, miR-200c, miR-335, miR-21, miR-103-1, miR-92-1, miR-181b-2, miR-191, miR-93, miR-26a-1, miR-17, miR-20, miR-107, miR-26b, miR-215, miR-92-2, miR-192, miR-342, miR-100, miR-3p21-v, miR-106a, miR-15a, miR-23a, miR-181b-1, miR-128b, miR-106b, miR-194-1, miR-219-1, miR-242 and a combination thereof. In yet another embodiment, the level of the at least one miR gene product in the test sample is less than the level of the corresponding miR gene product in the control sample. In still another embodiment, the at least one miR gene product that is downregulated is selected from the group consisting of miR-218-2, miR-339, miR-326, miR-34c, miR-152, miR-138-2, miR-128a and a combination thereof.

In one embodiment, the invention is a method of diagnosing the type of pancreatic cancer that a subject has. In this method, the level of at least one miR gene product in a test sample from the subject is compared to the level of a corresponding miR gene product in a control sample. An alteration (e.g., an increase, a decrease) in the level of the miR gene product in the test sample, relative to the level of a corresponding miR gene product in a control sample, is indicative of the type of pancreatic cancer.

In a particular embodiment, the type of pancreatic cancer that is diagnosed is selected from the group consisting of a pancreatic endocrine tumor (PET) and a pancreatic acinar cell carcinoma (PACC). In another embodiment, the level of the at least one miR gene product in the test sample is greater than the level of the corresponding miR gene product in the control sample. In another embodiment, the type of pancreatic cancer is a pancreatic endocrine tumor (PET) and the at least one miR gene product that is upregulated is selected from the group consisting of miR-125a, miR-99a, miR-99b, miR-125b-1, miR-342, miR-130a, miR-100, miR-132, miR-129-2, miR-125b-2 and a combination thereof. In yet another embodiment, the level of the at least one miR gene product in the test sample is less than the level of the corresponding miR gene product in the control sample. In still another embodiment, the type of pancreatic cancer is a pancreatic acinar cell carcinoma (PACC) and the at least one miR gene product that is downregulated is selected from the group consisting of miR-125a, miR-99a, miR-99b, miR-125b-1, miR-342, miR-130a, miR-100, miR-132, miR-129-2, miR-125b-2 and a combination thereof. As described herein, the expression of particular miR gene products can distinguish between PET and PACC (see, e.g., Exemplification).

In one embodiment, the type of pancreatic cancer that is diagnosed is selected from the group consisting of a well-differentiated endocrine carcinoma (WDEC) and a pancreatic acinar cell carcinoma (PACC). In another embodiment, the level of the at least one miR gene product in the test sample is greater than the level of the corresponding miR gene product in the control sample. In yet another embodiment, the type of pancreatic cancer is a well-differentiated endocrine carcinoma (WDEC) and the at least one miR gene product that is upregulated is selected from the group consisting of miR-125a, miR-99a, miR-132 and a combination thereof. In another embodiment, the level of the at least one miR gene product in the test sample is less than the level of the corresponding miR gene product in the control sample. In still another embodiment, the type of pancreatic cancer is a well-differentiated endocrine carcinoma (WDEC) and the at least one miR gene product that is downregulated is miR-148a. As described herein, the expression of particular miR gene products can distinguish between WDEC and PACC (see, e.g., Exemplification).

In one embodiment, the type of pancreatic cancer that is diagnosed is selected from the group consisting of an insulinoma and a non-functioning pancreatic endocrine tumor (NF-PET). In one embodiment, the level of the at least one miR gene product in the test sample is greater than the level of the corresponding miR gene product in the control sample. In another embodiment, the type of pancreatic cancer is an insulinoma and the at least one miR gene product that is upregulated is selected from the group consisting of miR-204, miR-203, miR-211 and a combination thereof. As described herein, the expression of particular miR gene products can distinguish between WDEC and PACC (see, e.g., Exemplification).

The invention also provides methods of determining the prognosis of a subject with pancreatic cancer. In this method, the level of at least one miR gene product, which is associated with a particular prognosis in pancreatic cancer (e.g., a good or positive prognosis, a poor or adverse prognosis), is measured in a test sample from the subject. An alteration (e.g., an increase, a decrease) in the level of the miR gene product in the test sample, relative to the level of a corresponding miR gene product in a control sample, is indicative of the subject having a pancreatic cancer with a particular prognosis. In one embodiment, the miR gene product is associated with an adverse (i.e., poor) prognosis. Examples of an adverse prognosis include, but are not limited to, low survival rate and rapid disease progression. In one embodiment, the level of the at least one miR gene product in the test sample is greater than the level of the corresponding miR gene product in a control sample. In another embodiment, the at least one miR gene product that is upregulated, and which is measured, is miR-21. In yet another embodiment, the pancreatic cancer is associated with metastasis and/or a high proliferation index. As described herein, the expression of particular miR gene products, which are associated with an adverse prognosis in pancreatic cancer, can prognosticate the severity of a subject's pancreatic cancer (see, e.g., Exemplification). In certain embodiments, the level of the at least one miR gene product is measured by reverse transcribing RNA from a test sample obtained from the subject to provide a set of target oligodeoxynucleotides, hybridizing the target oligodeoxynucleotides to a microarray that comprises miRNA-specific probe oligonucleotides to provide a hybridization profile for the test sample, and comparing the test sample hybridization profile to a hybridization profile generated from a control sample.

In one embodiment, the invention is a method of determining whether a pancreatic cancer in a subject is metastatic. As described herein, most PET-related deaths are caused by liver metastasis. Thus, identification of metastatic pancreatic cancer can aid in determining appropriate treatment options. In this method, the level of at least one miR gene product is measured in a test sample (e.g., a pancreatic cancer sample) from the subject. An alteration (e.g., an increase, a decrease) in the level of the miR gene product in the test sample, relative to the level of a corresponding miR gene product in a control sample, is indicative of metastasis. In one embodiment, the level of the at least one miR gene product in the test sample is greater than the level of the corresponding miR gene product in the control sample. In another embodiment, the at least one miR gene product that is upregulated is miR-21.

In one embodiment, the invention is a method of determining whether a pancreatic cancer in a subject has a high proliferation index. As is known, pancreatic cancers having a high proliferation index have an adverse prognosis and, therefore, identification of pancreatic cancers having a high proliferation index can also aid in determining appropriate treatment options. In this method, the level of at least one miR gene product is measured in a test sample (e.g., a pancreatic cancer sample) from the subject. An alteration (e.g., an increase, a decrease) in the level of the miR gene product in the test sample, relative to the level of a corresponding miR gene product in a control sample, is indicative of a high proliferation index. In one embodiment, the level of the at least one miR gene product in the test sample is greater than the level of the corresponding miR gene product in the control sample. In another embodiment, the at least one miR gene product that is upregulated is miR-21.

Identification of targets of particular miR gene products (e.g., those miR gene products exhibiting upregulated or downregulated expression relative to a control sample) can aid in elucidating mechanisms of action of microRNAs. As exemplified herein, particular putative targets of select microRNAs, namely miR-103/miR-107, miR-155, miR-204/miR-211 and miR-21, were identified. Analysis revealed numerous upregulated (28 target genes) and downregulated (7 target genes) target genes of particular microRNAs in pancreatic cancer samples. As described in Table 10, 28 upregulated target genes and 7 downregulated target genes of miR-103/miR-107 were identified in pancreatic cancer samples (Exemplification and Table 10). In addition, 2 upregulated target genes and 2 downregulated target genes of miR-103/miR-107, and 1 upregulated target gene and 1 downregulated target gene of miR-21 were identified in pancreatic cancer samples (Exemplification and Table 10). Thus, in one embodiment, expression of target genes of particular microRNAs (e.g., those listed in Table 10) can be used to diagnose cancer (e.g., pancreatic cancer). One of skill in the art can measure the expression levels of any of these target genes using known methods and/or methods described herein for measuring the expression levels of microRNAs (e.g., quantitative or semi-quantitative RT-PCR, Northern blot analysis, solution hybridization detection, microarray analysis), without undue experimentation. In one embodiment, the target gene that is measured is Programmed Cell Death 4 (PDCD4).

In one embodiment, the invention is a method of determining the prognosis of a subject with pancreatic cancer. In this method, the level of PDCD4 is measured in a test sample (e.g., a pancreatic cancer sample) from the subject. An alteration (e.g., an increase, a decrease) in the level of PDCD4 in the test sample, relative to the level of PDCD4 in a control sample, is indicative of an adverse prognosis. In one embodiment, the level of PDCD4 in the test sample is less than the level of PDCD4 in the control sample. In another embodiment, the pancreatic cancer is associated with metastasis and/or a high proliferation index.

The level of the at least one miR gene product can be measured using a variety of techniques that are well known to those of skill in the art (e.g., quantitative or semi-quantitative RT-PCR, Northern blot analysis, solution hybridization detection). In a particular embodiment, the level of at least one miR gene product is measured by reverse transcribing RNA from a test sample obtained from the subject to provide a set of target oligodeoxynucleotides, hybridizing the target oligodeoxynucleotides to one or more miRNA-specific probe oligonucleotides (e.g., a microarray that comprises miRNA-specific probe oligonucleotides) to provide a hybridization profile for the test sample, and comparing the test sample hybridization profile to a hybridization profile generated from a control sample. An alteration in the signal of at least one miRNA in the test sample relative to the control sample is indicative of the subject either having, or being at risk for developing, pancreatic cancer. In one embodiment, the signal of at least one miRNA is upregulated, relative to the signal generated from the control sample. In another embodiment, the signal of at least one miRNA is down-regulated, relative to the signal generated from the control sample. In a particular embodiment, the microarray comprises miRNA-specific probe oligonucleotides for a substantial portion of all known human miRNAs. In a further embodiment, the microarray comprises miRNA-specific probe oligonucleotides for one or more miRNAs selected from the group consisting of miR-103-2, miR-107, miR-103-1, miR-342, miR-100, miR-24-2, miR-23a, miR-125a, miR-26a-1, miR-24-1, miR-191, miR-15a, miR-368, miR-26b, miR-125b-2, miR-125b-1, miR-26a-2, miR-335, miR-126, miR-1-2, miR-21, miR-25, miR-92-2, miR-130a, miR-93, miR-16-1, miR-145, miR-17, miR-99b, miR-181b-1, miR-146, miR-181b-2, miR-16-2, miR-99a, miR-197, miR-10a, miR-224, miR-92-1, miR-27a, miR-221, miR-320, miR-7-1, miR-29b-2, miR-150, miR-30d, miR-29a, miR-23b, miR-135a-2, miR-223, miR-3p21-v, miR-128b, miR-30b, miR-29b-1, miR-106b, miR-132, miR-214, miR-7-3, miR-29c, miR-367, miR-30c-2, miR-27b, miR-140, miR-10b, miR-20, miR-129-1, miR-340, miR-30a, miR-30c-1, miR-106a, miR-32, miR-95, miR-222, miR-30e, miR-129-2, miR-345, miR-143, miR-182, miR-1-1, miR- 133a-1, miR-200c, miR-194-1, miR-210, miR-181c, miR-192, miR-220, miR-213, miR-323, miR-375, miR-326, miR-155, miR-339, miR-34c, miR-345, miR-152, miR-372, miR-128a and a combination thereof.

The microarray can be prepared from gene-specific oligonucleotide probes generated from known miRNA sequences. The array may contain two different oligonucleotide probes for each miRNA, one containing the active, mature sequence and the other being specific for the precursor of the miRNA. The array may also contain controls, such as one or more mouse sequences differing from human orthologs by only a few bases, which can serve as controls for hybridization stringency conditions. tRNAs and other RNAs (e.g., rRNAs, mRNAs) from both species may also be printed on the microchip, providing an internal, relatively stable, positive control for specific hybridization. One or more appropriate controls for non-specific hybridization may also be included on the microchip. For this purpose, sequences are selected based upon the absence of any homology with any known miRNAs.

The microarray may be fabricated using techniques known in the art. For example, probe oligonucleotides of an appropriate length, e.g., 40 nucleotides, are 5'-amine modified at position C6 and printed using commercially available microarray systems, e.g., the GeneMachine OmniGrid™ 100 Microarrayer and Amersham CodeLink™ activated slides. Labeled cDNA oligomer corresponding to the target RNAs is prepared by reverse transcribing the target RNA with labeled primer. Following first strand synthesis, the RNA/DNA hybrids are denatured to degrade the RNA templates. The labeled target cDNAs thus prepared are then hybridized to the microarray chip under hybridizing conditions, e.g., 6×SSPE/30% formamide at 25° C. for 18 hours, followed by washing in 0.75×TNT at 37° C. for 40 minutes. At positions on the array where the immobilized probe DNA recognizes a complementary target cDNA in the sample, hybridization occurs. The labeled target cDNA marks the exact position on the array where binding occurs, allowing automatic detection and quantification. The output consists of a list of hybridization events, indicating the relative abundance of specific cDNA sequences, and therefore the relative abundance of the corresponding complementary miRs, in the patient sample. According to one embodiment, the labeled cDNA oligomer is a biotin-labeled cDNA, prepared from a biotin-labeled primer. The microarray is then processed by direct detection of the biotin-containing transcripts using, e.g., Streptavidin-Alexa647 conjugate, and scanned utilizing conventional scanning methods. Image intensities of each spot on the array are proportional to the abundance of the corresponding miR in the patient sample.

The use of the array has several advantages for miRNA expression detection. First, the global expression of several hundred genes can be identified in the same sample at one time point. Second, through careful design of the oligonucleotide probes, expression of both mature and precursor molecules can be identified. Third, in comparison with Northern blot analysis, the chip requires a small amount of RNA, and provides reproducible results using 2.5 μg of total RNA. The relatively limited number of miRNAs (a few hundred per species) allows the construction of a common microarray for several species, with distinct oligonucleotide probes for each. Such a tool would allow for analysis of trans-species expression for each known miR under various conditions.

In addition to use for quantitative expression level assays of specific miRs, a microchip containing miRNA-specific probe oligonucleotides corresponding to a substantial portion of the miRNome, preferably the entire miRNome, may be employed to carry out miR gene expression profiling, for analysis of miR expression patterns. Distinct miR signatures can be associated with established disease markers, or directly with a disease state.

According to the expression profiling methods described herein, total RNA from a sample from a subject suspected of having a cancer (e.g., pancreatic cancer) is quantitatively reverse transcribed to provide a set of labeled target oligodeoxynucleotides complementary to the RNA in the sample. The target oligodeoxynucleotides are then hybridized to a microarray comprising miRNA-specific probe oligonucleotides to provide a hybridization profile for the sample. The result is a hybridization profile for the sample representing the expression pattern of miRNA in the sample. The hybridization profile comprises the signal from the binding of the target oligodeoxynucleotides from the sample to the miRNA-specific probe oligonucleotides in the microarray. The profile may be recorded as the presence or absence of binding (signal vs. zero signal). More preferably, the profile recorded includes the intensity of the signal from each hybridization. The profile is compared to the hybridization profile generated from a normal, e.g., noncancerous, control sample. An alteration in the signal is indicative of the presence of, or propensity to develop, cancer in the subject.

Other techniques for measuring miR gene expression are also within the skill in the art, and include various techniques for measuring rates of RNA transcription and degradation.

The invention also provides methods of diagnosing whether a subject has, or is at risk for developing, a pancreatic cancer with an adverse prognosis. In this method, the level of at least one miR gene product, which is associated with an adverse prognosis in pancreatic cancer, is measured by reverse transcribing RNA from a test sample obtained from the subject to provide a set of target oligodeoxynucleotides. The target oligodeoxynucleotides are then hybridized to one or more miRNA-specific probe oligonucleotides (e.g., a microarray that comprises miRNA-specific probe oligonucleotides) to provide a hybridization profile for the test sample, and the test sample hybridization profile is compared to a hybridization profile generated from a control sample. An alteration in the signal of at least one miRNA in the test sample relative to the control sample is indicative of the subject either having, or being at risk for developing, a pancreatic cancer with an adverse prognosis. In one embodiment, an alteration in the signal of miR-21 is indicative of the subject either having, or being at risk for developing, a pancreatic cancer with an adverse prognosis.

In particular embodiments of the diagnostic, prognostic and therapeutic methods of the invention, the miR gene product is not one or more of let7a-2, let-7c, let-7g, let-7i, miR-7-2, miR-7-3, miR-9, miR-9-1, miR-10a, miR-1Sa, miR-15b, miR-16-1, miR-16-2, miR-17-5p, miR-20a, miR-21, miR-24-1, miR-24-2, miR-25, miR-29b-2, miR-30, miR-30a-5p, miR-30c, miR-30d, miR-31, miR-32, miR-34, miR-34a, miR-34a prec, miR-34a-1, miR-34a-2, miR-92-2, miR-96, miR-99a, miR-99b prec, miR-100, miR-103, miR-106a, miR-107, miR-123, miR-124a-1, miR-125b-1, miR-125b-2, miR-126*, miR-127, miR-128b, miR-129, miR-129-1/2 prec, miR-132, miR-135-1, miR-136, miR-137, miR-141, miR-142-as, miR-143, miR-146, miR-148, miR-149, miR-153, miR-155, miR 159-1, miR-181, miR-181b-1, miR-182, miR-186, miR-191, miR-192, miR-195, miR-196-1, miR-196-1 prec, miR-196-2, miR-199a-1, miR-199a-2, miR-199b, miR-200b, miR-202, miR-203, miR-204, miR-205, miR-210, miR-211, miR-212, miR-214, miR-215, miR-217, miR-221 and/or miR-223.

As described herein, the level of a miR gene product in a sample can be measured using any technique that is suitable for detecting RNA expression levels in a biological sample. Suitable techniques (e.g., Northern blot analysis, RT-PCR, in situ hybridization) for determining RNA expression levels in a biological sample (e.g., cells, tissues) are well known to those of skill in the art. In a particular embodiment, the level of at least one miR gene product is detected using Northern blot analysis. For example, total cellular RNA can be purified from cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters. The RNA is then immobilized on the filters by heating. Detection and quantification of specific RNA is accomplished using appropriately labeled DNA or RNA probes complementary to the RNA in question. See, for example, Molecular Cloning: A Laboratory Manual, J. Sambrook et al., eds., 2nd edition, Cold Spring Harbor Laboratory Press, 1989, Chapter 7, the entire disclosure of which is incorporated by reference.

Suitable probes (e.g., DNA probes, RNA probes) for Northern blot hybridization of a given miR gene product can be produced from the nucleic acid sequences provided in Table 1a and Table 1b and include, but are not limited to, probes having at least about 70%, 75%, 80%, 85%, 90%, 95%, 98% or 99% complementarity to a miR gene product of interest, as well as probes that have complete complementarity to a miR gene product of interest. Methods for preparation of labeled DNA and RNA probes, and the conditions for hybridization thereof to target nucleotide sequences, are described in Molecular Cloning: A Laboratory Manual, J. Sambrook et al., eds., 2nd edition, Cold Spring Harbor Laboratory Press, 1989, Chapters 10 and 11, the disclosures of which are incorporated herein by reference.

For example, the nucleic acid probe can be labeled with, e.g., a radionuclide, such as $^3$H, $^{32}$P, $^{33}$P, $^{14}$C, or $^{35}$S; a heavy metal; a ligand capable of functioning as a specific binding pair member for a labeled ligand (e.g., biotin, avidin or an antibody); a fluorescent molecule; a chemiluminescent molecule; an enzyme or the like.

Probes can be labeled to high specific activity by either the nick translation method of Rigby et al. (1977), *J. Mol. Biol.* 113:237-251 or by the random priming method of Fienberg et al. (1983), *Anal. Biochem.* 132:6-13, the entire disclosures of which are incorporated herein by reference. The latter is the method of choice for synthesizing $^{32}$P-labeled probes of high specific activity from single-stranded DNA or from RNA templates. For example, by replacing preexisting nucleotides with highly radioactive nucleotides according to the nick translation method, it is possible to prepare $^{32}$P-labeled nucleic acid probes with a specific activity well in excess of $10^8$ cpm/microgram. Autoradiographic detection of hybridization can then be performed by exposing hybridized filters to photographic film. Densitometric scanning of the photographic films exposed by the hybridized filters provides an accurate measurement of miR gene transcript levels. Using another approach, miR gene transcript levels can be quantified by computerized imaging systems, such as the Molecular Dynamics 400-B 2D Phosphorimager available from Amersham Biosciences, Piscataway, N.J.

Where radionuclide labeling of DNA or RNA probes is not practical, the random-primer method can be used to incorporate an analogue, for example, the dTTP analogue 5-(N—(N-biotinyl-epsilon-aminocaproyl)-3-aminoallyl)deoxyuridine triphosphate, into the probe molecule. The biotinylated probe oligonucleotide can be detected by reaction with biotin-binding proteins, such as avidin, streptavidin and antibodies (e.g., anti-biotin antibodies) coupled to fluorescent dyes or enzymes that produce color reactions.

In addition to Northern and other RNA hybridization techniques, determining the levels of RNA transcripts can be accomplished using the technique of in situ hybridization. This technique requires fewer cells than the Northern blotting technique and involves depositing whole cells onto a microscope cover slip and probing the nucleic acid content of the cell with a solution containing radioactive or otherwise labeled nucleic acid (e.g., cDNA or RNA) probes. This technique is particularly well-suited for analyzing tissue biopsy samples from subjects. The practice of the in situ hybridization technique is described in more detail in U.S. Pat. No. 5,427,916, the entire disclosure of which is incorporated herein by reference. Suitable probes for in situ hybridization of a given miR gene product can be produced from the nucleic acid sequences provided in Table 1a and Table 1b, and include, but are not limited to, probes having at least about 70%, 75%, 80%, 85%, 90%, 95%, 98% or 99% complementarity to a miR gene product of interest, as well as probes that have complete complementarity to a miR gene product of interest, as described above.

The relative number of miR gene transcripts in cells can also be determined by reverse transcription of miR gene transcripts, followed by amplification of the reverse-transcribed transcripts by polymerase chain reaction (RT-PCR). The levels of miR gene transcripts can be quantified in comparison with an internal standard, for example, the level of mRNA from a "housekeeping" gene present in the same sample. A suitable "housekeeping" gene for use as an internal standard includes, e.g., myosin or glyceraldehyde-3-phosphate dehydrogenase (G3PDH). Methods for performing quantitative and semi-quantitative RT-PCR, and variations thereof, are well known to those of skill in the art.

In some instances, it may be desirable to simultaneously determine the expression level of a plurality of different miR gene products in a sample. In other instances, it may be desirable to determine the expression level of the transcripts of all known miR genes correlated with a cancer (e.g., pancreatic cancer). Assessing cancer-specific expression levels for hundreds of miR genes or gene products is time consuming and requires a large amount of total RNA (e.g., at least 20 μg for each Northern blot) and autoradiographic techniques that require radioactive isotopes.

To overcome these limitations, an oligolibrary, in microchip format (i.e., a microarray), may be constructed containing a set of oligonucleotide (e.g., oligodeoxynucleotide) probes that are specific for a set of miR genes. Using such a microarray, the expression level of multiple microRNAs in a biological sample can be determined by reverse transcribing the RNAs to generate a set of target oligodeoxynucleotides, and hybridizing them to probe the oligonucleotides on the microarray to generate a hybridization, or expression, profile. The hybridization profile of the test sample can then be compared to that of a control sample to determine which microRNAs have an altered expression level in pancreatic cancer cells. As used herein, "probe oligonucleotide" or "probe oligodeoxynucleotide" refers to an oligonucleotide that is capable of hybridizing to a target oligonucleotide. "Target oligonucleotide" or "target oligodeoxynucleotide" refers to a molecule to be detected (e.g., via hybridization). By "miR-specific probe oligonucleotide" or "probe oligonucleotide specific for a miR" is meant a probe oligonucleotide that has a sequence selected to hybridize to a specific miR gene product, or to a reverse transcript of the specific miR gene product.

An "expression profile" or "hybridization profile" of a particular sample is essentially a fingerprint of the state of the sample; while two states may have any particular gene similarly expressed, the evaluation of a number of genes simultaneously allows the generation of a gene expression profile that is unique to the state of the cell. That is, normal tissue may be distinguished from pancreatic cancer tissue, and within pancreatic cancer tissue, different prognosis states (for example, good or poor long term survival prospects) may be determined. By comparing expression profiles of pancreatic cancer tissue in different states, information regarding which genes are important (including both upregulation and downregulation of genes) in each of these states is obtained. The identification of sequences that are differentially expressed in pancreatic cancer tissue or normal pancreatic tissue, as well as differential expression resulting in different prognostic outcomes, allows the use of this information in a number of ways. For example, a particular treatment regime may be evaluated (e.g., to determine whether a chemotherapeutic drug acts to improve the long-term prognosis in a particular patient). Similarly, diagnosis may be done or confirmed by comparing patient samples with known expression profiles. Furthermore, these gene expression profiles (or individual genes) allow screening of drug candidates that suppress the pancreatic cancer expression profile or convert a poor prognosis profile to a better prognosis profile.

Without wishing to be bound by any one theory, it is believed that alterations in the level of one or more miR gene products in cells can result in the deregulation of one or more intended targets for these miRs, which can lead to the formation of pancreatic cancer. Therefore, altering the level of the miR gene product (e.g., by decreasing the level of a miR that is upregulated in pancreatic cancer cells, by increasing the level of a miR that is downregulated in pancreatic cancer cells) may successfully treat the pancreatic cancer.

Accordingly, the present invention encompasses methods of treating pancreatic cancer in a subject, wherein at least one miR gene product is deregulated (e.g., downregulated, upregulated) in the cells (e.g., pancreatic cancer cells) of the subject. In one embodiment, the level of at least one miR gene product in a test sample (e.g., a pancreatic cancer sample) is greater than the level of the corresponding miR gene product in a control sample. In another embodiment, the level of at least one miR gene product in a test sample (e.g., a pancreatic cancer sample is less than the level of the corresponding miR gene product in a control sample. When the at least one isolated miR gene product is downregulated in the pancreatic cancer cells, the method comprises administering an effective amount of the at least one isolated miR gene product, or an isolated variant or biologically-active fragment thereof, such that proliferation of cancer cells in the subject is inhibited. For example, when a miR gene product is downregulated in a cancer cell in a subject, administering an effective amount of an isolated miR gene product to the subject can inhibit proliferation of the cancer cell. The isolated miR gene product that is administered to the subject can be identical to an endogenous wild-type miR gene product (e.g., a miR gene product shown in Table 1a or Table 1b) that is downregulated in the cancer cell or it can be a variant or biologically-active fragment thereof. As defined herein, a "variant" of a miR gene product refers to a miRNA that has less than 100% identity to a corresponding wild-type miR gene product and possesses one or more biological activities of the corresponding wild-type miR gene product. Examples of such biological activities include, but are not limited to, inhibition of expression of a target RNA molecule (e.g., inhibiting translation of a target RNA molecule, modulating the stability of a target RNA molecule, inhibiting processing of a target RNA molecule) and inhibition of a cellular process associated with pancreatic cancer (e.g., cell differentiation, cell growth, cell death). These variants include species variants and variants that are the consequence of one or more mutations (e.g., a substitution, a deletion, an insertion) in a miR gene. In certain embodiments, the variant is at least about 70%, 75%, 80%, 85%, 90%, 95%, 98%, or 99% identical to a corresponding wild-type miR gene product.

As defined herein, a "biologically-active fragment" of a miR gene product refers to an RNA fragment of a miR gene product that possesses one or more biological activities of a corresponding wild-type miR gene product. As described above, examples of such biological activities include, but are not limited to, inhibition of expression of a target RNA molecule and inhibition of a cellular process associated with pancreatic cancer. In certain embodiments, the biologically-active fragment is at least about 5, 7, 10, 12, 15, or 17 nucleotides in length. In a particular embodiment, an isolated miR gene product can be administered to a subject in combination with one or more additional anti-cancer treatments. Suitable anti-cancer treatments include, but are not limited to, chemotherapy, radiation therapy and combinations thereof (e.g., chemoradiation).

When the at least one isolated miR gene product is upregulated in the cancer cells, the method comprises administering to the subject an effective amount of a compound that inhibits expression of the at least one miR gene product, such that proliferation of pancreatic cancer cells is inhibited. Such compounds are referred to herein as miR gene expression-inhibition compounds. Examples of suitable miR gene expression-inhibition compounds include, but are not limited to, those described herein (e.g., double-stranded RNA, antisense nucleic acids and enzymatic RNA molecules). In a particular embodiment, a miR gene expression-inhibiting compound can be administered to a subject in combination with one or more additional anti-cancer treatments. Suitable anti-cancer treatments include, but are not limited to, chemotherapy, radiation therapy and combinations thereof (e.g., chemoradiation).

In a certain embodiment, the isolated miR gene product that is deregulated in pancreatic cancer (and which is administered to the subject) is selected from the group consisting of miR-326, miR-155, miR-339, miR-34c, miR-345, miR-152, miR-372, miR-128a and a combination thereof (or an isolated variant or biologically-active fragment of one or more of these miRs). In a particular embodiment, the miR gene product that is administered is not one or more of let7a-2, let-7c, let-7g, let-71, miR-7-2, miR-7-3, miR-9, miR-9-1, miR-10a, miR-15a, miR-15b, miR-16-1, miR-16-2, miR-17-5p, miR-20a, miR-21, miR-24-1, miR-24-2, miR-25, miR-29b-2, miR-30, miR-30a-5p, miR-30c, miR-30d, miR-31, miR-32, miR-34, miR-34a, miR-34a prec, miR-34a-1, miR-34a-2, miR-92-2, miR-96, miR-99a, miR-99b prec, miR-100, miR-103, miR-106a, miR-107, miR-123, miR-124a-1, miR-125b-1, miR-125b-2, miR-126*, miR-127, miR-128b, miR-129, miR-129-1/2 prec, miR-132, miR-135-1, miR-136, miR-137, miR-141, miR-142-as, miR-143, miR-146, miR-148, miR-149, miR-153, miR-155, miR 159-1, miR-181, miR-181b-1, miR-182, miR-186, miR-191, miR-192, miR-195, miR-196-1, miR-196-1 prec, miR-196-2, miR-199a-1, miR-199a-2, miR-199b, miR-200b, miR-202, miR-203, miR-204, miR-205, miR-210, miR-211, miR-212, miR-214, miR-215, miR-217, miR-221 and/or miR-223.

As described, when the at least one isolated miR gene product is upregulated in cancer cells, the method comprises administering to the subject an effective amount of at least one compound for inhibiting expression of the at least one miR gene product, such that proliferation of pancreatic cancer cells is inhibited. In one embodiment, the compound for inhibiting expression of the at least one miR gene product inhibits a miR gene product selected from the group consisting of miR-103-2, miR-107, miR-103-1, miR-342, miR-100, miR-24-2, miR-23a, miR-125a, miR-26a-1, miR-24-1, miR-191, miR-1Sa, miR-368, miR-26b, miR-125b-2, miR-125b-1, miR-26a-2, miR-335, miR-126, miR-1-2, miR-21, miR-25, miR-92-2, miR-130a, miR-93, miR-16-1, miR-145, miR-17, miR-99b, miR-181b-1, miR-146, miR-181b-2, miR-16-2, miR-99a, miR-197, miR-10a, miR-224, miR-92-1, miR-27a, miR-221, miR-320, miR-7-1, miR-29b-2, miR-150, miR-30d, miR-29a, miR-23b, miR-135a-2, miR-223, miR-3p21-v, miR-128b, miR-30b, miR-29b-1, miR-106b, miR-132, miR-214, miR-7-3, miR-29c, miR-367, miR-30c-2, miR-27b, miR-140, miR-10b, miR-20, miR-129-1, miR-340, miR-30a, miR-30c-1, miR-106a, miR-32, miR-95, miR-222, miR-30e, miR-129-2, miR-345, miR-143, miR-182, miR-1-1, miR-133a-1, miR-200c, miR-194-1, miR-210, miR-181c, miR-192, miR-220, miR-213, miR-323, miR-375 and a combination thereof.

In a related embodiment, the methods of treating pancreatic cancer in a subject additionally comprise the step of first determining the amount of at least one miR gene product in pancreatic cancer cells from the subject, and comparing that level of the miR gene product to the level of a corresponding miR gene product in control cells. If expression of the miR gene product is deregulated (e.g., downregulated, upregulated) in pancreatic cancer cells, the methods further comprise altering the amount of the at least one miR gene product expressed in the pancreatic cancer cells. In one embodiment, the amount of the miR gene product expressed in the cancer cells is less than the amount of the miR gene product expressed in control cells, and an effective amount of the miR gene product, or an isolated variant or biologically-active fragment thereof, is administered to the subject. In another embodiment, the amount of the miR gene product expressed in the cancer cells is greater than the amount of the miR gene product expressed in control cells, and an effective amount of at least one compound for inhibiting expression of the at least one miR gene is administered to the subject. Suitable miRs and compounds that inhibit expression of miR genes include, for example, those described herein.

The terms "treat", "treating" and "treatment", as used herein, refer to ameliorating symptoms associated with a disease or condition, for example, pancreatic cancer, including preventing or delaying the onset of the disease symptoms, and/or lessening the severity or frequency of symptoms of the disease or condition. The terms "subject", "patient" and "individual" are defined herein to include animals, such as mammals, including, but not limited to, primates, cows, sheep, goats, horses, dogs, cats, rabbits, guinea pigs, rats, mice or other bovine, ovine, equine, canine, feline, rodent, or murine species. In a preferred embodiment, the animal is a human.

As used herein, an "effective amount" of an isolated miR gene product is an amount sufficient to inhibit proliferation of a cancer cell in a subject suffering from; pancreatic cancer. One skilled in the art can readily determine an effective amount of a miR gene product to be administered to a given subject, by taking into account factors, such as the size and weight of the subject; the extent of disease penetration; the age, health and sex of the subject; the route of administration; and whether the administration is regional or systemic.

For example, an effective amount of an isolated miR gene product can be based on the approximate weight of a tumor mass to be treated. The approximate weight of a tumor mass can be determined by calculating the approximate volume of the mass, wherein one cubic centimeter of volume is roughly equivalent to one gram. An effective amount of the isolated miR gene product based on the weight of a tumor mass can be in the range of about 10-500 micrograms/gram of tumor mass. In certain embodiments, the tumor mass can be at least about 10 micrograms/gram of tumor mass, at least about 60 micrograms/gram of tumor mass or at least about 100 micrograms/gram of tumor mass.

An effective amount of an isolated miR gene product can also be based on the approximate or estimated body weight of a subject to be treated. Preferably, such effective amounts are administered parenterally or enterally, as described herein. For example, an effective amount of the isolated miR gene product that is administered to a subject can range from about 5-3000 micrograms/kg of body weight, from about 700-1000 micrograms/kg of body weight, or greater than about 1000 micrograms/kg of body weight.

One skilled in the art can also readily determine an appropriate dosage regimen for the administration of an isolated miR gene product to a given subject. For example, a miR gene product can be administered to the subject once (e.g., as a single injection or deposition). Alternatively, a miR gene product can be administered once or twice daily to a subject for a period of from about three to about twenty-eight days, more particularly from about seven to about ten days. In a particular dosage regimen, a miR gene product is administered once a day for seven days. Where a dosage regimen comprises multiple administrations, it is understood that the effective amount of the miR gene product administered to the subject can comprise the total amount of gene product administered over the entire dosage regimen.

As used herein, an "isolated" miR gene product is one that is synthesized, or altered or removed from the natural state through human intervention. For example, a synthetic miR gene product, or a miR gene product partially or completely separated from the coexisting materials of its natural state, is considered to be "isolated." An isolated miR gene product can exist in a substantially-purified form, or can exist in a cell into which the miR gene product has been delivered. Thus, a miR gene product that is deliberately delivered to, or expressed in, a cell is considered an "isolated" miR gene product. A miR gene product produced inside a cell from a miR precursor molecule is also considered to be an "isolated" molecule. According to the invention, the isolated miR gene products described herein can be used for the manufacture of a medicament for treating pancreatic cancer in a subject (e.g., a human).

Isolated miR gene products can be obtained using a number of standard techniques. For example, the miR gene products can be chemically synthesized or recombinantly produced using methods known in the art. In one embodiment, miR gene products are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., U.S.A.), Pierce Chemical (part of Perbio Science, Rockford, Ill., U.S.A.), Glen Research (Sterling, Va., U.S.A.), ChemGenes (Ashland, Mass., U.S.A.) and Cruachem (Glasgow, UK).

Alternatively, the miR gene products can be expressed from recombinant circular or linear DNA plasmids using any suitable promoter. Suitable promoters for expressing RNA from a plasmid include, e.g., the U6 or H1 RNA pol III promoter sequences, or the cytomegalovirus promoters. Selection of other suitable promoters is within the skill in the art. The recombinant plasmids of the invention can also comprise inducible or regulatable promoters for expression of the miR gene products in cancer cells.

The miR gene products that are expressed from recombinant plasmids can be isolated from cultured cell expression systems by standard techniques. The miR gene products that are expressed from recombinant plasmids can also be delivered to, and expressed directly in, the cancer cells. The use of recombinant plasmids to deliver the miR gene products to cancer cells is discussed in more detail below.

The miR gene products can be expressed from a separate recombinant plasmid, or they can be expressed from the same recombinant plasmid. In one embodiment, the miR gene products are expressed as RNA precursor molecules from a single plasmid; and the precursor molecules are processed into the functional miR gene product by a suitable processing system, including, but not limited to, processing systems extant within a cancer cell. Other suitable processing systems include, e.g., the in vitro *Drosophila* cell lysate system (e.g., as described in U.S. Published Patent Application No. 2002/0086356 to Tuschl et al., the entire disclosure of which is incorporated herein by reference) and the *E. coli* RNAse III system (e.g., as described in U.S. Published Patent Application No. 2004/0014113 to Yang et al., the entire disclosure of which is incorporated herein by reference).

Selection of plasmids suitable for expressing the miR gene products, methods for inserting nucleic acid sequences into the plasmid to express the gene products, and methods of delivering the recombinant plasmid to the cells of interest are within the skill in the art. See, for example, Zeng et al. (2002), *Molecular Cell* 9:1327-1333; Tuschl (2002), *Nat. Biotechnol*, 20:446-448; Brummelkamp et al. (2002), *Science* 296:550-553; Miyagishi et al. (2002), *Nat. Biotechnol.* 20:497-500; Paddison et al. (2002), *Genes Dev.* 16:948-958; Lee et al. (2002), *Nat. Biotechnol.* 20:500-505; and Paul et al. (2002), *Nat. Biotechnol.* 20:505-508, the entire disclosures of which are incorporated herein by reference.

In one embodiment, a plasmid expressing the miR gene products comprises a sequence encoding a miR precursor RNA under the control of the CMV intermediate-early promoter. As used herein, "under the control" of a promoter means that the nucleic acid sequences encoding the miR gene product are located 3' of the promoter, so that the promoter can initiate transcription of the miR gene product coding sequences.

The miR gene products can also be expressed from recombinant viral vectors. It is contemplated that the miR gene products can be expressed from two separate recombinant viral vectors, or from the same viral vector. The RNA expressed from the recombinant viral vectors can either be isolated from cultured cell expression systems by standard techniques, or can be expressed directly in cancer cells. The use of recombinant viral vectors to deliver the miR gene products to cancer cells is discussed in more detail below.

The recombinant viral vectors of the invention comprise sequences encoding the miR gene products and any suitable promoter for expressing the RNA sequences. Suitable promoters include, but are not limited to, the U6 or H1 RNA pol III promoter sequences, or the cytomegalovirus promoters. Selection of other suitable promoters is within the skill in the art. The recombinant viral vectors of the invention can also comprise inducible or regulatable promoters for expression of the miR gene products in a cancer cell.

Any viral vector capable of accepting the coding sequences for the miR gene products can be used; for example, vectors derived from adenovirus (AV); adeno-associated virus (AAV); retroviruses (e.g., lentiviruses (LV), Rhabdoviruses, murine leukemia virus); herpes virus, and the like. The tropism of the viral vectors can be modified by pseudotyping the vectors with envelope proteins or other surface antigens from other viruses, or by substituting different viral capsid proteins, as appropriate.

For example, lentiviral vectors of the invention can be pseudotyped with surface proteins from vesicular stomatitis virus (VSV), rabies, Ebola, Mokola, and the like. AAV vectors of the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors that express different capsid protein serotypes are within the skill in the art; see, e.g., Rabinowitz, J. E., et al (2002), *J. Virol.* 76:791-801, the entire disclosure of which is incorporated herein by reference.

Selection of recombinant viral vectors suitable for use in the invention, methods for inserting nucleic acid sequences for expressing RNA into the vector, methods of delivering the viral vector to the cells of interest, and recovery of the expressed RNA products are within the skill in the art. See, for example, Dornburg (1995), *Gene Therapy* 2:301-310; Eglitis (1988), *Biotechniques* 6:608-614; Miller (1990), *Hum. Gene Therapy* 1:5-14; and Anderson (1998), *Nature* 392:25-30, the entire disclosures of which are incorporated herein by reference.

Particularly suitable viral vectors are those derived from AV and AAV. A suitable AV vector for expressing the miR gene products, a method for constructing the recombinant AV vector, and a method for delivering the vector into target cells, are described in Xia et al. (2002), *Nat. Biotech.* 20:1006-1010, the entire disclosure of which is incorporated herein by reference. Suitable AAV vectors for expressing the miR gene products, methods for constructing the recombinant AAV vector, and methods for delivering the vectors into target cells are described in Samulski et al. (1987), *J. Virol.* 61:3096-3101; Fisher et al. (1996), *J. Virol.*, 70:520-532; Samulski et al. (1989), *J. Virol.* 63:3822-3826; U.S. Pat. No. 5,252,479; U.S. Pat. No. 5,139,941; International Patent Application No. WO 94/13788; and International Patent Application No. WO 93/24641, the entire disclosures of which are incorporated herein by reference. In one embodiment, the miR gene products are expressed from a single recombinant AAV vector comprising the CMV intermediate early promoter.

In a certain embodiment, a recombinant AAV viral vector of the invention comprises a nucleic acid sequence encoding a miR precursor RNA in operable connection with a polyT termination sequence under the control of a human U6 RNA promoter. As used herein, "in operable connection with a polyT termination sequence" means that the nucleic acid sequences encoding the sense or antisense strands are immediately adjacent to the polyT termination signal in the 5' direction. During transcription of the miR sequences from the vector, the polyT termination signals act to terminate transcription.

In other embodiments of the treatment methods of the invention, an effective amount of at least one compound that inhibits miR expression can be administered to the subject. As used herein, "inhibiting miR expression" means that the production of the precursor and/or active, mature form of miR gene product after treatment is less than the amount produced prior to treatment. One skilled in the art can readily determine whether miR expression has been inhibited in a cancer cell, using, for example, the techniques for determining miR transcript level discussed herein. Inhibition can occur at the level of gene expression (i.e., by inhibiting transcription of a miR gene encoding the miR gene product) or at the level of processing (e.g., by inhibiting processing of a miR precursor into a mature, active miR).

As used herein, an "effective amount" of a compound that inhibits miR expression is an amount sufficient to inhibit proliferation of a cancer cell in a subject suffering from a cancer (e.g., pancreatic cancer). One skilled in the art can readily determine an effective amount of a miR expression-inhibiting compound to be administered to a given subject, by taking into account factors, such as the size and weight of the subject; the extent of disease penetration; the age, health and sex of the subject; the route of administration; and whether the administration is regional or systemic.

For example, an effective amount of the expression-inhibiting compound can be based on the approximate weight of a tumor mass to be treated, as described herein. An effective amount of a compound that inhibits miR expression can also be based on the approximate or estimated body weight of a subject to be treated, as described herein.

One skilled in the art can also readily determine an appropriate dosage regimen for administering a compound that inhibits miR expression to a given subject, as described herein. Suitable compounds for inhibiting miR gene expression include double-stranded RNA (such as short- or small-interfering RNA or "siRNA"), antisense nucleic acids, and enzymatic RNA molecules, such as ribozymes. Each of these compounds can be targeted to a given miR gene product and interfere with the expression (e.g., by inhibiting translation, by inducing cleavage and/or degradation) of the target miR gene product.

For example, expression of a given miR gene can be inhibited by inducing RNA interference of the miR gene with an isolated double-stranded RNA ("dsRNA") molecule which has at least 90%, for example at least 95%, at least 98%, at least 99%, or 100%, sequence homology with at least a portion of the miR gene product. In a particular embodiment, the dsRNA molecule is a "short or small interfering RNA" or "siRNA."

siRNA useful in the present methods comprise short double-stranded RNA from about 17 nucleotides to about 29 nucleotides in length, preferably from about 19 to about 25 nucleotides in length. The siRNA comprise a sense RNA strand and a complementary antisense RNA strand annealed together by standard Watson-Crick base-pairing interactions (hereinafter "base-paired"). The sense strand comprises a nucleic acid sequence that is substantially identical to a nucleic acid sequence contained within the target miR gene product.

As used herein, a nucleic acid sequence in an siRNA that is "substantially identical" to a target sequence contained within the target mRNA is a nucleic acid sequence that is identical to the target sequence, or that differs from the target sequence by one or two nucleotides. The sense and antisense strands of the siRNA can comprise two complementary, single-stranded RNA molecules, or can comprise a single molecule in which two complementary portions are base-paired and are covalently linked by a single-stranded "hairpin" area.

The siRNA can also be altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, or modifications that make the siRNA resistant to nuclease digestion, or the substitution of one or more nucleotides in the siRNA with deoxyribonucleotides.

One or both strands of the siRNA can also comprise a 3' overhang. As used herein, a "3' overhang" refers to at least one unpaired nucleotide extending from the 3'-end of a duplexed RNA strand. Thus, in certain embodiments, the siRNA comprises at least one 3' overhang of from 1 to about 6 nucleotides (which includes ribonucleotides or deoxyribonucleotides) in length, from 1 to about 5 nucleotides in length, from 1 to about 4 nucleotides in length, or from about 2 to about 4 nucleotides in length. In a particular embodiment, the 3' overhang is present on both strands of the siRNA, and is 2 nucleotides in length. For example, each strand of the siRNA can comprise 3' overhangs of dithymidylic acid ("TT") or diuridylic acid ("uu").

The siRNA can be produced chemically or biologically, or can be expressed from a recombinant plasmid or viral vector, as described above for the isolated miR gene products. Exemplary methods for producing and testing dsRNA or siRNA molecules are described in U.S. Published Patent Application No. 2002/0173478 to Gewirtz and in U.S. Published Patent Application No. 2004/0018176 to Reich et al., the entire disclosures of both of which are incorporated herein by reference.

Expression of a given miR gene can also be inhibited by an antisense nucleic acid. As used herein, an "antisense nucleic acid" refers to a nucleic acid molecule that binds to target RNA by means of RNA-RNA, RNA-DNA or RNA-peptide nucleic acid interactions, which alters the activity of the target RNA. Antisense nucleic acids suitable for use in the present methods are single-stranded nucleic acids (e.g., RNA, DNA, RNA-DNA chimeras, peptide nucleic acids (PNA)) that generally comprise a nucleic acid sequence complementary to a contiguous nucleic acid sequence in a miR gene product. The antisense nucleic acid can comprise a nucleic acid sequence that is 50-100% complementary, 75-100% complementary, or 95-100% complementary to a contiguous nucleic acid sequence in a miR gene product. Nucleic acid sequences of particular human miR gene products are provided in Table 1a and Table 1b. Without wishing to be bound by any theory, it is believed that the antisense nucleic acids activate RNase H or another cellular nuclease that digests the miR gene product/antisense nucleic acid duplex.

Antisense nucleic acids can also contain modifications to the nucleic acid backbone or to the sugar and base moieties (or their equivalent) to enhance target specificity, nuclease resistance, delivery or other properties related to efficacy of the molecule. Such modifications include cholesterol moieties, duplex intercalators, such as acridine, or one or more nuclease-resistant groups.

Antisense nucleic acids can be produced chemically or biologically, or can be expressed from a recombinant plasmid or viral vector, as described above for the isolated miR gene products. Exemplary methods for producing and testing are within the skill in the art; see, e.g., Stein and Cheng (1993), *Science* 261:1004 and U.S. Pat. No. 5,849,902 to Woolf et al., the entire disclosures of which are incorporated herein by reference.

Expression of a given miR gene can also be inhibited by an enzymatic nucleic acid. As used herein, an "enzymatic nucleic acid" refers to a nucleic acid comprising a substrate binding region that has complementarity to a contiguous nucleic acid sequence of a miR gene product, and which is able to specifically cleave the miR gene product. The enzymatic nucleic acid substrate binding region can be, for example, 50-100% complementary, 75-100% complementary, or 95-100% complementary to a contiguous nucleic acid sequence in a miR gene product. The enzymatic nucleic acids can also comprise modifications at the base, sugar, and/or phosphate groups. An exemplary enzymatic nucleic acid for use in the present methods is a ribozyme.

The enzymatic nucleic acids can be produced chemically or biologically, or can be expressed from a recombinant plasmid or viral vector, as described above for the isolated miR gene products. Exemplary methods for producing and testing dsRNA or siRNA molecules are described in Werner and Uhlenbeck (1995), *Nucleic Acids Res.* 23:2092-96; Hammann et al. (1999), *Antisense and Nucleic Acid Drug Dev.* 9:25-31; and U.S. Pat. No. 4,987,071 to Cech et al, the entire disclosures of which are incorporated herein by reference.

Administration of at least one miR gene product, or at least one compound for inhibiting miR expression, will inhibit the proliferation of cancer cells in a subject who has a cancer (e.g., pancreatic cancer). As used herein, to "inhibit the proliferation of a cancer cell" means to kill the cell, or permanently or temporarily arrest or slow the growth of the cell. Inhibition of cancer cell proliferation can be inferred if the number of such cells in the subject remains constant or decreases after administration of the miR gene products or miR gene expression-inhibiting compounds. An inhibition of cancer cell proliferation can also be inferred if the absolute number of such cells increases, but the rate of tumor growth decreases.

The number of cancer cells in the body of a subject can be determined by direct measurement, or by estimation from the size of primary or metastatic tumor masses. For example, the number of cancer cells in a subject can be measured by immunohistological methods, flow cytometry, or other techniques designed to detect characteristic surface markers of cancer cells.

The size of a tumor mass can be ascertained by direct visual observation, or by diagnostic imaging methods, such as X-ray, magnetic resonance imaging, ultrasound, and scintigraphy. Diagnostic imaging methods used to ascertain size of the tumor mass can be employed with or without contrast agents, as is known in the art. The size of a tumor mass can also be ascertained by physical means, such as palpation of the tissue mass or measurement of the tissue mass with a measuring instrument, such as a caliper.

The miR gene products or miR gene expression-inhibiting compounds can be administered to a subject by any means suitable for delivering these compounds to cancer cells of the subject. For example, the miR gene products or miR expression-inhibiting compounds can be administered by methods suitable to transfect cells of the subject with these compounds, or with nucleic acids comprising sequences encoding these compounds. In one embodiment, the cells are transfected with a plasmid or viral vector comprising sequences encoding at least one miR gene product or miR gene expression-inhibiting compound.

Transfection methods for eukaryotic cells are well known in the art, and include, e.g., direct injection of the nucleic acid into the nucleus or pronucleus of a cell; electroporation; liposome transfer or transfer mediated by lipophilic materials; receptor-mediated nucleic acid delivery, bioballistic or particle acceleration; calcium phosphate precipitation, and transfection mediated by viral vectors.

For example, cells can be transfected with a liposomal transfer compound, e.g., DOTAP (N-[1-(2,3-dioleoyloxy) propyl]-N,N,N-trimethyl-ammonium methylsulfate, Boehringer-Mannheim) or an equivalent, such as LIPOFECTIN. The amount of nucleic acid used is not critical to the practice of the invention; acceptable results may be achieved with 0.1-100 micrograms of nucleic acid/$10^5$ cells. For example, a ratio of about 0.5 micrograms of plasmid vector in 3 micrograms of DOTAP per $10^5$ cells can be used.

A miR gene product or miR gene expression-inhibiting compound can also be administered to a subject by any suitable enteral or parenteral administration route. Suitable enteral administration routes for the present methods include, e.g., oral, rectal, or intranasal delivery. Suitable parenteral administration routes include, e.g., intravascular administration (e.g., intravenous bolus injection, intravenous infusion, intra-arterial bolus injection, intra-arterial infusion and catheter instillation into the vasculature); peri- and intra-tissue injection (e.g., peri-tumoral and intra-tumoral injection, intra-retinal injection, or subretinal injection); subcutaneous injection or deposition, including subcutaneous infusion (such as by osmotic pumps); direct application to the tissue of interest, for example by a catheter or other placement device (e.g., a retinal pellet or a suppository or an implant comprising a porous, non-porous, or gelatinous material); and inhalation. Particularly suitable administration routes are injection, infusion and direct injection into the tumor.

In the present methods, a miR gene product or miR gene product expression-inhibiting compound can be administered to the subject either as naked RNA, in combination with a delivery reagent, or as a nucleic acid (e.g., a recombinant plasmid or viral vector) comprising sequences that express the miR gene product or miR gene expression-inhibiting compound. Suitable delivery reagents include, e.g., the Mirus Transit TKO lipophilic reagent; LIPOFECTIN; lipofectamine; cellfectin; polycations (e.g., polylysine) and liposomes.

Recombinant plasmids and viral vectors comprising sequences that express the miR gene products or miR gene expression-inhibiting compounds, and techniques for delivering such plasmids and vectors to cancer cells, are discussed herein and/or are well known in the art.

In a particular embodiment, liposomes are used to deliver a miR gene product or miR gene expression-inhibiting compound (or nucleic acids comprising sequences encoding them) to a subject. Liposomes can also increase the blood half-life of the gene products or nucleic acids. Suitable liposomes for use in the invention can be formed from standard vesicle-forming lipids, which generally include neutral or negatively charged phospholipids and a sterol, such as cholesterol. The selection of lipids is generally guided by consideration of factors, such as the desired liposome size and half-life of the liposomes in the blood stream. A variety of methods are known for preparing liposomes, for example, as described in Szoka et al. (1980), *Ann. Rev. Biophys. Bioeng.* 9:467; and U.S. Pat. Nos. 4,235,871, 4,501,728, 4,837,028, and 5,019,369, the entire disclosures of which are incorporated herein by reference.

The liposomes for use in the present methods can comprise a ligand molecule that targets the liposome to cancer cells. Ligands that bind to receptors prevalent in cancer cells, such as monoclonal antibodies that bind to tumor cell antigens, are preferred.

The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the liposome structure. In a particularly preferred embodiment, a liposome of the invention can comprise both an opsonization-inhibition moiety and a ligand.

Opsonization-inhibiting moieties for use in preparing the liposomes of the invention are typically large hydrophilic polymers that are bound to the liposome membrane. As used herein, an opsonization-inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES; e.g., as described in U.S. Pat. No. 4,920,016, the entire disclosure of which is incorporated herein by reference.

Opsonization-inhibiting moieties suitable for modifying liposomes are preferably water-soluble polymers with a number-average molecular weight from about 500 to about 40,000 daltons, and more preferably from about 2,000 to about 20,000 daltons. Such polymers include polyethylene glycol (PEG) or polypropylene glycol (PPG) or derivatives thereof; e.g., methoxy PEG or PPG, and PEG or PPG stearate; synthetic polymers, such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization-inhibiting polymer can be a block copolymer of PEG and either a polyamino acid, polysaccharide, polyamidoamine, polyethyleneamine, or polynucleotide. The opsonization-inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups. Preferably, the opsonization-inhibiting moiety is a PEG, PPG, or a derivative thereof. Liposomes modified with PEG or PEG-derivatives are sometimes called "PEGylated liposomes."

The opsonization-inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using $Na(CN)BH_3$ and a solvent mixture, such as tetrahydrofuran and water in a 30:12 ratio at 60° C.

Liposomes modified with opsonization-inhibition moieties remain in the circulation much longer than unmodified liposomes. For this reason, such liposomes are sometimes called "stealth" liposomes. Stealth liposomes are known to accumulate in tissues fed by porous or "leaky" microvasculature. Thus, tissue characterized by such microvasculature defects, for example, solid tumors, will efficiently accumulate these liposomes; see Gabizon, et al. (1988), Proc. Natl. Acad. Sci., U.S.A., 18:6949-53. In addition, the reduced uptake by the RES lowers the toxicity of stealth liposomes by preventing significant accumulation of the liposomes in the liver and spleen. Thus, liposomes that are modified with opsonization-inhibition moieties are particularly suited to deliver the miR gene products or miR gene expression-inhibition compounds (or nucleic acids comprising sequences encoding them) to tumor cells.

The miR gene products or miR gene expression-inhibition compounds can be formulated as pharmaceutical compositions, sometimes called "medicaments," prior to administering them to a subject, according to techniques known in the art. Accordingly, the invention encompasses pharmaceutical compositions for treating pancreatic cancer. In one embodiment, the pharmaceutical composition comprises at least one isolated miR gene product, or an isolated variant or biologically-active fragment thereof, and a pharmaceutically-acceptable carrier. In a particular embodiment, the at least one miR gene product corresponds to a miR gene product that has a decreased level of expression in pancreatic cancer cells relative to suitable control cells (i.e., it is downregulated). In a certain embodiment, the isolated miR gene product is selected from the group consisting of miR-326, miR-155, miR-339, miR-34c, miR-345, miR-152, miR-372, miR-128a and a combination thereof. In one embodiment, the isolated miR gene product is not miR-15a or miR-16-1. In an additional embodiment, the miR gene product is not miR-210 or miR-212. In another embodiment, the miR gene product is not miR-21, miR-143, miR-205 or miR-9. In yet another embodiment, the miR gene product is not miR-21, miR-191, miR-126*, miR-210, miR-155, miR-143, miR-205, miR-126, miR-30a-5p, miR-140, miR-214, miR-218-2, miR-145, miR-106a, miR-192, miR-203, miR-150, miR-220, miR-212 or miR-9.

In other embodiments, the pharmaceutical compositions of the invention comprise at least one miR expression-inhibition compound and a pharmaceutically-acceptable carrier. In a particular embodiment, the at least one miR expression-inhibition compound is specific for a miR gene product whose expression is greater in pancreatic cancer cells than control cells (i.e., it is upregulated). In certain embodiments, the miR expression-inhibition compound is specific for one or more miR gene products selected from the group consisting of miR-103-2, miR-107, miR-103-1, miR-342, miR-100, miR-24-2, miR-23a, miR-125a, miR-26a-1, miR-24-1, miR-191, miR-15a, miR-368, miR-26b, miR-125b-2, miR-125b-1, miR-26a-2, miR-335, miR-126, miR-1-2, miR-21, miR-25, miR-92-2, miR-130a, miR-93, miR-16-1, miR-145, miR-17, miR-99b, miR-181b-1, miR-146, miR-181b-2, miR-16-2, miR-99a, miR-197, miR-10a, miR-224, miR-92-1, miR-27a, miR-221, miR-320, miR-7-1, miR-29b-2, miR-150, miR-30d, miR-29a, miR-23b, miR-135a-2, miR-223, miR-3p21-v, miR-128b, miR-30b, miR-29b-1, miR-106b, miR-132, miR-214, miR-7-3, miR-29c, miR-367, miR-30c-2, miR-27b, miR-140, miR-10b, miR-20, miR-129-1, miR-340, miR-30a, miR-30c-1, miR-106a, miR-32, miR-95, miR-222, miR-30e, miR-129-2, miR-345, miR-143, miR-182, miR-1-1, miR-133a-1, miR-200c, miR-194-1, miR-210, miR-181c, miR-192, miR-220, miR-213, miR-323, miR-375 and a combination thereof. In one embodiment, the isolated miR gene product is not specific for miR-15a or miR-16-1. In another embodiment, the miR gene product is not specific for miR-210 or miR-212. In yet another embodiment, the miR gene product is not specific for miR-21, miR-143, miR-205 or miR-9. In still another embodiment, the miR gene product is not specific for miR-21, miR-191, miR-126*, miR-210, miR-155, miR-143, miR-205, miR-126, miR-30a-5p, miR-140, miR-214, miR-218-2, miR-145, miR-106a, miR-192, miR-203, miR-150, miR-220, miR-212 or miR-9.

Pharmaceutical compositions of the present invention are characterized as being at least sterile and pyrogen-free. As used herein, "pharmaceutical compositions" include formulations for human and veterinary use. Methods for preparing pharmaceutical compositions of the invention are within the skill in the art, for example, as described in Remington's Pharmaceutical Science, 17th ed., Mack Publishing Company, Easton, Pa. (1985), the entire disclosure of which is incorporated herein by reference.

The present pharmaceutical compositions comprise at least one miR gene product or miR gene expression-inhibition compound (or at least one nucleic acid comprising a sequence encoding the miR gene product or miR gene expression-inhibition compound) (e.g., 0.1 to 90% by weight), or a physiologically-acceptable salt thereof, mixed with a pharmaceutically-acceptable carrier. In certain embodiments, the pharmaceutical composition of the invention additionally comprises one or more anti-cancer agents (e.g., chemotherapeutic agents). The pharmaceutical formulations of the invention can also comprise at least one miR gene product or miR gene expression-inhibition compound (or at least one nucleic acid comprising a sequence encoding the miR gene product or miR gene expression-inhibition compound), which are encapsulated by liposomes and a pharmaceutically-acceptable carrier. In one embodiment, the pharmaceutical composition comprises a miR gene or gene product that is not miR-15, miR-16, miR-143 and/or miR-145.

Especially suitable pharmaceutically-acceptable carriers are water, buffered water, normal saline, 0.4% saline, 0.3% glycine, hyaluronic acid and the like.

In a particular embodiment, the pharmaceutical compositions of the invention comprise at least one miR gene product or miR gene expression-inhibition compound (or at least one nucleic acid comprising a sequence encoding the miR gene product or miR gene expression-inhibition compound) that is resistant to degradation by nucleases. One skilled in the art can readily synthesize nucleic acids that are nuclease resistant, for example by incorporating one or more ribonucleotides that is modified at the 2'-position into the miR gene product. Suitable 2'-modified ribonucleotides include those modified at the 2'-position with fluoro, amino, alkyl, alkoxy and O-allyl.

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include, e.g., physiologically biocompatible buffers (e.g., tromethamine hydrochloride), additions of chelants (such as, for example, DTPA or DTPA-bisamide) or calcium chelate complexes (such as, for example, calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid pharmaceutical compositions of the invention, conventional nontoxic solid pharmaceutically-acceptable carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can comprise any of the carriers and excipients listed above and 10-95%, preferably 25%-75%, of the at least one miR gene product or miR gene expression-inhibition compound (or at least one nucleic acid comprising sequences encoding them). A pharmaceutical composition for aerosol (inhalational) administration can comprise 0.01-20% by weight, preferably 1%-10% by weight, of the at least one miR gene product or miR gene expression-inhibition compound (or at least one nucleic acid comprising a sequence encoding the miR gene product or miR gene expression-inhibition compound) encapsulated in a liposome as described above, and a propellant. A carrier can also be included as desired; e.g., lecithin for intranasal delivery.

The pharmaceutical compositions of the invention can further comprise one or more anti-cancer agents. In a particular embodiment, the compositions comprise at least one miR gene product or miR gene expression-inhibition compound (or at least one nucleic acid comprising a sequence encoding the miR gene product or miR gene expression-inhibition compound) and at least one chemotherapeutic agent. Chemotherapeutic agents that are suitable for the methods of the invention include, but are not limited to, DNA-alkylating agents, anti-tumor antibiotic agents, anti-metabolic agents, tubulin stabilizing agents, tubulin destabilizing agents, hormone antagonist agents, topoisomerase inhibitors, protein kinase inhibitors, HMG-CoA inhibitors, CDK inhibitors, cyclin inhibitors, caspase inhibitors, metalloproteinase inhibitors, antisense nucleic acids, triple-helix DNAs, nucleic acids aptamers, and molecularly-modified viral, bacterial and exotoxic agents. Examples of suitable agents for the compositions of the present invention include, but are not limited to, cytidine arabinoside, methotrexate, vincristine, etoposide (VP-16), doxorubicin (adriamycin), cisplatin (CDDP), dexamethasone, arglabin, cyclophosphamide, sarcolysin, methylnitrosourea, fluorouracil, 5-fluorouracil (5FU), vinblastine, camptothecin, actinomycin-D, mitomycin C, hydrogen peroxide, oxaliplatin, irinotecan, topotecan, leucovorin, carmustine, streptozocin, CPT-11, taxol, tamoxifen, dacarbazine, rituximab, daunorubicin, 1-β-D-arabinofuranosylcytosine, imatinib, fludarabine, docetaxel and FOLFOX4.

The invention also encompasses methods of identifying an anti-pancreatic cancer agent, comprising providing a test agent to a cell and measuring the level of at least one miR gene product in the cell. In one embodiment, the method comprises providing a test agent to a cell and measuring the level of at least one miR gene product associated with decreased expression levels in pancreatic cancer cells. An increase in the level of the miR gene product in the cell, relative to a to a suitable control (e.g., the level of the miR gene product in a control cell), is indicative of the test agent being an anti-pancreatic cancer agent. In a particular embodiment, the at least one miR gene product associated with decreased expression levels in pancreatic cancer cells is selected from the group consisting of miR-326, miR-155, miR-339, miR-34c, miR-345, miR-152, miR-372, miR-128a and a combination thereof. In one embodiment, the miR gene product is not one or more of let7a-2, let-7c, let-7g, let-71, miR-7-2, miR-7-3, miR-9, miR-9-1, miR-10a, miR-15a, miR-15b, miR-16-1, miR-16-2, miR-17-5p, miR-20a, miR-21, miR-24-1, miR-24-2, miR-25, miR-29b-2, miR-30, miR-30a-5p, miR-30c, miR-30d, miR-31, miR-32, miR-34, miR-34a, miR-34a prec, miR-34a-1, miR-34a-2, miR-92-2, miR-96, miR-99a, miR-99b prec, miR-100, miR-103, miR-106a, miR-107, miR-123, miR-124a-1, miR-125b-1, miR-125b-2, miR-126*, miR-127, miR-128b, miR-129, miR-129-1/2 prec, miR-132, miR-135-1, miR-136, miR-137, miR-141, miR-142-as, miR-143, miR-146, miR-148, miR-149, miR-153, miR-155, miR 159-1, miR-181, miR-181b-1, miR-182, miR-186, miR-191, miR-192, miR-195, miR-196-1, miR-196-1 prec, miR-196-2, miR-199a-1, miR-199a-2, miR-199b, miR-200b, miR-202, miR-203, miR-204, miR-205, miR-210, miR-211, miR-212, miR-214, miR-215, miR-217, miR-221 and/or miR-223.

In other embodiments, the method comprises providing a test agent to a cell and measuring the level of at least one miR gene product associated with increased expression levels in pancreatic cancer cells. A decrease in the level of the miR gene product associated with increased expression levels in pancreatic cancer in the cell, relative to a suitable control (e.g., the level of the miR gene product in a control cell), is indicative of the test agent being an anti-pancreatic cancer agent. In a particular embodiment, the at least one miR gene product associated with increased expression levels in pancreatic cancer cells is selected from the group consisting of miR-103-2, miR-107, miR-103-1, miR-342, miR-100, miR-24-2, miR-23a, miR-125a, miR-26a-1, miR-24-1, miR-191, miR-15a, miR-368, miR-26b, miR-125b-2, miR-125b-1, miR-26a-2, miR-335, miR-126, miR-1-2, miR-21, miR-25, miR-92-2, miR-130a, miR-93, miR-16-1, miR-145, miR-17, miR-99b, miR-181b-1, miR-146, miR-181b-2, miR-16-2, miR-99a, miR-197, miR-10a, miR-224, miR-92-1, miR-27a, miR-221, miR-320, miR-7-1, miR-29b-2, miR-150, miR-30d, miR-29a, miR-23b, miR-135a-2, miR-223, miR-3p21-v, miR-128b, miR-30b, miR-29b-1, miR-106b, miR-132, miR-214, miR-7-3, miR-29c, miR-367, miR-30c-2, miR-27b, miR-140, miR-10b, miR-20, miR-129-1, miR-340, miR-30a, miR-30c-1, miR-106a, miR-32, miR-95, miR-222, miR-30e, miR-129-2, miR-345, miR-143, miR-182, miR-1-1, miR-133a-1, miR-200c, miR-194-1, miR-210, miR-181c, miR-192, miR-220, miR-213, miR-323, miR-375 and a combination thereof. In one embodiment, the miR gene product is not one or more of let7a-2, let-7c, let-7g, let-71, miR-7-2, miR-7-3, miR-9, miR-9-1, miR-10a, miR-15a, miR-15b, miR-16-1, miR-16-2, miR-17-5p, miR-20a, miR-21, miR-24-1, miR-24-2, miR-25, miR-29b-2, miR-30, miR-30a-5p, miR-30c, miR-30d, miR-31, miR-32, miR-34, miR-34a, miR-34a prec, miR-34a-1, miR-34a-2, miR-92-2, miR-96, miR-99a, miR-99b prec, miR-100, miR-103, miR-106a, miR-107, miR-123, miR-124a-1, miR-125b-1, miR-125b-2, miR-126*, miR-127, miR-128b, miR-129, miR-129-1/2 prec, miR-132, miR-135-1, miR-136, miR-137, miR-141, miR-142-as, miR-143, miR-146, miR-148, miR-149, miR-153, miR-155, miR 159-1, miR-181, miR-181b-1, miR-182, miR-186, miR-191, miR-192, miR-195, miR-196-1, miR-196-1 prec, miR-196-2, miR-199a-1, miR-199a-2, miR-199b, miR-200b, miR-202, miR-203, miR-204, miR-205, miR-210, miR-211, miR-212, miR-214, miR-215, miR-217, miR-221 and/or miR-223.

Suitable agents include, but are not limited to drugs (e.g., small molecules, peptides), and biological macromolecules (e.g., proteins, nucleic acids). The agent can be produced recombinantly, synthetically, or it may be isolated (i.e., purified) from a natural source. Various methods for providing such agents to a cell (e.g., transfection) are well known in the art, and several of such methods are described hereinabove. Methods for detecting the expression of at least one miR gene product (e.g., Northern blotting, in situ hybridization, RT-PCR, expression profiling) are also well known in the art. Several of these methods are also described herein.

The invention will now be illustrated by the following non-limiting examples.

Exemplification

Materials and Methods

Patient Data, Neoplastic-Cell Enrichment and RNA Extraction.

The clinicopathological characteristics of 40 PET and four PACC, retrieved from the frozen tissue bank of the Pathology Department of the University of Verona, Italy, are reported in Table 2. All tumors were sporadic, as assessed by personal and family histories obtained by direct interview of patients. PET were diagnosed by histopathologic and cell marker analysis, and classified according to WHO criteria (Kloppel, G., et al., "The Gastroenteropancreatic Neuroendocrine Cell System and Its Tumors: The WHO Classification.", *Ann. N.Y. Acad. Sci.* 1014:13-27 (2004)). They included 28 nonfunctional and 12 functional tumors. The 28 NF-PET included 11 well-differentiated endocrine tumors (WDET) and 18 well differentiated endocrine carcinomas (WDEC). The 12 F-PET were insulinomas, comprising 11 WDET and 1 WDEC. WDET were considered with either benign or uncertain biological behavior in accordance with the WHO criteria, that considers tumor size, Ki-67 proliferation index and vascular invasion (Table 2). Diagnosis of PACC was confirmed by immunohistochemical expression of lipase, amylase and trypsin in neoplastic cells. As a control, normal pancreas was taken in 12 corresponding patient specimens.

A neoplastic cellularity of more than 90% was obtained in all cases by microdissection or cryostat enrichment. Total RNA was extracted with Trizol (Invitrogen, Carlsbad, Calif.) according to the manufacturer's instructions from at least ten 20-30 μm thick cryostat sections, checking the cell composition of the sample every five sections. The integrity of total RNA was confirmed in each case using the Agilent 2100 Bioanalyzer (Agilent Technologies, Palo Alto, Calif.).

TABLE 2

Clinicopathological data of the pancreatic endocrine and acinar tumors.

| Case[a] | Sex | Age | Size (cm) | Diagnosis[b] | Invasion[c] | Metastases LN[f] | Liver | Vascular invasion | Insulin[d] IHC | Ki67[e] (%) |
|---|---|---|---|---|---|---|---|---|---|---|
| F-K29 | F | 46 | 9 | WDEC | yes | yes | yes | yes | pos-w | 20 |
| F-K11 | F | 46 | 1.5 | WDET-b | no | no | no | no | pos | 2 |
| F-K36 | M | 23 | 1.3 | WDET-b | no | no | no | no | pos-w | 2 |
| F-Q2 | M | 51 | 1.5 | WDET-b | no | no | no | no | pos | 2 |
| F-Q4 | F | 63 | 1.2 | WDET-b | no | no | no | no | pos-w | 1 |
| F-Q6 | M | 51 | 1.3 | WDET-b | no | no | no | no | pos | 1 |
| F-K20 | F | 27 | 5 | WDET-u | no | no | no | no | pos | 5 |
| F-K47 | M | 66 | 2.5 | WDET-u | no | no | no | no | pos-w | 1 |
| F-K66 | M | 33 | 5 | WDET-u | no | no | no | yes | pos-w | 10 |
| F-K69 | M | 67 | 2.5 | WDET-u | no | no | no | no | pos | n.a.[g] |
| F-K80 | F | 35 | 4 | WDET-u | no | no | no | no | pos | 1 |
| F-Q14 | M | 41 | 1.3 | WDET-u | no | no | no | no | pos | 3 |
| NF-K14 | M | 48 | 11 | WDEC | yes | no | no | yes | neg | 5 |
| NF-K15 | M | 44 | 18 | WDEC | yes | yes | no | yes | neg | 20 |
| NF-K16 | M | 48 | 6.5 | WDEC | yes | yes | no | yes | n.a. | 3 |
| NF-K19 | F | 37 | 4 | WDEC | no | yes | no | no | neg | 30 |
| NF-K23 | M | 56 | 7 | WDEC | yes | yes | yes | yes | pos | 5 |
| NF-K25 | F | 60 | 2 | WDEC | yes | no | no | yes | neg | 2 |
| NF-K3 | M | 42 | 4.5 | WDEC | yes | yes | yes | yes | neg | 8 |

TABLE 2-continued

Clinicopathological data of the pancreatic endocrine and acinar tumors.

| Case[a] | Sex | Age | Size (cm) | Diagnosis[b] | Invasion[c] | Metastases LN[f] | Liver | Vascular invasion | Insulin[d] IHC | Ki67[e] (%) |
|---|---|---|---|---|---|---|---|---|---|---|
| NF-K31 | F | 54 | 3 | WDEC | yes | yes | yes | yes | neg | 20 |
| NF-K32 | F | 61 | 4.5 | WDEC | no | no | yes | yes | neg | 15 |
| NF-K37 | F | 35 | 3 | WDEC | no | yes | no | no | neg | 2 |
| NF-K42 | F | 65 | 4.5 | WDEC | yes | yes | no | no | neg | 2 |
| NF-K43 | M | 53 | 4 | WDEC | yes | yes | yes | yes | pos-w | 10 |
| NF-K6 | F | 51 | 12 | WDEC | no | no | yes | yes | neg | 7 |
| NF-K76 | F | 40 | 5.5 | WDEC | no | yes | no | yes | neg | 5 |
| NF-K9 | F | 70 | 5.5 | WDEC | yes | yes | yes | yes | n.a. | 25 |
| NF-Q12 | M | 56 | 4.5 | WDEC | yes | no | no | yes | neg | 2 |
| NF-Q5 | M | 38 | 3 | WDEC | yes | yes | yes | yes | neg | 3 |
| NF-K63 | M | 58 | 1.2 | WDET-b | no | no | no | no | neg | 2 |
| NF-K8 | F | 42 | 1.5 | WDET-b | no | no | no | no | neg | 2 |
| NF-K10 | F | 66 | 1.5 | WDET-u | no | no | no | no | neg | 2 |
| NF-K13 | F | 66 | 2 | WDET-u | no | no | no | no | neg | 2 |
| NF-K2 | M | 68 | 1.5 | WDET-u | no | no | no | yes | n.a. | 1 |
| NF-K24 | F | 49 | 11 | WDET-u | no | no | no | no | neg | 1 |
| NF-K35 | M | 40 | 8 | WDET-u | no | no | no | no | neg | 2 |
| NF-K41 | M | 39 | 3 | WDET-u | no | no | no | yes | neg | 1 |
| NF-K7 | M | 57 | 2 | WDET-u | no | no | no | no | neg | 3 |
| NF-K75 | F | 69 | 2.5 | WDET-u | no | no | no | no | neg | 1 |
| NF-Q13 | F | 65 | 3 | WDET-u | no | no | no | yes | neg | 2 |
| AC-K53 | M | 36 | 7 | ACC | no | no | no | yes | neg | 10 |
| AC-K54 | M | 64 | 5 | ACC | no | no | no | no | neg | 12 |
| AC-K58 | M | 39 | 6 | ACC | yes | yes | no | yes | neg | 15 |
| AC-K60 | M | 52 | 17 | ACC | yes | yes | no | yes | neg | n.a. |

[a]Cases are identified by a random assigned number precede by F or NF if they are functioning or non-functioning endocrine tumors, respectively.
[b]WDEC, well differentiated endocrine carcinoma; WDET-b, well differentiated endocrine tumor with benign behavior; WDET-u, well differentiated endocrine tumor with uncertain biological behavior.
[c]Invasion of peripancreatic fat and/or adjacent organs (e.g. duodenum, choledocus, spleen).
[d]IHC, immunohistochemistry; pos, positive; pos-w, positive with weak signal; neg, negative.
[e]Proliferation index measured by Ki67 immunohistochemistry.
[f]LN, lymph nodes.
[g]n.a., not available.

MicroRNA Microarray Hybridization and Quantification.

MicroRNA labeling and hybridization on microRNA microarray chips were performed as previously described (Liu, C. G., et al., "An Oligonucleotide Microchip for Genome-Wide microRNA Profiling in Human and Mouse Tissues." *Proc. Natl. Acad. Sci. USA* 101:9740-44 (2004)). Briefly, 5 µg of total RNA from each sample was reverse transcribed using biotin end-labeled random octamers. Hybridization was carried out on our custom microRNA microarray chip (OSU-CCC version 2.0), which contains probes for 460 mature microRNAs (235 *Homo sapiens*, 222 *Mus musculus*, and 3 *Arabidopsis thaliana*) spotted in quadruplicate with annotated active sites. Often, more than one probe set exists for a given mature microRNA. Additionally, there are quadruplicate probes corresponding to most pre-microRNA for detecting the microRNA precursor. The microarray also includes probes for several splicing snRNAs, including U6. Hybridization signals were detected with Streptavidin-Alexa647 conjugate and scanned using Axon 4000B. Scan images were quantified using the Genepix 6.0 software (Axon Instruments (now Molecular Devices Corp.), Sunnyvale, Calif.).

Computational Analyses of microRNA Microarray Data.

Most of the analysis and graphics were generated using R software v. 2.0.1 and Bioconductor v. 1.6 packages (Gentleman, R. C., et al., "Bioconductor: Open Software Development for Computational Biology and Bioinformatics." *Genome Biol.* 5:R80 (2004)). Sequentially, the blank and probe controls spots were removed from the dataset of the 56 microRNA microarrays, and the local background was then subtracted from the median signal. Next, the data was normalized using a variance-stabilizing transformation stratified, within each array, by grid in the vsn package. Subsequently, genefilter package was used to remove all the spots whose intensities were lower than $99^{th}$ percentile of the blank spots in all the arrays. The relative hybridization to blank/negative control probes and subsequent Northern analysis indicated that the absolute value of log-transformed signals less than 4.5 are unreliable.

The data obtained were further analyzed by direct two class unpaired comparison using the same package. The tables of differentially expressed microRNAs were obtained applying the input criteria (based on fold-change and delta value) that are specifically reported in their title. In order to increase stringency, microRNA probes were further filtered retaining those that had at least three significant replicas.

Hierarchical cluster analysis was performed using the aggregate values of replicate spots obtained applying Tukey's median polish algorithm. The analysis was done using the first 200 probes with the highest interquartile range, which contained the mature microRNA sequences. The distance metrics used to cluster samples and genes were Pearson correlation and Euclidean distance, respectively. The agglomerative method was the complete-linkage. The output was visualized using Maple Tree (version 0.2.3.2) (www.mapletree.sourceforge.net). All data were submitted using MIAMExpress to the Array Express database.

The level of coordinate expression between microRNAs was measured by Pearson correlation and microRNA genes were assigned to the same cluster when their distance was below 50 kb (Baskerville, S. and D. P. Bartel, "Microarray Profiling of microRNAs Reveals Frequent Coexpression with Neighboring miRNAs and Host Genes." *RNA* 11: 241-47 (2005)). Next, the set of correlation values measured between microRNAs belonging to the same cluster were compared to the set of correlation values measured between each microRNA in a cluster vs. all other microRNAs out of that cluster using Mann-Whitney non-parametric test.

Northern Blotting.

Five µg of total RNAs were run on 15% Criterion precast PAGE/Urea gels (Bio-Rad, Hercules, Calif.), transferred onto Hybond-N+ membrane (Amersham Biosciences, Piscataway, N.J.) and hybridized overnight with $^{32}$P end-labeled DNA probes at 37° C. in ULTRAhyb™-Oligo hybridization buffer (Ambion, Austin, Tex.). Membranes were washed at 37° C. twice for 30 minutes each with 2×SSC/0.5% SDS. The DNA probes were antisense oligonucleotides relative to the mature microRNAs and to 5S RNA as a control. Filters were analyzed using a Typhoon 9410 phoshorimager (Amersham Biosciences, Piscataway, N.J.) and quantified using ImageQuant TL (Amersham Biosciences, Piscataway, N.J.). Blots were stripped by boiling in 0.1% aqueous SDS for five minutes and were reprobed several times.

Results

MicroRNA expression profiles were determined for 12 normal pancreas samples and 44 pancreatic tumors, including 40 PETs and four PACCs, using a custom microarray. This platform was proved to give robust results, as validated by several previous studies (Liu, C. G., et al., *Proc. Natl. Acad. Sci. USA* 101:9740-44 (2004); Calin, G., et al., *New Engl. J. Med.* 353(17):1793-1801 (2005); Iorio, M. V., et al., *Cancer Res.* 65:7065-70 (2005)). Further support was provided by the finding that microRNAs that are physically linked in genomic clusters were coexpressed, confirming that grouped microRNA genes show coordinate expression (Baskerville, S., and D. P. Bartel, *RNA* 11:241-47 (2005); Altuvia, Y., et al., *Nucleic Acids Res.* 33:2697-2706 (2005)).

The unsupervised analysis by hierarchical clustering, using the two hundred most variable microRNAs, showed a common microRNA expression pattern distinguishing pancreatic endocrine and acinar tumors from normal pancreas (FIGS. 1A-1E). Notably, PACCs fell into a unique cluster that was part of the wider cluster including all PETs, while there was no distinctive pattern between insulinomas and NF-PET.

Class comparison analysis confirmed the differential expression of several microRNAs between PACC or PET and normal tissue, while a smaller number of microRNAs were differentially expressed between PET and PACC, as well as between the WDEC subgroup of PET and PACC. In particular, PET showed 87 upregulated and 8 downregulated microRNAs, as compared to normal pancreas (Table 3), while PACC had 30 microRNAs upregulated and 7 downregulated (Table 4). Only ten microRNAs were differentially expressed between PET and PACC (Table 5), and four were unique to WDEC, with respect to PACC (Table 6).

TABLE 3

Differentially-expressed microRNAs between PETs and Normal Bulk Pancreas (FDR: 0% on the 90th percentile and 2-Fold).

| MicroRNA Name | Score (a) | Fold Change | q-value (b) | Accession ID | Chromosome | Active site (c) | microRNA Families (d) |
|---|---|---|---|---|---|---|---|
| Upregulated microRNAs | | | | | | | |
| hsa-mir-103-2 | 12.017 | 14.52 | 0 | MI0000108 | 20p13 | Yes | 20 |
| hsa-mir-107 | 11.885 | 15.94 | 0 | MI0000114 | 10q23.31 | Yes | 20 |
| hsa-mir-103-1 | 11.296 | 14.18 | 0 | MI0000109 | 5q34 | Yes | 20 |
| hsa-mir-342 | 10.970 | 10.09 | 0 | MI0000805 | 14q32.2 | Yes | 186 |
| hsa-mir-100 | 10.277 | 9.71 | 0 | MI0000102 | 11q24.1 | Yes | 17 |
| hsa-mir-24-2 | 10.116 | 6.20 | 0 | MI0000081 | 19p13.12 | Yes | 38 |
| hsa-mir-23a | 9.468 | 7.11 | 0 | MI0000079 | 19p13.12 | Yes | 32 |
| hsa-mir-125a | 9.011 | 7.52 | 0 | MI0000469 | 19q13.41 | Yes | 9 |
| hsa-mir-26a-1 | 8.787 | 5.34 | 0 | MI0000083 | 3p22.3 | Yes | 39 |
| hsa-mir-24-1 | 8.762 | 4.67 | 0 | MI0000080 | 9q22.32 | Yes | 38 |
| hsa-mir-191 | 8.570 | 5.78 | 0 | MI0000465 | 3p21.31 | Yes | 176 |
| hsa-mir-15a | 7.774 | 3.94 | 0 | MI0000069 | 13q14.2 | Yes | 24 |
| hsa-mir-368 | 7.718 | 6.61 | 0 | MI0000776 | 14q32.31 | Yes | 124 |
| hsa-mir-26b | 7.710 | 5.15 | 0 | MI0000084 | 2q35 | Yes | 39 |
| hsa-mir-125b-2 | 7.687 | 6.52 | 0 | MI0000470 | 21q21.1 | Yes | 9 |
| hsa-mir-125b-1 | 7.623 | 8.08 | 0 | MI0000446 | 11q24.1 | Yes | 9 |
| hsa-mir-26a-2 | 7.498 | 5.52 | 0 | MI0000750 | 12q14.1 | Yes | 39 |
| hsa-mir-335 | 7.361 | 2.94 | 0 | MI0000816 | 7q32.2 | Yes | 192 |
| hsa-mir-126 | 7.210 | 6.06 | 0 | MI0000471 | 9q34.3 | Yes | 127 |
| hsa-mir-1-2 | 7.170 | 6.58 | 0 | MI0000437 | 18q11.2 | Yes | 35 |
| hsa-mir-21 | 7.030 | 5.78 | 0 | MI0000077 | 17q23.2 | Yes | 61 |
| hsa-mir-25 | 7.017 | 4.16 | 0 | MI0000082 | 7q22.1 | Yes | 69 |
| hsa-mir-92-2 | 7.005 | 3.86 | 0 | MI0000094 | Xq26.2 | Yes | 30 |
| hsa-mir-130a | 6.985 | 4.32 | 0 | MI0000448 | 11q12.1 | Yes | 50 |
| hsa-mir-93 | 6.971 | 3.56 | 0 | MI0000095 | 7q22.1 | Yes | 2 |
| hsa-mir-16-1 | 6.785 | 4.57 | 0 | MI0000070 | 13q14.2 | Yes | 46 |
| hsa-mir-145 | 6.770 | 4.49 | 0 | MI0000461 | 5q32 | Yes | 70 |
| hsa-mir-17 | 6.759 | 4.03 | 0 | MI0000071 | 13q31.3 | Yes | 2 |
| hsa-mir-99b | 6.681 | 5.91 | 0 | MI0000746 | 19q13.41 | Yes | 17 |
| hsa-mir-181b-1 | 6.645 | 4.80 | 0 | MI0000270 | 1q31.3 | Yes | 44 |
| hsa-mir-146 | 6.639 | 4.29 | 0 | MI0000477 | 5q33.3 | Yes | 109 |
| hsa-mir-181b-2 | 6.613 | 4.45 | 0 | MI0000683 | 9q33.3 | Yes | 44 |
| hsa-mir-16-2 | 6.613 | 3.90 | 0 | MI0000115 | 3q25.33 | Yes | 46 |
| hsa-mir-99a | 6.561 | 4.35 | 0 | MI0000101 | 21q21.1 | Yes | 17 |

TABLE 3-continued

Differentially-expressed microRNAs between PETs and Normal Bulk Pancreas
(FDR: 0% on the 90th percentile and 2-Fold).

| MicroRNA Name | Score (a) | Fold Change | q-value (b) | Accession ID | Chromosome | Active site (c) | microRNA Families (d) |
|---|---|---|---|---|---|---|---|
| hsa-mir-197 | 6.512 | 2.44 | 0 | MI0000239 | 1p13.3 | Yes | 112 |
| hsa-mir-10a | 6.447 | 4.44 | 0 | MI0000266 | 17q21.32 | Yes | 33 |
| hsa-mir-224 | 6.445 | 2.93 | 0 | MI0000301 | Xq28 | Yes | 85 |
| hsa-mir-92-1 | 6.442 | 3.08 | 0 | MI0000093 | 13q31.3 | Yes | 30 |
| hsa-mir-27a | 6.255 | 3.34 | 0 | MI0000085 | 19p13.12 | Yes | 40 |
| hsa-mir-221 | 6.171 | 8.97 | 0 | MI0000298 | Xp11.3 | Yes | 90 |
| hsa-mir-320 | 6.143 | 2.38 | 0 | MI0000542 | 8p21.3 | Yes | 162 |
| hsa-mir-7-1 | 6.133 | 4.84 | 0 | MI0000263 | 9q21.32 | Yes | 12 |
| hsa-mir-29b-2 | 6.110 | 4.07 | 0 | MI0000107 | 1q32.2 | Yes | 8 |
| hsa-mir-150 | 6.033 | 2.63 | 0 | MI0000479 | 19q13.33 | Yes | 178 |
| hsa-mir-30d | 5.930 | 5.11 | 0 | MI0000255 | 8q24.22 | Yes | 28 |
| hsa-mir-29a | 5.930 | 3.87 | 0 | MI0000087 | 7q32.3 | Yes | 8 |
| hsa-mir-23b | 5.803 | 3.02 | 0 | MI0000439 | 9q22.32 | Yes | 32 |
| hsa-mir-135a-2 | 5.675 | 2.86 | 0 | MI0000453 | 12q23.1 | Yes | 31 |
| hsa-mir-223 | 5.580 | 3.46 | 0 | MI0000300 | Xq12 | Yes | 68 |
| hsa-mir-3p21-v | 5.579 | 2.32 | 0 | NA | NA | Yes | NA |
| hsa-mir-128b | 5.557 | 4.35 | 0 | MI0000727 | 3p22.3 | Yes | 51 |
| hsa-mir-30b | 5.551 | 4.25 | 0 | MI0000441 | 8q24.22 | Yes | 27 |
| hsa-mir-29b-1 | 5.456 | 3.14 | 0 | MI0000105 | 7q32.3 | Yes | 8 |
| hsa-mir-106b | 5.448 | 2.37 | 0 | MI0000734 | 7q22.1 | Yes | 2 |
| hsa-mir-132 | 5.445 | 6.39 | 0 | MI0000449 | 17p13.3 | Yes | 110 |
| hsa-mir-214 | 5.440 | 2.58 | 0 | MI0000290 | 1q24.3 | Yes | 62 |
| hsa-mir-7-3 | 5.418 | 4.72 | 0 | MI0000265 | 19p13.3 | Yes | 12 |
| hsa-mir-29c | 5.406 | 3.12 | 0 | MI0000735 | 1q32.2 | Yes | 8 |
| hsa-mir-367 | 5.398 | 3.47 | 0 | MI0000775 | 4q25 | Yes | NA |
| hsa-mir-30c-2 | 5.356 | 4.10 | 0 | MI0000254 | 6q13 | Yes | 27 |
| hsa-mir-27b | 5.344 | 2.98 | 0 | MI0000440 | 9q22.32 | Yes | 40 |
| hsa-mir-140 | 5.251 | 3.09 | 0 | MI0000456 | 16q22.1 | Yes | 95 |
| hsa-mir-10b | 5.218 | 3.46 | 0 | MI0000267 | 2q31.1 | Yes | 33 |
| hsa-mir-20 | 5.208 | 3.45 | 0 | MI0000076 | 13q31.3 | Yes | 2 |
| hsa-mir-129-1 | 5.143 | 3.97 | 0 | MI0000252 | 7q32.1 | No | 93 |
| hsa-mir-340 | 5.123 | 2.67 | 0 | MI0000802 | 5q35.3 | Yes | 181 |
| hsa-mir-30a | 5.119 | 3.29 | 0 | MI0000088 | 6q13 | Yes | 28 |
| hsa-mir-30c-1 | 5.065 | 3.88 | 0 | MI0000736 | 1p34.2 | Yes | 27 |
| hsa-mir-106a | 4.974 | 2.81 | 0 | MI0000113 | Xq26.2 | Yes | 2 |
| hsa-mir-32 | 4.763 | 2.34 | 0 | MI0000090 | 9q31.3 | Yes | 63 |
| hsa-mir-95 | 4.582 | 2.53 | 0 | MI0000097 | 4p16.1 | Yes | 87 |
| hsa-mir-222 | 4.417 | 3.48 | 0 | MI0000299 | Xp11.3 | Yes | 103 |
| hsa-mir-30e | 4.149 | 4.01 | 0 | MI0000749 | 1p34.2 | Yes | 28 |
| hsa-mir-129-2 | 3.946 | 2.27 | 0 | MI0000473 | 11p11.2 | Yes | 93 |
| hsa-mir-345 | 3.909 | 2.31 | 0 | MI0000825 | 14q32.2 | Yes | 193 |
| hsa-mir-143 | 3.808 | 2.58 | 0 | MI0000459 | 5q32 | Yes | 74 |
| hsa-mir-182 | 3.762 | 3.78 | 0 | MI0000272 | 7q32.2 | Yes | 126 |
| hsa-mir-1-1 | 3.674 | 2.22 | 0 | MI0000651 | 20q13.33 | Yes | 35 |
| hsa-mir-133a-1 | 3.583 | 2.66 | 0 | MI0000450 | 18q11.2 | Yes | 25 |
| hsa-mir-200c | 3.463 | 3.08 | 0 | MI0000650 | 12p13.31 | Yes | 111 |
| hsa-mir-194-1 | 3.345 | 3.57 | 0 | MI0000488 | 1q41 | Yes | 54 |
| hsa-mir-210 | 3.330 | 2.73 | 0 | MI0000286 | 11p15.5 | Yes | 134 |
| hsa-mir-181c | 3.116 | 2.38 | 0 | MI0000271 | 19p13.12 | Yes | 21 |
| hsa-mir-192 | 2.905 | 2.71 | 0 | MI0000234 | 11q13.1 | Yes | 64 |
| hsa-mir-220 | 2.877 | 2.45 | 0 | MI0000297 | Xq25 | Yes | 101 |
| hsa-mir-213 | 2.825 | 2.61 | 0 | MI0000289 | 1q31.3 | Yes | 21 |
| hsa-mir-323 | 2.589 | 3.75 | 0 | MI0000807 | 14q32.31 | Yes | 23 |
| Downregulated microRNAs | | | | | | | |
| hsa-mir-326 | −6.697 | 0.36 | 0 | MI0000808 | 11q13.4 | Yes | 148 |
| hsa-mir-155 | −6.357 | 0.21 | 0 | MI0000681 | 21p21.3 | Yes | 150 |
| hsa-mir-339 | −5.531 | 0.41 | 0 | MI0000815 | 7q22.3 | Yes | 191 |
| hsa-mir-34c | −4.924 | 0.42 | 0 | MI0000743 | 11q23.1 | Yes | 94 |
| hsa-mir-345 | −4.873 | 0.49 | 0 | MI0000825 | 14q32.2 | Yes | 193 |
| hsa-mir-152 | −4.837 | 0.50 | 0 | MI0000462 | 17q21.32 | No | 59 |
| hsa-mir-372 | −4.221 | 0.43 | 0 | MI0000780 | 19q13.42 | Yes | 217 |
| hsa-mir-128a | −4.149 | 0.50 | 0 | MI0000447 | 2q21.3 | No | 51 |

(a) Score: T-statistic values.
(b) q value: this is the lowest False Discovery Rate at which the gene is called significant. It is like the familiar "p-value", adapted to the analysis of a large number of genes.
(c) Active site: indicates if the probe contains the mature form of the microRNA.
(d) microRNA Family: related microRNA based on homology in the hairpin flanking reions as reported in The miRBase Sequence Database - Release 7.0.

TABLE 4

Differentially-expressed microRNAs between ACCss and Normal Bulk Pancreas
(FDR: 0% on the 90th percentile and 2-Fold).

| MicroRNA Name | Score (a) | Fold Change | q-value (b) | Accession ID | Chromosome | Active site (c) | microRNA Families (d) |
|---|---|---|---|---|---|---|---|
| Upregulated microRNAs | | | | | | | |
| hsa-mir-103-2 | 3.926 | 6.46 | 0 | MI0000108 | 20p13 | Yes | 20 |
| hsa-mir-25 | 3.871 | 4.79 | 0 | MI0000082 | 7q22.1 | Yes | 69 |
| hsa-mir-200c | 3.828 | 3.88 | 0 | MI0000650 | 12p13.31 | Yes | 111 |
| hsa-mir-335 | 3.702 | 3.46 | 0 | MI0000816 | 7q32.2 | Yes | 192 |
| hsa-mir-21 | 3.532 | 5.22 | 0 | MI0000077 | 17q23.2 | Yes | 61 |
| hsa-mir-103-1 | 3.474 | 6.09 | 0 | MI0000109 | 5q34 | Yes | 20 |
| hsa-mir-92-1 | 3.419 | 3.13 | 0 | MI0000093 | 13q31.3 | Yes | 30 |
| hsa-mir-181b-2 | 3.369 | 3.35 | 0 | MI0000683 | 9q33.3 | Yes | 44 |
| hsa-mir-191 | 3.344 | 4.95 | 0 | MI0000465 | 3p21.31 | Yes | 176 |
| hsa-mir-93 | 3.299 | 3.60 | 0 | MI0000095 | 7q22.1 | Yes | 2 |
| hsa-mir-26a-1 | 3.248 | 3.85 | 0 | MI0000083 | 3p22.3 | Yes | 39 |
| hsa-mir-17 | 3.211 | 3.76 | 0 | MI0000071 | 13q31.3 | Yes | 2 |
| hsa-mir-20 | 3.201 | 3.37 | 0 | MI0000076 | 13q31.3 | Yes | 2 |
| hsa-mir-107 | 3.195 | 6.16 | 0 | MI0000114 | 10q23.31 | Yes | 20 |
| hsa-mir-26b | 3.185 | 4.15 | 0 | MI0000084 | 2q35 | Yes | 39 |
| hsa-mir-215 | 3.123 | 4.70 | 0 | MI0000291 | 1q41 | Yes | 64 |
| hsa-mir-92-2 | 3.088 | 3.60 | 0 | MI0000094 | Xq26.2 | Yes | 30 |
| hsa-mir-192 | 3.044 | 3.24 | 0 | MI0000234 | 11q13.1 | Yes | 64 |
| hsa-mir-342 | 2.997 | 3.37 | 0 | MI0000805 | 14q32.2 | Yes | 186 |
| hsa-mir-100 | 2.918 | 3.36 | 0 | MI0000102 | 11q24.1 | Yes | 17 |
| hsa-mir-3p21-v | 2.895 | 2.35 | 0 | NA | NA | Yes | NA |
| hsa-mir-106a | 2.833 | 3.02 | 0 | MI0000113 | Xq26.2 | Yes | 2 |
| hsa-mir-15a | 2.809 | 2.83 | 0 | MI0000069 | 13q14.2 | Yes | 24 |
| hsa-mir-23a | 2.748 | 4.23 | 0 | MI0000079 | 19p13.12 | Yes | 32 |
| hsa-mir-181b-1 | 2.732 | 4.00 | 0 | MI0000270 | 1q31.3 | Yes | 44 |
| hsa-mir-128b | 2.709 | 2.58 | 0 | MI0000727 | 3p22.3 | Yes | 51 |
| hsa-mir-106b | 2.485 | 2.50 | 0 | MI0000734 | 7q22.1 | Yes | 2 |
| hsa-mir-194-1 | 2.432 | 3.21 | 0 | MI0000488 | 1q41 | Yes | 54 |
| hsa-mir-219-1 | 2.404 | 2.06 | 0 | MI0000296 | 6q21.32 | Yes | 47 |
| hsa-mir-24-2 | 2.388 | 3.27 | 0 | MI0000081 | 19p13.12 | Yes | 38 |
| Downregulated microRNAs | | | | | | | |
| hsa-mir-218-2 | −4.346 | 0.27 | 0 | MI0000295 | 5q34 | Yes | 29 |
| hsa-mir-339 | −4.272 | 0.27 | 0 | MI0000815 | 7q22.3 | Yes | 191 |
| hsa-mir-326 | −4.037 | 0.26 | 0 | MI0000808 | 11q13.4 | Yes | 148 |
| hsa-mir-34c | −3.525 | 0.27 | 0 | MI0000743 | 11q23.1 | Yes | 94 |
| hsa-mir-152 | −3.507 | 0.31 | 0 | MI0000462 | 17q21.32 | No | 59 |
| hsa-mir-138-2 | −3.398 | 0.33 | 0 | MI0000455 | 16q13 | Yes | 88 |
| hsa-mir-128a | −3.021 | 0.33 | 0 | MI0000447 | 2q21.3 | No | 51 |

(a) Score: T-statistic values.
(b) q value: this is the lowest False Discovery Rate at which the gene is called significant. It is like the familiar "p-value", adapted to the analysis of a large number of genes.
(c) Active site: indicates if the probe contains the mature form of the microRNA.
(d) microRNA Family: related microRNA based on homology in the hairpin flanking reions as reported in The miRBase Sequence Database - Release 7.0.

TABLE 5

Differentially-expressed microRNAs between PETs and PACC
(FDR: 1% on the 90th percentile and 2-fold).
Upregulated microRNAs

| MicroRNA Name | Score (a) | Fold Change | q-value (b) | Accession ID | Chromosome | Active site (c) | microRNA Families (d) |
|---|---|---|---|---|---|---|---|
| hsa-mir-125a | 4.382 | 4.19 | 0 | MI0000469 | 19q13.41 | Yes | 9 |
| hsa-mir-99a | 3.711 | 3.62 | 0 | MI0000101 | 21q21.1 | Yes | 17 |
| hsa-mir-99b | 3.287 | 4.25 | 0 | MI0000746 | 19q13.41 | Yes | 17 |
| hsa-mir-125b-1 | 3.271 | 3.33 | 0 | MI0000446 | 11q24.1 | Yes | 9 |
| hsa-mir-342 | 3.152 | 3.00 | 0 | MI0000805 | 14q32.2 | Yes | 186 |
| hsa-mir-130a | 3.101 | 2.69 | 0 | MI0000448 | 11q12.1 | Yes | 50 |
| hsa-mir-100 | 3.028 | 2.93 | 0 | MI0000102 | 11q24.1 | Yes | 17 |
| hsa-mir-132 | 2.952 | 5.44 | 0 | MI0000449 | 17p13.3 | Yes | 110 |

TABLE 5-continued

Differentially-expressed microRNAs between PETs and PACC
(FDR: 1% on the 90th percentile and 2-fold).

Upregulated microRNAs

| MicroRNA Name | Score (a) | Fold Change | q-value (b) | Accession ID | Chromosome | Active site (c) | microRNA Families (d) |
|---|---|---|---|---|---|---|---|
| hsa-mir-129-2 | 2.910 | 3.86 | 0 | MI0000473 | 11p11.2 | Yes | 93 |
| hsa-mir-125b-2 | 2.886 | 2.94 | 0 | MI0000470 | 21q21.1 | Yes | 9 |

(a) Score: T-statistic values.

(b) q value: this is the lowest False Discovery Rate at which the gene is called significant. It is like the familiar "p-value", adapted to the analysis of a large number of genes.

(c) Active site: indicates if the probe contains the mature form of the microRNA.

(d) microRNA Family: related microRNA based on homology in the hairpin flanking reions as reported in The miRBase Sequence Database - Release 7.0.

TABLE 6

Differentially-expressed microRNAs between WDEC and ACC
(FDR: 1% on the 90th percentile and 2-fold).

| MicroRNA Name | Score (a) | Fold Change | q-value (b) | Accession ID | Chromosome | Active site (c) | microRNA Families (d) |
|---|---|---|---|---|---|---|---|
| *Upregulated microRNAs* | | | | | | | |
| hsa-mir-125a | 3.785 | 3.76 | 0 | MI0000469 | 19q13.41 | Yes | 9 |
| hsa-mir-99a | 3.186 | 3.65 | 0 | MI0000101 | 21q21.1 | Yes | 17 |
| hsa-mir-132 | 2.969 | 4.84 | 0 | MI0000449 | 17p13.3 | Yes | 110 |
| *Downregulated microRNAs* | | | | | | | |
| hsa-mir-148a | −3.781 | 0.21 | 0 | MI0000253 | 7p15.2 | Yes | 59 |

(a) Score: T-statistic values.

(b) q value: this is the lowest False Discovery Rate at which the gene is called significant. It is like the familiar "p-value", adapted to the analysis of a large number of genes.

(c) Active site: indicates if the probe contains the mature form of the microRNA.

(d) microRNA Family: related microRNA based on homology in the hairpin flanking reions as reported in The miRBase Sequence Database - Release 7.0.

TABLE 7

Differentially-expressed microRNAs between Insulomas and Non-Functioning PETs
(FDR: 1% on the 90th percentile and 2-fold).
Upregulated microRNAs

| MicroRNA Name | Score (a) | Fold Change | q-value (b) | Accession ID | Chromosome | Active site (c) | microRNA Families (d) |
|---|---|---|---|---|---|---|---|
| hsa-mir-204 | 5.441 | 6.07 | 0 | MI0000284 | 9q21.11 | Yes | 43 |
| hsa-mir-203 | 4.079 | 2.83 | 0 | MI0000283 | 14q32.11 | No | 113 |
| hsa-mir-211 | 3.931 | 2.81 | 0 | MI0000287 | 15q13.3 | Yes | 43 |

(a) Score: T-statistic values.
(b) q value: this is the lowest False Discovery Rate at which the gene is called significant. It is like the familiar "p-value", adapted to the analysis of a large number of genes.
(c) Active site: indicates if the probe contains the mature form of the microRNA.
(d) microRNA Family: related microRNA based on homology in the hairpin flanking reions as reported in The miRBase Sequence Database - Release 7.0.

TABLE 8

Differentially expressed MicroRNAs between PETs with different clinicopathological parameters.

| MicroRNA Name | Score (a) | Fold Change | q-value (b) | Accession ID | Chromosome | Active site (c) | microRNA Families (d) |
|---|---|---|---|---|---|---|---|
| PET with or without liver metastasis (FDR: 0% on the median percentile and 1.8-Fold). Upregulated microRNA | | | | | | | |
| hsa-mir-21 | 2.239446173 | 1.93 | 0 | MI0000077 | 17q23.2 | Yes | 61 |
| PET with High (Ki67 > 2%) or Low (Ki67 ≦ 2%) proliferation index (FDR: 0% on the median percentile and 1.8-Fold). Upregulated microRNA | | | | | | | |
| hsa-mir-21 | 2.869445623 | 1.84 | 0 | MI0000077 | 17q23.2 | Yes | 61 |
| Non-Functioning PETs with High (Ki67 > 2%) or Low (Ki67 ≦ 2%) proliferation index (FDR: 0% on the median percentile and 2-Fold). Upregulated microRNA | | | | | | | |
| hsa-mir-21 | 2.513043962 | 2.10 | 0 | MI0000077 | 17q23.2 | Yes | 61 |
| WDECs with High (Ki67 > 2%) or Low (Ki67 ≦ 2%) proliferation index (FDR: 0% on the median percentile and 2-Fold). Upregulated microRNA | | | | | | | |
| hsa-mir-021 | 1.642156912 | 2.32 | 0 | MI0000077 | 17q23.2 | Yes | 61 |

(a) Score: T-statistic values.
(b) q value: this is the lowest False Discovery Rate at which the gene is called significant. It is like the familiar "p-value", adapted to the analysis of a large number of genes.
(c) Active site: indicates if the probe contains the mature form of the microRNA.
(d) microRNA Family: related microRNA based on homology in the hairpin flanking reions as reported in The miRBase Sequence Database - Release 7.0.

TABLE 9

Putative gene targets of miR-204/211 identified by three prediction methods

| Symbol | Acc Num | UniGene ID | Gene Name | Ensembl. Gene. ID | Gene ID | Chromosome |
|---|---|---|---|---|---|---|
| CDH2 | NM_001792 | Hs.464829 | Cadherin 2, type 1, N-cadherin (neuronal) | ENSG00000170558 | 1000 | 18q11.2 |
| KHDRBS1 | NM_006559 | Hs.445893 | KH domain containing, RNA binding, signal transduction associated 1 | ENSG00000121774 | 10657 | 1p32 |
| MAPRE2 | NM_014268 | Hs.532824 | Microtubule-associated protein, RP/EB family, member 2 | ENSG00000166974 | 10982 | 18q12.1 |
| NCOA7 | NM_181782 | Hs.171426 | Nuclear receptor coactivator 7 | ENSG00000111912 | 135112 | 6q22.32 |
| ATF2 | NM_001880 | Hs.425104 | Activating transcription factor 2 | ENSG00000115966 | 1386 | 2q32 |
| GLIS3 | NM_152629 | Hs.162125 | GLIS family zinc finger 3 | ENSG00000107249 | 169792 | 9p24.2 |
| EPHA7 | NM_004440 | Hs.73962 | EPH receptor A7 | ENSG00000135333 | 2045 | 6q16.1 |
| C10orf56 | NM_153367 | Hs.523080 | Chromosome 10 open reading frame 56 | ENSG00000165424 | 219654 | 10q22.3 |
| AP3M1 | NM_012095 | Hs.500104 | Adaptor-related protein complex 3, mu 1 subunit | ENSG00000185009 | 26985 | 10q22.2 |
| PRO0149 | NM_014117 | Hs.221497 | PRO0149 protein | ENSG00000182831 | 29035 | 16p13.2 |
| NRBF2 | NM_030759 | Hs.449628 | Nuclear receptor binding factor 2 | ENSG00000148572 | 29982 | 10q21.3 |
| M11S1 | NM_005898 | Hs.471818 | Membrane component, chromosome 11, surface marker 1 | ENSG00000135387 | 4076 | 11p13 |
| MYO10 | NM_012334 | Hs.481720 | Myosin X | ENSG00000145555 | 4651 | 5p15.1-p14.3 |
| NOVA1 | NM_002515 | Hs.211225 | Neuro-oncological ventral antigen 1 | ENSG00000139910 | 4857 | 14q |
| NTRK2 | NM_006180 | Hs.494312 | Neurotrophic tyrosine kinase, receptor, type 2 | ENSG00000148053 | 4915 | 9q22.1 |
| hSyn | NM_018157 | Hs.368253 | Brain synembryn | ENSG00000111785 | 55188 | 12q23.3 |
| HMGA2 | NM_003483 | Hs.505924 | High mobility group AT-hook 2 | ENSG00000149948 | 8091 | 12q15 |
| AKAP1 | NM_003488 | Hs.463506 | A kinase (PRKA) anchor protein 1 | ENSG00000121057 | 8165 | 17q21-q23 |
| OGT | NM_003605 | Hs.405410 | O-linked N-acetylglucosamine (GlcNAc) transferase (UDP-N-acetylglucosamine:polypeptide-N-acetylglucosaminyl transferase) | ENSG00000147162 | 8473 | Xq13 |
| CCNT2 | NM_001241 | Hs.292754 | Cyclin T2 | ENSG00000082258 | 905 | 2q21.3 |

TABLE 10

Putative target genes of miR-204/211 and miR-21 found to be differentially expressed

| Gene Target | Fold | p. value |
| --- | --- | --- |
| Putative target genes of miR-204/211 found differentially expressed between NF-PETs and insulinomas. EST microarray contains 16 out of 20 identified putative target genes. | | |
| UPREGULATED | | |
| MAPRE2 | 1.75 | 0.0070 |
| AP3M1 | 1.30 | 0.0330 |
| DOWNREGULATED | | |
| MYO10 | 0.43 | 0.0014 |
| AKAP1 | 0.59 | 0.0114 |
| Putative target genes of miR-21 found differentially expressed between PET with or without liver metastasis. EST microarray contains 11 out of 12 identified putative target genes. | | |
| UPREGULATED | | |
| NFIB | 1.69 | 0.038 |
| DOWNREGULATED | | |
| PDCD4 | 0.71 | 0.001 |
| Putative target genes of miR-21 found differentially expressed between PET high (Ki67 > 2) or low (Ki67 ≦ 2). EST microarray contains 11 out of 12 identified putative target genes. | | |
| DOWNREGULATED | | |
| PDCD4 | 0.66 | 0.00001 |

A Common microRNA Expression Pattern Distinguishes Pancreatic Endocrine and Acinar Tumors from Normal Pancreas.

The vast majority of the differentially expressed microRNAs found in PACC vs. normal tissue were also found in PET vs. normal tissue. In particular, 28 of 30 (93%) microRNAs that were overexpressed in PACC were also found to be upregulated in PET. Similarly, five of seven (71%) underexpressed microRNAs were down-regulated in both tumor subtypes. This overlap, together with the fact that only a limited set of microRNAs were differentially expressed between PET and PACC or among PET subtypes, is suggestive of a pattern of microRNA expression common to acinar and insular-derived tumors.

Figures 2A, 2B:
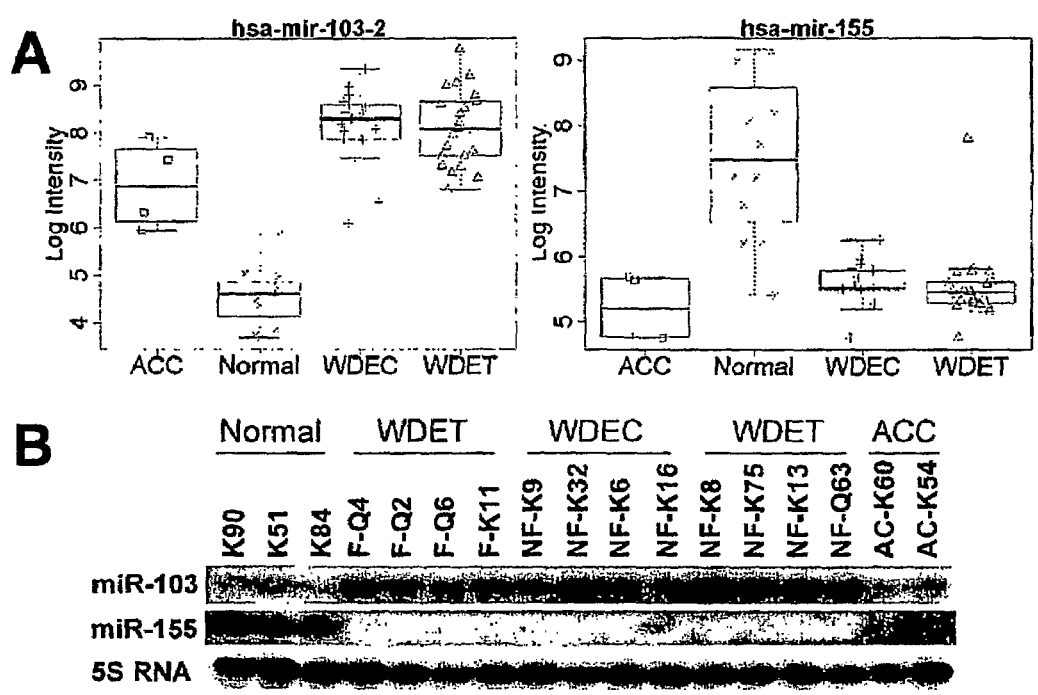
FIG. 2A depicts box-and-whiskers plots showing the expression levels of miR-103 and miR-155, which were measured by microarray analysis of 12 normal pancreas (Normal) and 44 pancreatic tumors, including 22 well-differentiated pancreatic endocrine tumors (WDET), 18 well-differentiated pancreatic endocrine carcinomas (WDEC) and 4 pancreatic acinar cell carcinomas (ACC). The median intensity is highlighted by bold lines. As shown, the overexpression of miR-103 and lack of expression of miR-155 is particular to pancreatic insular and acinar tumors.
FIG. 2B depicts Northern blot analysis, which parallels the microarray expression data shown in FIG. 2A. 5S rRNA (5S-RNA) served as a loading control.
Figures 6A, 6B, 6C:
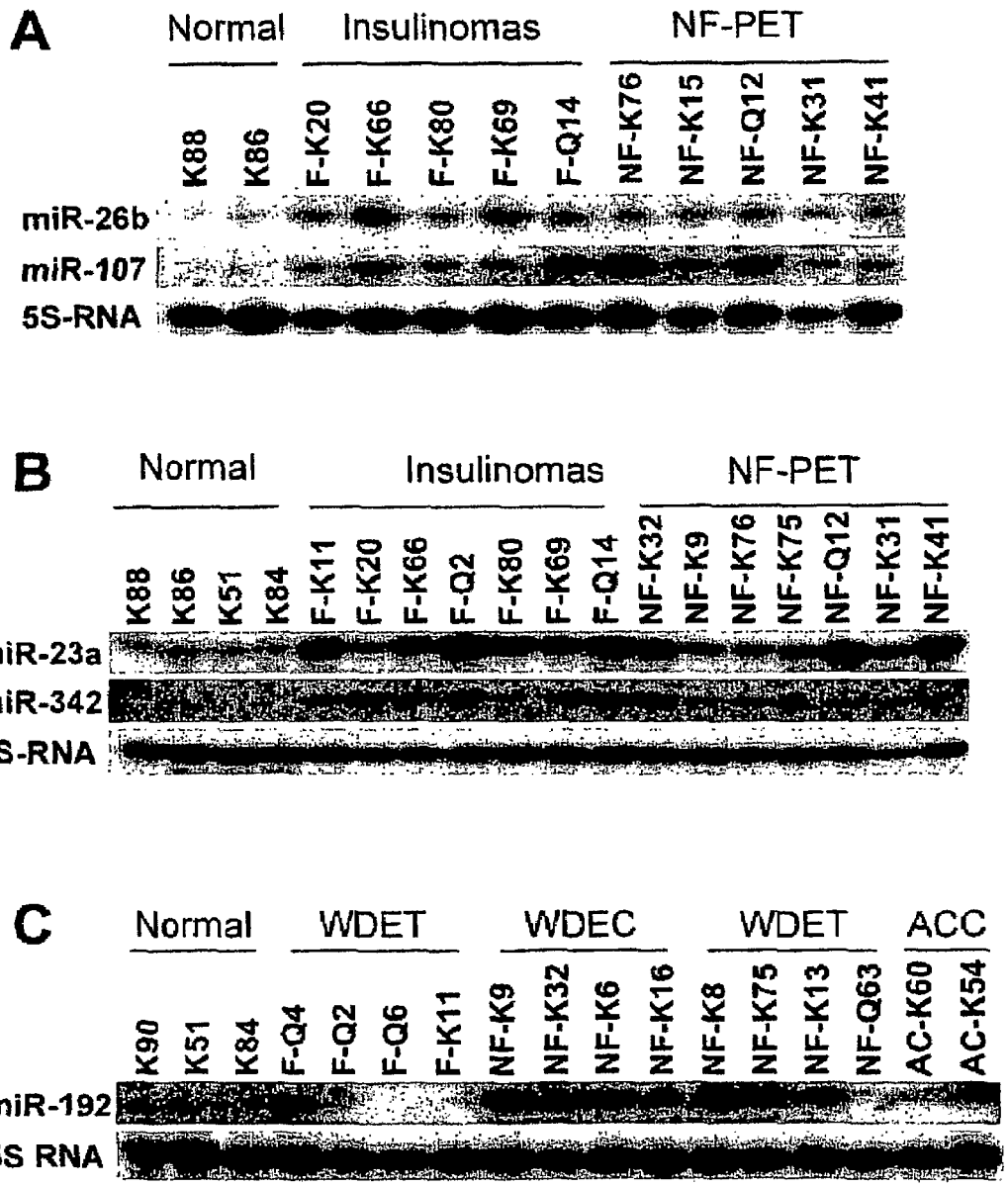
FIG. 6A depicts Northern blot analysis showing overexpression of miR-26b and miR-107 in all the pancreatic insulinomas and non functioning endocrine tumors (NF-PET) that were tested. These results validate the microarray data for the overexpressed microRNAs. 5S rRNA (5S-RNA) served as a loading control.
FIG. 6B depicts Northern blot analysis showing overexpression of miR-23a and miR-342 in all the pancreatic insulinomas and non functioning endocrine tumors (NF-PET) that were tested. These results validate the microarray data for the overexpressed microRNAs. 5S rRNA (5S-RNA) served as a loading control.
FIG. 6C depicts Northern blot analysis showing overexpression of miR-192 in four of eight well-differentiated endocrine tumors (WDET), in all four well-differentiated endocrine carcinomas (WDEC), and one acinar cell carcinoma (ACC). These results validate the microarray data for the overexpressed microRNA. 5S rRNA (5S-RNA) served as a loading control.

Among the upregulated microRNAs in PET that are also common to PACC, seven were validated by Northern blot analysis. In particular, miR-103 was the best discriminator for all pair-wise comparisons of normal pancreas, acinar cell carcinomas and pancreatic endocrine tumors (FIGS. 2A and 2B). The expression of miR-107 paralleled that of its highly homologous miR-103, and the significant overexpression of miR-23a, miR-26b, miR-192, and miR-342 in tumors vs. normal was also confirmed (FIGS. 6A-6C).

Among downregulated microRNAs in PET, Northern blot analysis of miR-155 showed the lack of detectable expression in both PET and PACC (FIGS. 2A and 2B). Although miR-155 was not among the top listed downregulated genes in PACC (Table 4), its low expression in this tumor type was also detected by microarray, as shown in the box-and-whiskers plot of FIG. 2A A Limited Set of microRNAs Distinguishes Pancreatic Endocrine from Acinar Tumors.

The direct comparison of PET and PACC showed only 10 upregulated microRNAs (Table 5), all of which were also overexpressed in PET vs. normal tissue. In contrast, no microRNA was found to be specifically upregulated or downregulated in PACC.

Over-Expression of miR-204 is Specific to Insulinomas and Correlates with Immunohistochemical Expression of Insulin.

Figures 3A, 3B, 3C:
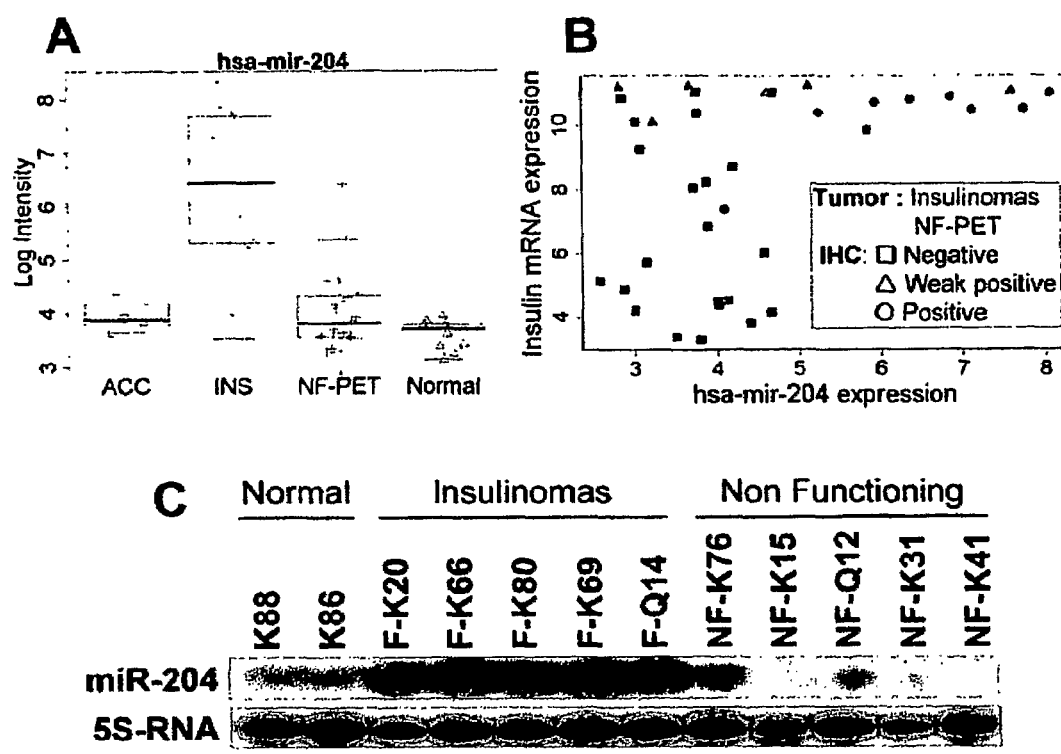
FIG. 3A depicts a box-and-whiskers plot showing the expression level of miR-204, which was measured by microarray analysis of 12 normal pancreas (Normal), 12 insulinomas, 28 non functioning pancreatic endocrine tumors (NF-PET) and 4 pancreatic acinar cell carcinomas (ACC). The median intensity is highlighted by bold lines.
FIG. 3B is a graph showing a strong correlation between miR-204 expression and insulin staining assessed by immunohistochemistry (IHC).
FIG. 3C depicts Northern blot analysis, which confirms the microarray expression data and shows that miR-204 overexpression is specific to insulinomas. 5S rRNA (5S-RNA) served as a loading control.

The comparison of insulinomas with NF-PET identified only three microRNAs that were significantly overexpressed in insulinomas, including miR-204, its homolog miR-211, and miR-203 (Table 7). Notably, the expression of insulin protein, as detected by immunohistochemical staining, correlated with miR-204 expression more strongly than with insulin mRNA expression (FIG. 3A-3C). In fact, logistic regression analysis, based on negative or positive ICH staining, showed that the insulin protein expression was predicted by both insulin mRNA and miR-204 expression (p<0.001); however, in a multivariate model only miR-204 expression retained statistical significance (p<0.001).

Figures 7A, 7B, 7C:
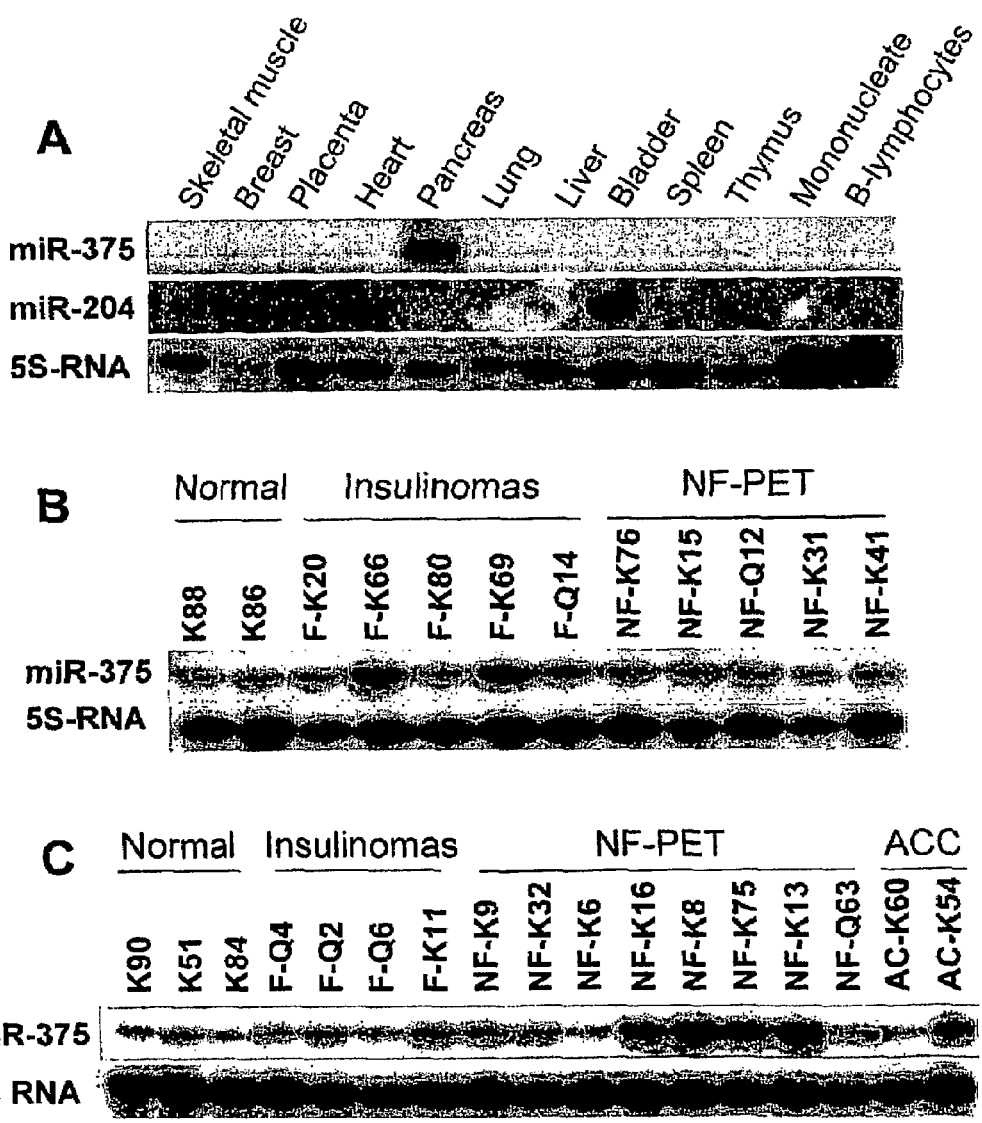
FIG. 7A depicts Northern blot analysis showing that miR-375 is a pancreas-specific miR. 5S rRNA (5S-RNA) served as a loading control.
FIG. 7B depicts Northern blot analysis showing that the expression of miR-375 is a feature of pancreatic endocrine and acinar tumors, irrespective of the presence (insulinomas) or absence (NF-PET) of clinically evident insulin oversecretion. NF-PET, nonfunctioning pancreatic endocrine tumors. 5S rRNA (5S-RNA) served as a loading control. As is shown, mir-375 expression is common in pancreatic insular and acinar tumors.
FIG. 7C depicts Northern blot analysis showing that the expression of miR-375 is a feature of pancreatic endocrine and acinar tumors, irrespective of the presence (insulinomas) or absence (NF-PET and ACC) of clinically evident insulin oversecretion. NF-PET, nonfunctioning pancreatic endocrine tumors; ACC, pancreatic acinar cell carcinomas. 5S rRNA (5S-RNA) served as a loading control. As is shown, mir-375 expression is common in pancreatic insular and acinar tumors.

As miR-375 was suggested to be specifically expressed in mouse pancreatic islets and to function as a negative regulator of insulin exocytosis (Poy, M. N., et al., Nature 432:226-30 (2004)), we investigated its expression in normal human tissues and our samples by Northern blot. Using a panel of several human adult tissues, miR-375 was only detected in normal pancreas (FIG. 7A). The expression levels of miR-375 were generally higher in tumors vs. normal pancreas, but showed no difference between insulinomas and nonfunctioning tumors (FIGS. 7B and 7C).

Expression of miR-21 is Strongly Associated with the Proliferation Index and Presence of Liver Metastasis.

Figures 4A, 4B, 4C:
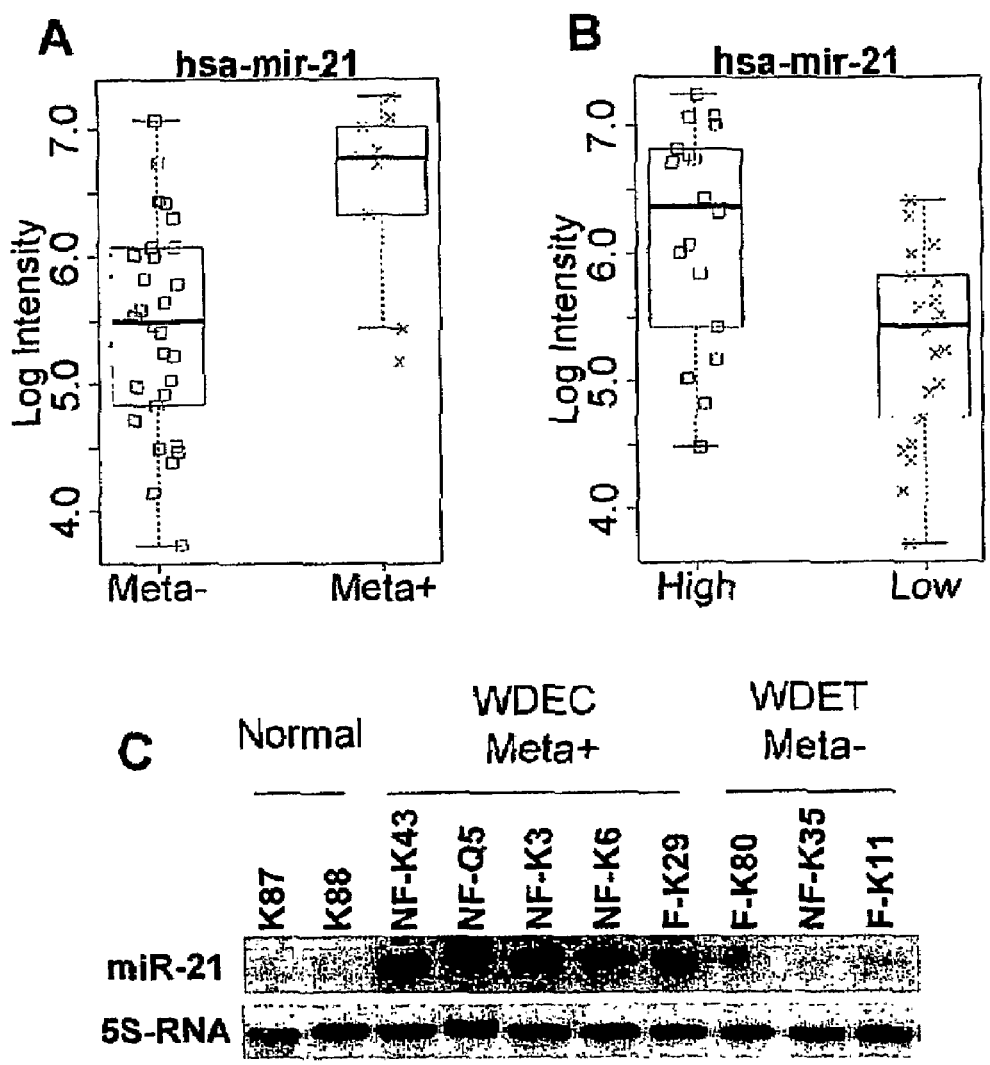
FIG. 4A depicts a box-and-whiskers plot showing the different expression level of miR-21, which was measured by microarray analysis, between pancreatic endocrine tumors with (Meta+) or without (Meta−) liver metastasis. As is shown, expression of miR-21 is strongly associated with the presence of liver metastasis.
FIG. 4B depicts a box-and-whiskers plot showing the different expression level of miR-21, which was measured by microarray analysis, between tumors with a proliferation index >2% (High) or <2% (Low), as measured by Ki67 immunohistochemistry. As is shown, expression of miR-21 is strongly associated with tumoral proliferation index.
FIG. 4C depicts Northern blot analysis, which confirms the microarray expression data. 5S rRNA (5S-RNA) served as a loading control.

The evaluation of expression profiles to identify microRNAs discriminating PETs based on either metastatic status or proliferation index identified only miR-21 as significant (FIGS. 4A-4C and Table 8). This is not surprising, given that these two tumor characteristics are interconnected. In fact, all metastatic PETs had a proliferation index >2%, while no tumor with a lower proliferation score was metastatic. Furthermore, miR-21 also distinguished between NF-PETs or WDEC with high (Ki-67>2%) and low (Ki-67<2%) proliferation index. Another interesting observation is that miR-21 was also overexpressed in PACCs versus normal pancreas (Table 4). Identification of Putative mRNA Targets for Differentially-Expressed microRNAs.

Figure 5:
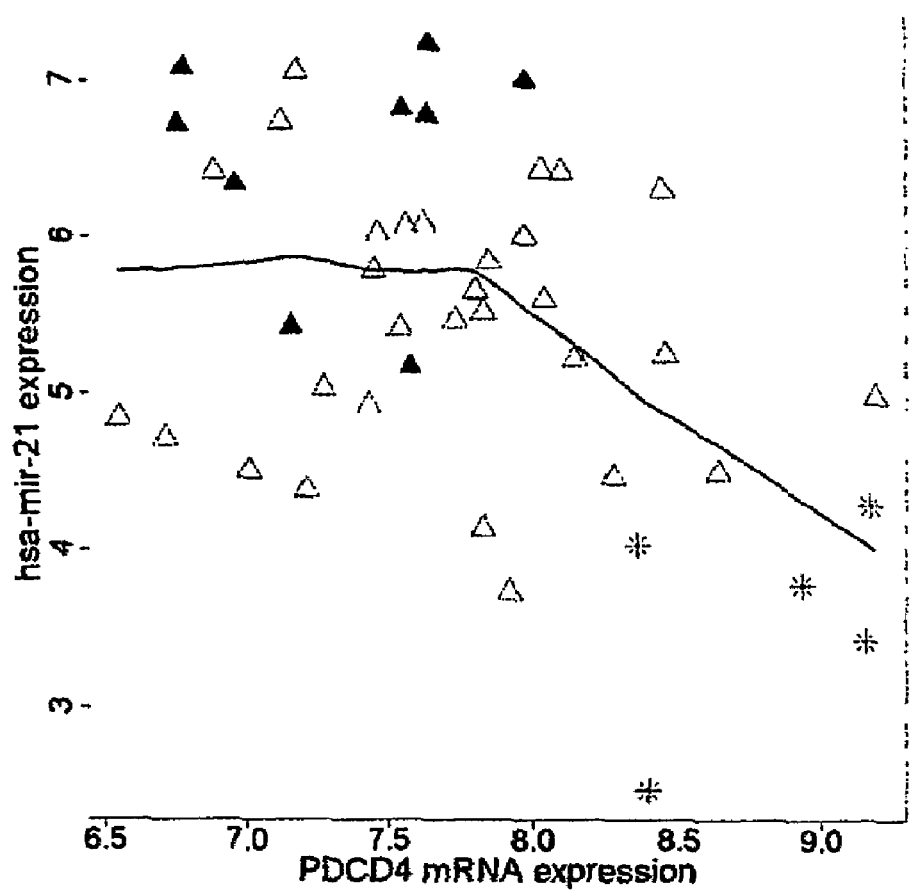
FIG. 5 is a plot showing the expression of miR-21 and PDCD4 mRNA in normal pancreas (*), metastatic (▲) and nonmetastatic (Δ) PET. A Robust locally weighted regression function has been used to fit a line among the data points. As is shown, there is an inverse correlation between the expression of miR-21 and its putative mRNA target PDCD4.

Three different programs (miRanda, TargetScan, PicTar, respectively available at www.microrna.org/mammalian/index.html; www.genes.mit.edu/targetscan/; and www.pictar.bio.nyu.edu) were used to identify predicted targets of selected microRNAs, namely miR-103/miR-107, miR-155, miR-204/miR-211 and miR-21. To increase the stringency of the analysis, we considered only target genes that were found from all three algorithms (Table 9). Because the same tumor samples and five normal pancreas analyzed for microRNA expression have also been evaluated for gene expression profiles with a custom EST microarray (data not shown), we attempted to assess the status of predicted mRNA targets in PET and normal tissue, as well as among PET with different clinicopathological characteristics. A two-sample-t-test analysis identified several putative target genes that were either downregulated or upregulated, namely 28 upregulated and 7 downregulated genes for miR-103/107, 2 upregulated and 2 downregulated genes for either miR-155 or miR-204/211, and 1 upregulated and 1 downregulated gene for miR-21 (Table 10). Notably, the mRNA expression of PDCD4 gene, a putative target of miR-21, was found to be downregulated in liver metastatic PET, as well as in tumors with high proliferation index, showing an inverse correlation with the expression of miR-21 (FIG. 5).

Discussion

The results of the survey of microRNA expression profiles in normal pancreas, pancreatic endocrine tumors and acinar carcinomas may be summarized as follows:

i) a common microRNA expression profile distinguishes both endocrine and acinar tumors from normal pancreas;

ii) the expression of miR-103 and miR-107 associated with lack of expression of miR-155 discriminates tumors from normal;

iii) a limited set of microRNAs is specific to endocrine tumors and is possibly associated with the endocrine differentiation or tumorigenesis;

iv) miR-204 expression occurs primarily in insulinomas and correlates with immunohistochemical expression of insulin; and v) expression of miR-21 is strongly associated with proliferation index and liver metastasis.

Unsupervised hierarchical clustering of the expression profiles showed that both tumor types were separated from normal pancreas. Although PACCs fell into a unique cluster, this was part of the wider cluster including all PETs. While we identified many more differentially expressed microRNAs in PET versus normal than between acinar carcinomas versus normal, the vast majority of differentially expressed microRNAs in PACC were similarly altered in PET. It is worth noting that bulk pancreas is largely formed by acini and therefore represents the ideal normal counterpart for the analysis of acinar cell carcinomas, while pancreatic islet cells would represent the normal counterpart for pancreatic endocrine tumors. Unfortunately, we had no preparations of these cells available. Nonetheless, the finding of a largely concordant pattern of differentially expressed microRNAs between acinar and insular tumors, including 28 upregulated and 5 downregulated genes, suggests that this set common to both tumor types might be related to pancreatic neoplastic transformation. Providing additional support for this assertion, several microRNAs differentially expressed in both tumor types have been found to be differentially expressed in breast, colon and B-cell leukemia (Caldas, C., et al., *Nat. Med.* 11:712-14 (2005); Croce, C. M., and G. A. Calin, *Cell* 122:6-7 (2005); Iorio, M. V., et al., *Cancer Res.* 65:7065-70 (2005)). In addition, at least twenty of the differentially-expressed microRNAs in our tumors have been identified as having either growth related or apoptotic effects in the lung A549 or cervical HeLa carcinoma cell lines (Cheng, A. M., et al., *Nucleic Acids Res.* 33:1290-97 (2005)).

Furthermore, we observed, in both PACC and PET, the coordinate overexpression of miR-17, miR-20 and miR-92-1, which are contained in a polycistronic cluster. This miR-17-92 cluster has been described to act as an oncogene in association with c-MYC gene (He, L., et al., *Nature* 435:828-33 (2005)). Notably, overexpression of c-MYC has been reported in pancreatic endocrine tumors and also in hyperplastic islets, suggesting its involvement in the early phases of insular tumorigenesis (Pavelic, K., et al., *Anticancer Res.* 16:1707-17 (1996)). In addition, induction of MYC in islet or acinar cells of mouse in in vitro or in vivo models produces endocrine tumors (Katic, M., et al., *Carcinogenesis* 20:1521-27 (1999); Lewis, B. C., et al., *Genes Dev.* 17:3127-38 (2003)) or mixed acinar/ductal adenocarcinomas (Sandgren, E. P., et al., *Proc. Natl. Acad. Sci. USA* 88:93-97 (1991), respectively, while suppression of MYC-induced apoptosis leads to islet cells carcinoma (Pelengaris, S., et al., *Cell* 109:321-34 (2002)).

The expression of the two highly homologous miR-103 and miR-107 microRNAs together with the lack of expression of miR-155 was distinctive of tumors vs. normal pancreatic samples. Interestingly, miR-103/107 have been found to be overexpressed in several tumor types (U.S. application No. Ser. No. 12/012,235; entitled "Micro-RNA-Based Methods and Compositions for the Diagnosis and Treatment of Solid Cancers", by Stefano Volinia, George A. Calin and Carlo M. Croce; filed on same date as the subject application; the teachings of which are incorporated herein by reference in their entirety). The finding that miR-155 was expressed in normal pancreas but was underexpressed or not expressed in both PET and PACC is rather interesting considering that overexpression of miR-155 has been observed in lymphomas (Caldas, C., et al., *Nat. Med.* 11:712-14 (2005); Croce, C. M., and G. A. Calin, *Cell* 122:6-7 (2005)) and breast cancer (Iorio, M. V., et al., *Cancer Res.* 65:7065-70 (2005)), a finding that has led to speculation that miR-155 may be an oncogenic microRNA (Croce, C. M., and G. A. Calin, *Cell* 122:6-7 (2005)). This may not be unexpected, as microRNAs expressed in adults are tissue-specific (Babak, T., et al., *RNA* 10:1813-19 (2004)) and the consequences of microRNA misexpression is highly dependent on the cell-specific expression pattern of mRNAs that are microRNA regulated (Cheng, A. M., et al., *Nucleic Acids Res.* 33:1290-97 (2005)).

Ten microRNAs were peculiarly overexpressed in PET and differentiated this tumor from both PACC and normal pancreas. These included miR-99a, miR-99b, miR-100, miR-125a, miR-125b-1, miR-125b-2, miR-129-2, miR-130a, miR-132, and miR-342. These microRNAs may be characteristic of either endocrine differentiation or endocrine tumorigenesis. On the other hand, no microRNA was found to be specifically upregulated or downregulated in PACC, although the limited number of PACC samples may have affected the power of the analysis.

Although the microRNA profiles were almost indistinguishable between insulinomas and nonfunctioning endocrine tumors, the overexpression of the two closely related microRNAs, namely miR-204 and miR-211, was largely restricted to insulinomas. Of great interest, miR-204 expression correlated with the immunohistochemical expression of insulin. In this respect, miR-375 has been recently reported to be specifically expressed in mouse pancreatic islets and to function as a negative regulator of insulin exocytosis (Poy, M. N., et al., *Nature* 432:226-30 (2004)). Our data showed that this microRNA is expressed in human normal pancreas, as well as in acinar cell and endocrine tumors. However, no difference was found in its expression level between insulinomas and nonfunctioning endocrine tumors.

We also determined if microRNA expression was correlated with the clinical characteristics of PETs. Our results showed that miR-21 overexpression is associated with both enhanced Ki-67 proliferation index and liver metastasis. miR-211 overexpression has been observed in several cancers, including glioblastoma, breast, lung and colon cancers (Caldas, C., et al., *Nat. Med.* 11:712-14 (2005); Croce, C. M., and G. A. Calin, *Cell* 122:6-7 (2005)). A cancer-related function of miR-21 is also supported by knockdown experiments in glioblastoma cell lines showing that this microRNA has an anti-apoptotic function (Chan, J. A., et al., *Cancer Res.* 65:6029-33 (2005)). In this respect, the programmed cell death 4 (PDCD4) gene, putatively targeted by miR-21, was found to be significantly downregulated in metastatic and high proliferative PET samples, and showed an inverse correlation with the expression of miR-21. This gene has been reported to act as a tumor suppressor through activation of $p21^{wafl}$ and inhibition of transcription factor complex AP-1; the latter controls genes that have been implied in cellular invasion and metastatic progression (Jansen, A. P., et al., *Mol. Cancer Ther.* 3:103-10 (2004)). Furthermore, PDCD4 expression is lost in progressed carcinomas of lung, breast, colon and prostate cancer (Goke, R., et al., *Am. J. Physiol. Cell Physiol.* 287:C1541-46 (2004)), and notably, a tumor suppressor role for PDCD4 has been also reported in a model of neuroendocrine tumor cells (Goke, R., et al., *Ann. N.Y. Acad. Sci.* 1014:220-21 (2004)).

Differentially-expressed microRNAs in PETs showed a nonrandom distribution among chromosomal arms and most of the microRNAs located at chromosomal arms 5q, 7q, 13q and 19p were overexpressed. This finding may be due to either the frequent association of microRNAs in polycistronic clusters (Baskerville, S. and D. P. Bartel, *RNA* 11:241-47 (2005); Altuvia, Y., et al., *Nucleic Acids Res.* 33:2697-2706 (2005)) or the amplification of the chromosomal arms containing these microRNAs. Our analysis suggests that both phenomena can be involved in PET. In fact, the correlation coefficients measured between pairs of microRNAs within clusters differed significantly from those between pairs of microRNAs outside the clusters. These data confirm in PET the general observation that grouped microRNA genes show coordinate expression (Baskerville, S, and D. P. Bartel, *RNA* 11:241-47 (2005); Altuvia, Y., et al., *Nucleic Acids Res.* 33:2697-2706 (2005)).

MicroRNAs exert their biological effects by targeting specific mRNAs for degradation or translational inhibition. In order to get insights into the biological implications of the most interesting microRNAs showing altered expression in pancreatic tumors, e.g., miR-103/miR-107, miR-115, miR-204/miR-211 and miR-21, we searched predicted targets that were in common among those identified by three different algorithms (see RESULTS). Then, to evaluate if there was a correlation between the expression of microRNAs and that of their predicted targets, we took advantage of the EST expression profiles of the same tumor and normal samples. Among the selected targets that were contained in our EST microarray, we found several upregulated and downregulated genes. Interestingly, the predicted target genes of miR-103/107 were overexpressed more frequently than expected. This finding parallels that of Babak et al., who reported a low correlation between microRNA expression and their predicted mRNA targets in a set of 17 different mouse tissues (Babak, T., et al., *RNA* 10:1813-19 (2004)). This supports the currently favored model that most microRNAs act more likely through translational inhibition without mRNA degradation (Bartel, D. P., *Cell* 116:281-97 (2004)).

In conclusion, the results described herein suggest that alteration in microRNA expression is related to endocrine and acinar neoplastic transformation and progression of malignancy.

The relevant teachings of all publications cited herein that have not explicitly been incorporated by reference, are incorporated herein by reference in their entirety. In addition, the nucleotide sequences (e.g., microRNA nucleotide sequences) identified herein by reference to specific Accession Number are also incorporated herein by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed is:

1. A method of diagnosing whether a subject has, or is at risk for developing, pancreatic cancer, comprising measuring the level of at least one miR gene product in a test sample from said subject, wherein an alteration in the level of the miR gene product in the test sample, relative to the level of a corresponding miR gene product in a control sample, is indicative of the subject either having, or being at risk for developing, pancreatic endocrine cancer (PET), wherein the miR-gene product comprises miR-21.

2. The method of claim 1, wherein the level of the at least one miR gene product in the test sample is greater than the level of the corresponding miR gene product in the control sample.

3. The method of claim 1, wherein the level of the at least one miR gene product in the test sample is less than the level of the corresponding miR gene product in the control sample.

4. A method of diagnosing the type of pancreatic cancer that a subject has, comprising measuring the level of at least one miR gene product in a test sample from said subject, wherein an alteration in the level of the miR gene product in the test sample, relative to the level of a corresponding miR gene product in a control sample, is indicative of the type of pancreatic cancer, wherein the pancreatic cancer comprises at least endocrine cancer (PET), and wherein the miR-gene product comprises miR-21.

5. The method of claim 4, wherein the level of the at least one miR gene product in the test sample is greater than the level of the corresponding miR gene product in the control sample.

6. The method of claim 4, wherein the level of the at least one miR gene product in the test sample is less than the level of the corresponding miR gene product in the control sample.

7. A method of determining the prognosis of a subject with pancreatic cancer, comprising measuring the level of at least one miR gene product in a test sample from said subject, wherein:

the miR gene product is associated with an adverse prognosis in pancreatic cancer, wherein the pancreatic cancer comprises at least endocrine cancer (PET), and wherein the miR-gene product comprises miR-21; and an alteration in the level of the at least one miR gene product in the test sample, relative to the level of a corresponding miR gene product in a control sample, is indicative of an adverse prognosis.

8. The method of claim 7, wherein the level of the at least one miR gene product in the test sample is greater than the level of the corresponding miR gene product in the control sample.

9. The method of claim 8, wherein the pancreatic cancer is associated with metastasis and/or a high proliferation index.

10. A method of diagnosing whether a subject has, or is at risk for developing, pancreatic cancer, comprising:

(1) reverse transcribing RNA from a test sample obtained from the subject to provide a set of target oligodeoxynucleotides;

(2) hybridizing the target oligodeoxynucleotides to a microarray comprising miRNA-specific probe oligonucleotides to provide a hybridization profile for the test sample; and (3) comparing the test sample hybridization profile to a hybridization profile generated from a control sample, wherein an alteration in the signal of at least one miRNA is indicative of the subject either having, or being at risk for developing, pancreatic cancer, wherein the pancreatic cancer comprises at least endocrine cancer (PET), and wherein the miR-specific probe oligonucleotide comprises miR-21.

11. The method of claim 10 wherein the signal of at least one miRNA, relative to the signal generated from the control sample, is upregulated.

12. The method of claim 10 wherein the signal of at least one miRNA, relative to the signal generated from the control sample, is down-regulated.

* * * * *